(12) United States Patent
Tur et al.

(10) Patent No.: US 7,994,281 B2
(45) Date of Patent: Aug. 9, 2011

(54) CYTOKINE DESIGN

(75) Inventors: Vicente R. Tur, Barcelona (ES); Albert Martinus Van der Sloot, Barcelona (ES); Margaret M. Mullally, Utrecht (NL); Robbert H. Cool, Groningen (NL); Eva E. Szegezdi, Galway (IE); Afshin Samali, Galway (IE); Gregorio Fernandez-Ballester, Elche (ES); Luis Serrano, Barcelona (ES); Wilhelmus J. Quax, Kropswolde (NL)

(73) Assignees: European Molecular Biology Laboratory, Heidelberg (DE); National University of Ireland, Galway (IE); University of Groningen, Groningen (NL)

( * ) Notice: Subject to any disclaimer, the term of this patent is extended or adjusted under 35 U.S.C. 154(b) by 554 days.

(21) Appl. No.: 10/581,856

(22) PCT Filed: Dec. 6, 2004

(86) PCT No.: PCT/IB2004/004335
§ 371 (c)(1),
(2), (4) Date: Jul. 13, 2007

(87) PCT Pub. No.: WO2005/056596
PCT Pub. Date: Jun. 23, 2005

(65) Prior Publication Data
US 2008/0044376 A1 Feb. 21, 2008

(30) Foreign Application Priority Data
Dec. 5, 2003 (GB) .................................. 0328261.3

(51) Int. Cl.
*C07K 14/52* (2006.01)
*C07K 14/525* (2006.01)
(52) U.S. Cl. ........................ 530/350; 530/351
(58) Field of Classification Search ........................ None
See application file for complete search history.

(56) References Cited

U.S. PATENT DOCUMENTS

| 6,740,739 | B1 * | 5/2004 | Ashkenazi et al. | 530/399 |
| 2004/0146968 | A1 * | 7/2004 | Chung et al. | 435/69.1 |
| 2006/0141561 | A1 * | 6/2006 | Kelley et al. | 435/69.1 |
| 2007/0161564 | A1 * | 7/2007 | Ashkenazi et al. | 514/12 |

FOREIGN PATENT DOCUMENTS

| WO | 88/06625 | 9/1988 |
| WO | 99/36535 | 7/1999 |
| WO | 01/00832 | 1/2001 |
| WO | 03/029420 | 4/2003 |
| WO | 04/001009 | 12/2003 |

OTHER PUBLICATIONS

Cha, SS et al., "2.8 Å Resolution Crystal Structure of Human TRAIL, a Cytokine with Selective Antitumor Activity," *Immunity*, 1999, 11(2), 253-261.
Degli-Esposti et al., "Cloning and Characterization of TRAIL-R3, a Novel Member of the Emerging TRAIL Receptor Family," *J. Exp. Med.*, 1997, 186(7), 1165-1170.
Eck, MJ et al., "The Structure of Human Lymphotoxin (Tumor Necrosis Factor-β) at 1.9-Å Resolution," *J. Biol. Chem.*, 1992, 267(4), 2119-2122.
Filikov et al., "Computational stabilization of human growth hormone," *Protein Sci.*, 2002, 11, 1452-1461.
Hymowitz, S.G. et al., "A Unique Zinc-Binding Site Revealed by a High-Resolution X-ray Structure of Homotrimeric Apo2L/TRAIL," *Biochemistry*, 2000, 39(4), 633-640.
Hymowitz, SG et al., "Triggering Cell Death: The Crystal Structure of Apo2L/TRAIL in a Complex with Death Receptor 5," *Mol. Cell.*, 1999, 4(4), 563-571.
Kelley, R.F. et al., "Receptor-selective mutants of Apo2L/TRAIL reveal a greater contribution of DR5 and DR4 to apoptosis signaling," e-published ahead of print Nov. 1, 2004, Manuscript #M410660200v1, 1-41.
Luo et al., "Development of a cytokine analog with enhanced stability using computational ultrahigh throughput screening," *Protein Sci.*, 2002, 11, 1218-1226.
Mongkolsapaya, J. et al., "Structure of the TRAIL-DR5 complex reveals mechanisms conferring specificity in apoptotic initiation," *Nat. Struct. Biol.*, 1999, 6(11), 1048-1053.
Screaton et al., "TRICK2, a new alternatively spliced receptor that transduces the cytotoxic signal from TRAIL," *Curr. Biol.*, 1997, 7(9), 693-696.
Shanafelt, A.B. et al., "An immune cell-selective interleukin 4 agonist," *PNAS*, 1998, 95(16), 9454-9458.
Van der Sloot, A. et al., "Stabilization of TRAIL, an all-β-sheet multimeric protein, using computational redesign," *Protein Engineering, Design & Selection*, 2004, 17(9), 673-680.

* cited by examiner

*Primary Examiner* — David Romeo
*Assistant Examiner* — Daniel C Gamett
(74) *Attorney, Agent, or Firm* — Woodcock Washburn LLP

(57) ABSTRACT

The present invention relates to novel methods for the design of proteins, in particular, cytokines. These methods allow the stabilisation of such cytokines, as well as modification of their selectivity/specificity for their cognate receptors. The invention also relates to various modified proteins that have been designed by the methods of the invention.

1 Claim, 21 Drawing Sheets

CYTOKINE DESIGN

CROSS-REFERENCE TO RELATED APPLICATIONS

Figure 1:
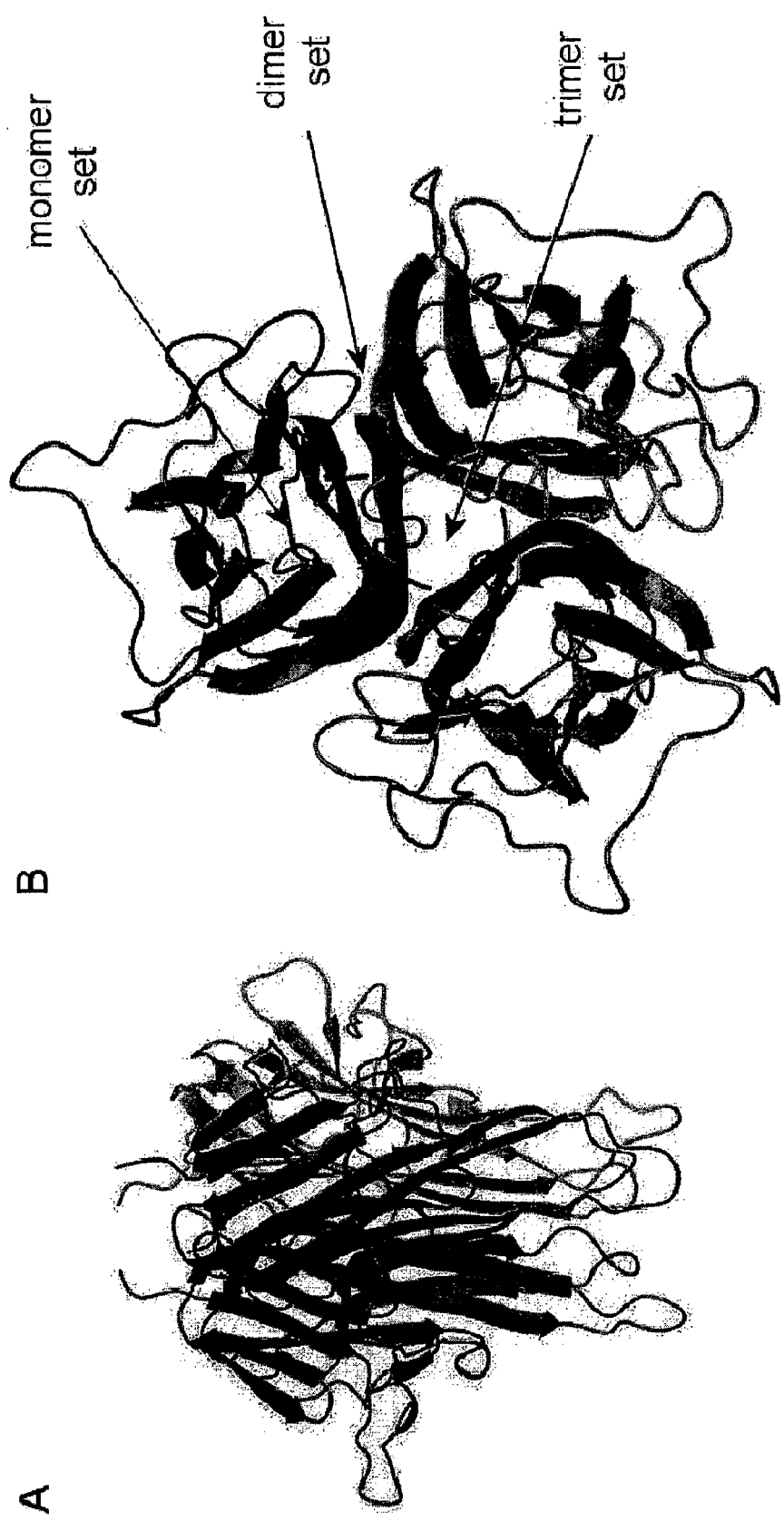

This application is the National Phase of International Application No. PCT/IB2004/004335 filed Dec. 6, 2004, which claims the benefit of Great Britain Application No. 0328261.3 filed Dec. 5, 2003, the disclosures of which are incorporated herein by reference in their entirety.

The present invention relates to novel methods for the design of proteins, in particular, cytokines. These methods allow the stabilisation of such cytokines, as well as modification of their selectivity/specificity for their cognate receptors. The invention also relates to various modified proteins that have been designed by the methods of the invention.

Cytokines are a family of growth factors secreted primarily from leukocytes, and are messenger proteins that act as potent regulators capable of effecting cellular processes at sub-nanomolar concentrations. Their size allows cytokines to be quickly transported around the body and degraded when required. Their role in controlling a wide range of cellular functions, especially the immune response and cell growth has been revealed by extensive research over the last twenty years (Boppana, S. B (1996) Indian. J. Pediatr. 63(4):447-52). These roles include immune response regulation (Nishihira, J. (1998) Int. J. Mol. Med. 2(1):17-28), inflammation (Kim, P. K. et al (2000) Surg. Clin. North. Am. 80(3):885-894), wound healing (Clark, R. A. (1991) J. Cell Biochem. 46(1):1-2), embryogenesis and development, and apoptosis (Flad, H. D. et al (1999) Pathobiology. 67(5-6):291-293).

Clinical use of cytokines to date has focused on their role as regulators of the immune system (Rodriguez, F. H. et al (2000) Curr. Pharm. Des. 6(6):665-680) for instance in promoting a response against thyroid cancer (Schmutzler, C. et al (2000) 143(1):15-24). Their control of cell growth and differentiation has also made cytokines anti-cancer targets (Lazar-Molnar, E. et al (2000) Cytokine. 12(6):547-554; Gado, K. (2000) 24(4):195-209). Novel mutations in cytokines and cytokine receptors have been shown to confer disease resistance in some cases (van Deventer, S. J. et al (2000) Intensive Care Med. 26 (Suppl 1):S98:S102). The creation of synthetic cytokines (muteins) in order to modulate activity and remove potential side effects has also been an important avenue of research (Shanafelt, A. B. et al (1998) 95(16):9454-9458).

Cytokine molecules have thus been shown to play a role in diverse physiological functions, many of which play a role in disease processes. Alteration of their activity is a means to alter the disease phenotype and as such, the identification of novel cytokine molecules is of significant scientific interest.

Of particular interest are ligands that belong to the Tumor Necrosis Factor ligand (TNF) family; these proteins are involved in a wide range of biological activities, ranging from cell proliferation to apoptosis.

Members of the TNF ligand family induce signalling pathways that lead to apoptosis or programmed cell death (PCD) through interaction with their cognate receptors. Ligand-bound receptors transmit the signal across the membrane by bringing their cytoplasmic portions into close proximity, leading to the recruitment and activation of downstream effector proteins. Apoptosis is a process fundamental to the normal development and homeostasis of multicellular organisms. However, the impairment of apoptosis regulation is implicated in the pathogenesis of cancer and several chronic diseases, including acquired immunodeficiency syndrome (autoimmune disease and AIDS) and neurodegenerative disorders (eg Parkinsons). Common examples are chronic transplant dysfunction, rheumatoid arthritis, chronic obstructive pulmonary disease (COPD) and asthma. Molecules that mediate reversal of imbalance in signal transduction could be effective therapeutics in diseases.

Members of the TNF ligand family are also master conductors of immune function and immune tolerance. There is a complex balance between immunostimulatory and immunoregulatory functions within this family that ensures appropriate immune responses. Genetic polymorphisms in the TNF ligand receptor family can result in deregulation of immune homeostasis. Such deregulation can lead to pathogenesis.

The TNF family of ligands interact with their cognate receptors to trigger several signalling pathways that play key roles in regulatory and deleterious effects on immune tolerance, in addition to both protective and pathogenic effects on tissues (Rieux-Laucat et al., 2003, Current Opinion in Immunology 15:325; Mackay and Ambrose, 2003, Cytokine and growth factor reviews, 14: 311; Mackay and Kalled, 2002, Current opinion in Immunology, 14: 783-790). Examples of such proteins include ligands such as RANKL, TRAIL, and APRIL, which are implicated in disease conditions such as rheumatoid arthritis, autoimmune diabetes, systemic lupus erythematosus (SLE), Sjörgen's syndrome, experimental autoimmune encephalomyelitis (EAE), inflammatory bowel disease (IBD), autoimmune lymphoproliferative syndrome (ALPS) and multiple sclerosis.

All monomeric subunits of TNF ligand family members consist of antiparallel β-sheets, organised in a jellyroll topology, and these subunits self associate in bell-shaped homotrimers, the bioactive form of the ligand. Sequence homology is highest between the (aromatic) residues responsible for trimer formation. A trimer binds three subunits of a cognate receptor, each receptor subunit binding in the grooves between two adjacent monomer subunits. The ligands are type II transmembrane proteins, but the extracellular domain of some members can be proteolytically cleaved from the cell surface, yielding a bioactive soluble form of the ligand. Recent reviews of the TNF ligand family are readily available (Locksley et al., *Cell* 104, 487-501 (2001); Bodmer et al., Trends Biochem. Sci. 27, 19-26 (2002)).

Knowledge of members of the TNF ligand family can also be applied to other signalling pathways triggered by ligand-receptor interaction within the same and other families.

Although naturally-occurring cytokines are of significant interest to the scientific community, the properties of many of these molecules do not necessarily suit their application in a clinical setting. For example, the stability of a cytokine is important throughout the production process and for the shelf-life of the final product, as well as influencing the pharmacokinetic and -dynamic properties of the protein therapeutic (Marshall et al., Drug Discov. Today 8, 212-221 (2003)). Several strategies are currently used to augment the thermal stability of proteins (Fersht, A. & Winter, G. Protein engineering. *Trends Biochem. Sci.* 17, 292-295 (1992); Van den Burg et al., *Curr. Opin. Biotechnol.* 13, 333-337 (2002)). Both rational (Pantoliano et al., *Biochemistry* 26, 2077-2082 (1987); Van den Burg et al., *Proc. Natl. Acad. Sci. U.S.A* 95, 2056-2060 (1998); Villegas et al., *Fold. Des* 1, 29-34 (1996)) and directed evolution methods (Giver et al., *Proc. Natl. Acad. Sci. U.S.A* 95, 12809-12813 (1998); Jung et al., *J. Mol. Biol.* 294, 163-180 (1999)) have been successfully used to improve stability. A disadvantage of a rational approach is that one can design only a limited number of potentially improved variants. In contrast, directed evolution methods allow large numbers of variants to be generated and screened.

However, suitable selection/screening procedures are required, which are often not available or are very labour intensive.

More recently, computational redesign algorithms have been employed to enhance stability, amongst other properties, of proteins (DeGrado et al., *Annu. Rev. Biochem.* 68, 779-819 (1999)). These methods combine computer design steps with in silico screening, permitting screening of a much larger sequence space than is experimentally possible with high-throughput techniques. Efficient algorithms are needed to search the vast sequence space and accurate scoring functions are required in order to rank the best designs (Dantas et al., *J. Mol. Biol.* 332, 449-460 (2003)). Some limited success has been achieved for certain proteins—for example, computational redesign has recently been used to generate a hyperthermophilic variant of streptococcal Gβ1 domain protein (Malakauskas, S. M. & Mayo, S. L. Nat. Struct. Biol. 5, 470-475 (1998)), to enhance the stability of the spectrin SH3 domain (Ventura et al., *Nat. Struct. Biol.* 9, 485-493 (2002)) and to improve the (thermal) stability of the therapeutically interesting four helix bundle cytokines, granulocytecolony stimulation factor (G-CSF) and human growth hormone (hGH). However, the various shortcomings of these methods do not allow their widespread application.

It would also be of great use were it possible to alter the selectivity/specificity of cytokines for their receptors. For example, certain members of the TNF ligand family bind more than one receptor or bind decoy receptors which lack or have truncated intracellular domains. A specific example is the tumor necrosis factor-related apoptosis inducing ligand (TRAIL; TNFSF10) Wiley et al., *Immunity.* 3, 673-682 (1995); Pitti et al., *J. Biol. Chem.* 271, 12687-12690 (1996)), which in its soluble form binds its receptors DR4 (TRAIL-R1) and DR5 (TRAIL-R2), in addition to its decoy receptors, DcR1 (TRAIL-R3), DcR2 (TRAIL-R4) and OPG. Receptors DR4 (TRAIL-R1) and DR5 (TRAIL-R2) contain the cytoplasmic Fas associated death domain (FADD), and binding of TRAIL to these receptors induces apoptosis. TRAIL also appears to be able to induce the proliferative NF-κB pathway through Tumor necrosis factor receptor associated death domain (TRADD). Having selective inducers of DR4 (TRAIL-R1) and DR5 (TRAIL-R2) signalling is likely to be of great interest, due to the presumably different cross-linking requirements of both death receptors. Depending on the cross-linking, the signalling pathway could induce the proliferative or the apoptic pathway. DcR1 (TRAIL-R3) and DcR2 (TRAIL-R4) do not contain a death domain or contain a truncated death domain, respectively. Binding to these receptors does not induce apoptosis; on the contrary, it may actually prevent apoptosis by sequestering available TRAIL. DcR2 (TRAIL-R4) however appears also be capable of inducing the NF-κB pathway. Unlike other apoptosis inducing TNF family members, TRAIL appears to be inactive against normal healthy tissue, therefore attracting great interest as a potential cancer therapeutic (Ashkenazi et al., *J. Clin. Invest* 104, 155-162 (1999)). A recent significant publication has however shown that TRAIL-R3 is upregulated by p53 in breast tumour cell through use of the genotoxic drug, doxorubicin (Ruiz de Almodóvar et al., 2003, Nov. 17, Manuscript M311243200). This implies that efficacy of wild-type TRAIL may be diminished in anti-tumour therapy since it also binds the decoy receptors (that do not initiate apoptosis). Therefore, variants of TRAIL, that have altered selectivity/specificity could be direct to the pro-apoptotic receptors, DR4 (TRAIL-R1) or DR5 (TRAIL-R2) and would have ultimately improved application in cancer treatment.

The TNF ligand family members, such as TRAIL, APRIL, RANKL BAFF, LIGHT, FasL and TNF-a all bind more than one receptor. At least six death-domain-containing receptors have now been identified—Fas, TNF receptor 1 (TNF-R1), death receptor 3 (DR3; also known as TRAMP, WsI, APO-3 and LARD), the two receptors for TNF-related apoptosis-inducing ligand (TRAIL) TRAIL-R1/DR4 and TRAIL-R2/DR5, and DR6. Certain member of the TNF ligand family also bind decoy receptors which lack or have truncated death domains, such as, TRAIL, which binds its decoy receptors, DcR1, DcR2 and OPG. The accumulation of recent knowledge in this area, therefore, opens new avenues for therapeutic design. In this respect, selectivity of novel molecules is of primary importance to discern the specific role of the activation of different receptors and therefore the functional effects of ligand binding to several receptors, and the concomitant influence on the pathogenesis of the associated diseases related to signal activation.

Rational design permits only a relative small amount of variants to be designed. For molecular evolution/high throughput screening (HTS) methods, selection and screening methods have to be developed and large libraries of variants have to be screened. Especially for enhancement of stability there are relatively few examples of successful selection or screening methods.

Directed evolution methods allow large numbers of variants to be generated and screened. However, suitable selection/screening procedures are required, which are often not available or are very labour intensive. Such methods rely on partial randomization of the DNA sequence of a particular template protein, generating millions to billions of variants. Improved variants are selected from this vast pool using an iterative selection or screening process over several rounds by employing techniques such as phage display.

A patent entitled "APO-2 LIGAND/TRAIL VARIANTS AND USES THEREOF" (WO 2004/001009 A2) describing DR4 and DR5 selective TRAIL variants published on 31 Dec. 2003. A scientific paper by Kelley et al., describing related subject matter published in 2004 (Kelley, R. F. et al., e-published ahead of print Nov. 1, 2004 manuscript number M410660200v1).

Using data derived from a previous performed alanine scan (Hymowitz, S. G. et al. Biochemistry 39, 633-640 (2000)), Kelley et al., constructed libraries with a size between 0.2 to 2.5 billion unique TRAIL variants. A potential disadvantage of this approach, e.g. constructing a library using positions derived from the alanine scan, is that other advantageous mutations for achieving receptor selectivity/specificity at positions not found in the alanine scan library are missed. Positions e.g. 195 and 218 were screened in the alanine scan, however mutation to alanine did not yield a clear indication for shifting selectivity and therefore those positions were not included in the library. Using phage-display, receptor selective variants were obtained, having on average ~6 amino acid substitutions relative to wild-type TRAIL. It was concluded that to achieve receptor selectivity multiple amino acid substitutions were required.

Computational design methods known in the art have only been applied to improve the stability of relatively small monomeric molecules, not to improve the stability of larger multimeric molecules. Often these designs are focused on changing amino acids in the core of the molecule. Changing residues in the core (repacking the core) does stabilise molecules to some extent, but can lead to a molten globule state.

Computational design methods have also been used in the art to alter selectivity, but again only for relatively small monomeric molecules, not to improve the selectivity for binding partners of larger multimeric molecules. Furthermore, crystal structure is currently indispensable.

One aspect of the present invention uses a combination of computational redesign algorithms and educated manual input to design proteins that are more stable than their wild-type counterparts.

A second aspect of the invention relates to the redesign of proteins to alter their selectivity for receptor.

SUMMARY OF THE INVENTION

According to a first aspect of the invention, there is provided a computer-implemented method for the stabilisation of a β sheet multimeric cytokine, comprising the step of: mutating a residue in a monomer component of the multimeric cytokine protein so as to improve the free energy of the monomer or of the multimeric complex relative to the wild-type unmutated monomer component, wherein said mutated residue is non-conserved between homologous members of the cytokine family.

Variants of β sheet multimeric cytokines with enhanced stability have a number of advantages, including increased in vivo and in vitro half-lives, increased yields generated during protein expression, greater stability during purification and an extended shelf-life compared to their wild-type counterparts. Stable variants of these proteins can thus be used as protein therapeutics or diagnostics. The proteins have a relatively close resemblance to the wild-type structure and this reduce the risk of immunogenicity, particularly when compared to variants stabilised by fusion tags, one currently favoured method of stabilising proteins. They also have advantages when compared to agonistic or antagonistic antibodies. In contrast to antibodies, variants can be produced in *Escherichia coli* and the mode of signalling more closely resembles that used by the wild-type cytokine protein.

The term "multimeric cytokine" as used herein is meant to include all β sheet multimeric cytokines. Examples of such cytokines are presented in Table 6. Other examples will be known to those of skill in the art. A recent review on structure of TNF ligand family is available (Bodmer et al., 2002. Trends Biochem. Sci. 27, 19).

One feature of β sheet multimeric cytokines is that they are composed of identical monomeric subunits or of different monomeric subunits. Methodologies could be applied to all cytokine protein families and more specifically to the members of the TNF ligand-receptor family. Other examples of families of proteins embraced by the superfamily of cytokines include those classed as Beta-Trefoil, Beta-sandwich, EGF-like, and Cystine knot cytokines).

Of particular interest for the application of the methodology of the invention are the β sheet multimeric cytokines that are members of the tumor necrosis factor ligand family. Ligands belonging to this family are involved in a wide range of biological activities, ranging from cell proliferation to apoptosis, and they share similar structural characteristics. All monomeric subunits of these ligands consist of antiparallel β-sheets, organized in a jelly-roll topology, and these subunits self associate in bell-shaped homotrimers, the bioactive form of the ligand. A trimer binds three subunits of a cognate receptor, each receptor subunit binding in the grooves between two adjacent monomer subunits. The ligands are type II transmembrane proteins, but the extracellular domain of some members can be proteolytically cleaved from the cell surface, yielding a bioactive soluble form of the ligand.

It has been found advantageous to use alignment information in order to focus the design on non-conserved residue positions. This method of protein stabilisation focuses on these non-conserved residues on the premise that conserved residues are usually retained in a family for a good reason and it is probable that any mutation of a conserved residue will decrease protein stability. On the other hand, regions with high sequence variability are tolerant to mutation and it can be expected that variants that stabilize the protein can be found in these regions. There is less evolutionary pressure for these residues to have been retained among the family members.

The combined approach of the method therefore employs family alignment information and a computational design algorithm. This reduces the sequence space search for every position in the protein being studied and decreases the computing time and power necessary for the methodology.

Identification of non-conserved residues can be done using any one of a number of systems known to the person of skill in the art. Such an analysis can be done by eye, but is more easily achieved using a computer-implemented alignment algorithm, such as BLAST (Altschul et al. (1990) J Mol Biol., 215(3): 403-10), FASTA (Pearson & Lipman, (1988) Proc Natl Acad Sci USA; 85(8): 2444-8) and, more preferably, PSI-BLAST (Altschul et al. (1997) Nucleic Acids Res., 25(17): 3389-402), ClustalW (Thompson et al., 1994, NAR, 22(22), 4673-4680) or the like. Assessment of whether or not a residue is conserved will be clear to the skilled reader and will depend on the number of related proteins that are aligned and the degree of relatedness amongst them. For example, if only two family members are aligned and these proteins share 50% identity, then the conserved residues are those that are shared between the two proteins at the same positions. On the other hand, if 20 proteins in the same family are aligned, it is most unlikely that the least alike of these proteins will possess homology as high as this. Preferably, then, in an alignment between the candidate for mutation and representative members of the protein family, a conserved residue is one that is shared between at least 20% of the family, preferably at least 30%, preferably at least 40%, preferably at least 50%, and may be at least 60%, preferably 70% or more. For example, sequence homology in the Tumor Necrosis Factor ligand family is highest between the (aromatic) residues that are responsible for trimer formation; these residues are thus unsuitable candidates for mutation according to the methodology of the invention.

Once non-conserved residues are identified, the next step in the method requires an evaluation of which of these residues are candidates for mutation.

Preferred aspects of the methodology mutate non-conserved residues that occupy positions at the surface of the monomer component in the multimeric cytokine protein structure. By doing this, the multimeric structure is stabilised as a whole.

As used herein, the term "at the surface" means that the residue concerned in the monomer remains surface-exposed in the multimer complex. Such residues are solvent-exposed and thus hydrophilic in nature. Of course, surface-exposed residues will be present not only at the surface of each monomer, but will also be surface-exposed in the multimer complex. Knowledge of the position of a particular residue in the structure of a protein may come from knowledge of the structure itself, or may be derived by extrapolation from the position of the equivalent residue in the structure of a protein in the same family.

Another preferred aspect of the methodology is to mutate non-conserved residues near positions close to the interface between two monomer components of the multimeric cytokine protein structure. This has the effect of stabilising the multimeric structure of the protein through stabilisation of the inter-chain interfaces.

As used herein, the term "near positions close to the interface between two monomer components" means that the residue concerned in the monomer is close to or at the interface formed when two monomer components of a multimeric protein complex together. The residue must be near enough to this interface for its constituent atoms to influence monomer-monomer interactions, preferably in a positive way. For hydrophobic interactions the distance may be as close as the Van der Waals' radius of subject atoms. For hydrogen bonding the distance may be from 2.7 angstrom to 3.1 angstrom, for electrostatic interaction the distance may be from 1.4 angstrom up to 12 angstrom. Such influence may be effected through, for example, polar or hydrophobic solvation energies, van der Waals' interactions, H-bond energies, electrostatics, or backbone and side chain entropies.

For trimeric proteins, one preferred aspect of the methodology is to mutate residues that occupy positions along the central trimeric axis in the multimeric cytokine protein structure. This has the effect of stabilising the trimer.

As used herein, the term "residues along the central trimeric axis" means that the residue concerned in the monomer is close to or at the interface formed when three monomer components of a trimeric protein complex together. As described above, the residue must be near enough to this interface for its constituent atoms to influence the confluence of the three monomer components into a trimeric complex.

Most preferably, a method according to the invention mutates residues in more than one of the classes referred to above, preferably in at least two of the classes and even more preferably in all three of these classes.

The methodology described here is, to the inventors' knowledge, the first time that a technique incorporating computational engineering has been applied to redesign a large (>100 amino acids) all-β-sheet protein towards a more thermally stable variant.

Until recently, lack of protein structural information in relation to multimeric β sheet cytokines and their receptors made intervention on the level of signal transduction initiation (ligand-receptor interaction) unfeasible. Detailed crystal structural information is now available for many of these cytokines, together with reliable homology models. Therefore, studies on protein-protein interaction and the elucidation of mechanisms of ligand-receptor interaction and activation are now possible. For example, the following TNF ligand family members have been crystallised, either in complexed or uncomplexed forms: Human BAFF, Blys (Liu Y. et al., 2002 Cell 108(3):383-94; Oren D A. et al., 2002 Nat Struct Biol., 9(4):288-92.; Karpusas M. et al., 2002 J Mol Biol. 315(5):1145-54); human CD40L (Karpusas M. et al., 2001, Structure (Camb). April 4; 9(4):321-9); murine RANKL/TRANCE (Lam J. et al., 2001 J Clin Invest. 108(7):971-9); human TNF-a (Banner D W. et al., 1993 Cell. 1993 May 7; 73(3):431-45; Eck M J. et al., 1992 J Biol Chem., 267(4): 2119-22.) human TRAIL (Mongkolsapaya J et al., 1999 Nat Struct Biol. 6(11):1048-53, Cha S S. et al., 1999, 2000 Immunity. 1999 August; 11(2):253-61. 2000 J Biol Chem. 2000 Oct. 6; 275(40):31171-7; Hymowitz S G. et al., 1999 Mol Cell. 4(4):563-71), human TNF-α (Reed C. et al., 1997 Protein Eng. 10(10):1101-7; Cha S S. et al., 1998 J Biol Chem. 1998 Jan. 23; 273(4):2153-60; Naismith J H. et al., 1996 Structure. 1996 Nov. 15; 4(11):1251-62, Naismith J H. et al., 1995, J Biol Chem. 1995 Jun. 2; 270(22):13303-7. 1996 J Mol Recognit. 1996 March-April; 9(2):113-7; Carter P C. et al., 2001 Proc Natl Acad Sci USA; 98(21):11879-84. Erratum in: Proc Natl Acad Sci USA 2001 Dec. 18; 98(26):15393). Therefore, the amino acids that make up domains representing protein-protein interaction motifs between these ligands and their respective receptors are now known. Such interacting domains in the TNF family have an intrinsic propensity to initiate signalling pathways associated with the modulation of diseases such as cancer and chronic diseases such as autoimmune disease, and are starting points for drug design.

Visualisation of the structure of a candidate cytokine protein may be performed computationally using one or other of the many systems available for this task. Such systems are generally designed to import data describing a protein structure (such as a structure from the Protein Data Bank, the PDB) and convert this to a three-dimensional image. At present, the largest public depository of information relating to protein structure is the PDB database (http://www.rcsb.org/pdb), that now includes over 23,000 protein and nucleic acid structures, elucidated using methods of x-ray crystallography and nuclear magnetic resonance. Images of protein structure allow intimate analysis of the structure of a protein to evaluate the positions of each residue in the protein structure, and an evaluation of which residues participate in interactions with other moieties, such as a receptor or monomer partner.

For example, in the example described herein, the structure of the TRAIL protein (Accession No. P50591; TN10_HUMAN, (SEQ ID NOs 1 and 2 herein)) is visualised using the template PDB structure 1DU3 (Cha et al., *J. Biol. Chem.* 275, 31171-31177 (2000)). The crystal structure at 2.2 Å resolution contains the trimeric structure of human TRAIL in complex with the ectodomain of the DR5 (TRAIL-R2) receptor. In this case, the TRAIL monomer lacks an external, flexible loop (130-146), not involved in receptor binding or in monomer-monomer interaction. Accordingly, to complete the molecule, this loop was modelled using the structure of 1D4V (2.2 Å) (Mongkolsapaya et al., Nat. Struct. Biol. 6, 1048-1053 (1999)), a monomeric TRAIL in complex with DR5 (TRAIL-R2) receptor, having the atomic coordinates of the loop. Finally, the TRAIL molecule was isolated by removing the receptor molecules from the PDB file.

Already, there are computer-implemented programs that allow the prediction of protein structure ab initio, or by inference from closely-related proteins of known structure. Accordingly, for the method of the invention, it is not strictly necessary for the structure of a candidate protein to be known. A significant amount of information can be gleaned by analogy from structures of related proteins; for example, TNF ligand family members show similar trimeric structures.

For example, for some β sheet multimeric cytokines, such as APRIL, there is no available structure of the complex with the receptor. However, there is generally structural information available for homologous ligands and receptors, which allows the complexes to be built by Homology Modelling. This is particularly true in those cases in which the sequence homology is higher then 40% and insertions or deletions are not found in the binding region of ligand and receptor.

Visualisation of the isolated monomers, monomer-monomer interface and central core of the candidate protein will show the residues that are potential candidates for mutagenesis.

In the case of design for stability mutants, in order to filter out unsuitable residues for mutagenesis, any highly conserved hydrophobic residues should be discarded from the list of potential candidates for mutagenesis. In addition, residues involved in receptor binding should be discarded in the case of design for stability mutants. These residues cannot be mutated without disrupting interactions with the receptor. The sequence space search for every position may preferably be simplified, by checking the naturally occurring amino acids in a multiple sequence alignment of proteins belonging to the family of interest, thus decreasing the computing time, and subsequently focusing on non-conserved residues.

Preferably, in conjunction with a visualisation tool, a protein design algorithm is used to facilitate the identification of candidate residues for mutation. Examples of suitable algorithm include the "WHATIF" program (Vriend, (1990), J Mol Graph 8(1), 52-6, 29) or more sophisticated programs such as the algorithm "PERLA" (protein engineering rotamer library algorithm) (Fisinger S, Serrano L, Lacroix E. Protein Sci. 2001 April; 10(4):809-18). The latter, based on a rotamer library search, allows a combinatorial exploration at different positions simultaneously in the protein, and identifies the optimal sequence that improves a structural property of the protein (such as its stability). A detailed description of this algorithm is available elsewhere (Lacroix, E. Protein design: a computer based approach, Ph.D. thesis. (U. Libre de Bruxelles, 1999)) (http://ProteinDesign.EMBL-Heidelberg.DE) and its use has been previously described (Ventura et al., Nat. Struct. Biol. 9, 485-493 (2002); Fisinger et al., Protein Sci. 10, 809-818 (2001); Lopez et al., J. Mol. Biol. 312, 229-246 (2001); Reina et al., Nat. Struct. Biol. 9, 621-627 (2002)). Other suitable algorithms include 3D Jigsaw and EasyPred.

Briefly, the PERLA algorithm performs strict inverse folding: a fixed backbone structure is decorated with amino acid side chains from a rotamer library. Relaxation of strain in the protein structure is achieved via the generation of subrotamers. Most terms of the scoring function are balanced with respect to a reference state, to simulate the denatured protein. The side chain conformers are all weighted using the mean-field theory and finally candidate sequences with modelled structures (PDB coordinates) are produced.

In the case of a multimeric protein such as the TNF family ligand TRAIL, protein design with PERLA requires the following steps.

Firstly, residues of a monomer that could establish specific interactions with the contiguous monomer must be identified and selected as described above.

Secondly, side chains that contact the residues that are candidates for mutation must be identified to allow side chain movements that are necessary to accommodate the new residues introduced by the algorithm. PERLA automatically selects these residues based on a geometrical approach that takes $C\alpha$-$C\alpha$ distances and the angle between $C\alpha$-$C\beta$ vectors into consideration.

Thirdly, the algorithm places the amino acid repertoire at each position selected from a set of naturally occurring amino acids in a multiple sequence alignment of the TNF ligand family, and eliminates from consideration those side-chain conformations and amino acids that are not compatible with the rest of the structure.

Fourthly, all possible pair-wise interactions are explored to eliminate those combinations that are less favourable. This energy evaluation is preferably carried computationally, for example using a force field algorithm such as the program FOLD-X (Guerois et al., *J. Mol. Biol.* 320, 369-387 (2002)) or a modified version (Schymkowitz, J., Borg, J., Rousseau, F. & Serrano, L, "manuscript in preparation") of this program, available at (http://fold-x.embl-heidelberg.de). The force field module of FOLD-X evaluates the properties of the structure, such as its atomic contact map, the accessibility of its atoms and residues and the backbone dihedral angles, in addition to the H-bond network and electrostatic network of the protein. The contribution of water molecules making two or more H-bonds with the protein is also preferably taken into account. FOLD-X then proceeds to calculate all force field components: polar and hydrophobic solvation energies, van der Waals' interactions, van der Waals' clashes, H-bond energies, electrostatics, and backbone and side chain entropies.

Finally, an output of sequences and PDB coordinates corresponding to the best calculated solution (in terms of energy) is produced and may be ranked in terms of free energy, for instance, using FOLD-X.

The resultant data files (preferably PDB files or similar) containing the mutations should then be energy-minimized. One way of doing this is by using a program such as GROMOS 43B1 as implemented in Swiss-PdbViewer v3.7b2 (Guex & Peitsch; *Electrophoresis* 18, 2714-2723 (1997)), and evaluated by FOLD-X (http://fold-x.embl-heidelberg.de). The final energies of the models are then compared to the reference, wild-type structure and expressed as ?? G (kcal mol$^{-1}$).

Favourable mutations may of course be combined and evaluated in terms of free energy (kcal mol-1). Unfavourable combinations (e.g. high Van der Waals' clashes) should be eliminated.

If necessary, outputs of sequences and co-ordinates may subsequent to the design process be reintroduced in the design algorithm for a further round or rounds of design. 2nd, $3^{rd}$, $4^{th}$, $5^{th}$ or more rounds of design may be used.

The above methodology facilitates the calculation of free energy, which must be improved by mutation of the monomer, relative to the free energy of wild-type unmutated monomer. By "free energy" is meant the free energy of folding. By "free energy of folding" is meant the difference in Gibbs energy (including enthalpic and entropic terms) between the protein in a folded or partially folded state and the protein in its fully denatured state. In calculating the free energy of folding, the calculation should take into account factors such as the accessibility of atoms, the existence of hydrogen bonds and the existence of electrostatic charges between atoms that are predicted to occur in the folded structure, the van der Waals' interactions, the solvation, the main chain and side chain entropic effects being also taken into account. These atomic energetic calculations are then summed. This calculation should thus ideally take account of the nature of the stabilising interactions that compete with or favour the topological constraints that are inherent in a particular protein folding pathway, taking sequence considerations into account when calculating the main chain, the side chain and the loop entropic costs and the favourable contributions to protein stability. Such a method thus should incorporate detailed energetic functions that effectively estimate the balance between topological constraints (entropic origin) on the one hand and interactions stabilising a fold, on the other.

The free energy of a particular protein may be assessed using any suitable method, as will be clear to the skilled reader. A number of suitable computer programs exist for the automated calculation of free energy; one preferred program is the FOLD-X program (Guerois R, Nielsen J E, Serrano L., J Mol Biol. 2002 Jul. 5; 320(2):369-87) which uses optimal energy functions to rank sequences according to their fitness for a given fold.

Such molecules identified herein specifically interfere at the ligand receptor family interface where apoptosis or autoimmune signalling pathways are triggered. A combined methodology that utilises the design approach outlined above in conjunction with such experimental techniques, is included as an aspect of the present invention.

Molecules generated using the above methods may also be used to elucidate the mechanism of action of β sheet multimeric cytokines. For example, although the crystal structures of TNF family members are known, little is known of the exact mechanism of binding and signal initiation by the ligand-receptor complex. Several TNF ligand family members, such as TRAIL, APRIL and RANKL, bind more than one receptor type which depending on receptor type may or may not trigger signal transduction pathways. Many questions therefore still exist with respect to molecular regulation of diseases such as cancer or autoimmune disease on the level of ligand-receptor complex formation and subsequent initiation of signal transduction. In vitro and in vivo studies aimed at the characterisation of this complex should add to a better understanding of the underlying (patho) physiological response and will aid in creating unique lead molecules. Use of these lead compounds will facilitate the elucidation of more complex basic questions in relation to protein-protein interaction, signal transduction pathways and bioactivity in in vitro and in vivo situations.

In particular, protein or peptide mimetics generated may act as receptor agonists, antagonists, which may be engineered to have increased or decreased structural stability, receptor binding selectivity and/or bioactivity. In particular, such compounds have utility in the regulation of apoptosis. Members of the TNF ligand family induce signalling pathways that lead to apoptosis or programmed cell death (PCD) through interaction with their cognate receptors. Ligand-bound receptors transmit the signal across the membrane by bringing their cytoplasmic portions into close proximity, leading to the recruitment and activation of downstream effector proteins. Apoptosis, the mechanism whereby multicellular organisms dispose of superfluous or damaged cells in a controlled manner, is a process fundamental to the normal development and homeostasis of multicellular organisms. However, the impairment of apoptosis regulation is implicated in the pathogenesis of cancer and several chronic diseases, including acquired immunodeficiency syndrome (autoimmune disease and AIDS) and neurodegenerative disorders (eg Parkinsons). Common examples are chronic transplant dysfunction, rheumatoid arthritis, chronic obstructive pulmonary disease (COPD) and asthma. Molecules that mediate reversal of imbalance in signal transduction could be effective therapeutics in diseases. Cell induced apoptosis is mediated chiefly by members of the TNF ligand family that interact with cognate receptors to trigger apoptosis. Soluble portions of these cytokines or their receptors, or mimetics thereof, are thus attractive candidates to be used as therapeutics for a variety of diseases related to apoptosis impairment.

In addition, a greater understanding of the role of TNF ligand family members may be achieved in controlling lymphocyte function, in order to identify novel targets for autoimmune therapy. Deregulated Activation-Induced Cell Death (AICD) may lead and contribute to autoimmunity. Impairment of AICD leads to accumulation of auto-reactive and chronically activated T cells. These cells can express various immune modulatory ligands, including APRIL and BAFF, which can alter B cell functions, causing autoantibody secretion and finally autoimmunity. The ligation of the TNF receptor family members may either lead to apoptosis through caspase-8/10 activation or, alternatively proinflammatory reactions, cell proliferation and differentiation through activation of NFkB. Activated T cells express a wide range of TNF ligand-receptor family members, all having different effects on lymphocyte fate. APRIL acts as a co-stimulator of T and B cells and enhances T cell survival in autoimmune disease. BAFF is essential for B cell T1 to T2 stage maturation, and thus, immunoglobulin secretion. RANKL initiates differentiation of osteoclast precursors that are responsible for bone desorption. In rheumatoid joints 40% of the leukocytes are T cells, mainly CD4+. The proportion of B cells is only 1-5%, although their contribution to chronic disease development is still great. Accumulation of these cells in inflamed joints leads to further lymphocyte activation and uncontrolled systemic immune responses. In RA, for example, one needs to target both hyper-plastic synovial cells and the immune cells accumulating in the joint capsule and also circulating in the body.

TNF family members are important immune regulators through promotion of proliferation and by participating in AICD of peripheral T cells. Inhibition of endogenous TRAIL function leads to impaired AICD, proliferation of autoreactive lymphocytes and synovial cells resulting in arthritic inflammation and joint tissue destruction (Song K et al. J. Exp. Med., 2000; 191(7):1095). APRIL, on the other hand can act as a co-stimulator of T cells and is able to prolong T cell survival. By dissecting the molecular pathway of T cell activation and the cell death induced by reactivation we can understand the exact role of TNF ligand family members in autoimmunity.

For example, studies of AICD human peripheral T cells may be isolated from the blood of healthy individuals. T cells can be activated by anti-CD3 and anti-CD28 antibodies, or phytohaemagglutinin and maintained in the presence of various amounts of IL-2 and/or IL-15. AICD will then be induced at various days following activation by addition of anti-CD3 monoclonal antibodies. The potential of various TNF family members to induce AICD of CD4+ or CD8+ T cell populations at various times can then be tested by addition of agonistic/antagonistic ligands such as those described herein; these will compete with signalling.

Cell death in the CD4+ and CD8+ population can be tested by, for example, the 7-aminoactinomycin method (Szondy Z et al. 1998, J. Infectious. Dis. 178:1288). In addition, the requirement for IL-2 in sensitising activated T cells to TRAIL-R and Fas-mediated death will be examined. Since IL-15 was shown to inhibit AICD, we will examine whether IL-15 interferes with TNF receptor family expression of activated T cells and thus with sensitisation to AICD (Marks-Konczalik J. et al. PNAS 2000 97(21):11445-11450). Based on these findings a functional assay can be suggested to test possible deficiencies in various autoimmune patients. We will attempt to understand the function of APRIL in modulating T-cell survival. Using APRIL as a co-activator, together with anti-CD3, we will examine how it modulates TRAIL, FasL or TNF signalling, IL-2 secretion and in this way the influence on T cell survival. If TNF ligand family members or variants are shown to have an influence we will proceed to characterise these molecules in several forms of autoimmunity.

According to a further aspect of the invention, therefore, there is provided a β sheet multimeric cytokine whose sequence has been altered so as to generate a more stable cytokine than the wild-type, unaltered cytokine protein. Preferably, the β sheet multimeric cytokine is generated by mutating a residue in a monomer component of the multimeric cytokine protein so as to improve the free energy of the monomer or of the multimeric complex relative to the wild-type unmutated monomer component, wherein said mutated residue is non-conserved between homologous members of the cytokine family.

Multimeric cytokines included within the terms of the invention are all β sheet multimeric cytokines, as described above. Examples are presented in Table 6. Preferred multimeric cytokines according to the invention are members of the TNF ligand family (see Bodmer et al., 2002. Trends Biochem. Sci. 27, 19). A preferred TNF ligand family member is the TRAIL protein.

Preferably, such a β sheet multimeric cytokine is mutated in the soluble C-terminal portion of the molecule. Examples of suitable residues for mutation are those at the following positions:

a) a non-conserved residue at the surface of the monomer component of the multimeric cytokine (herein termed 'monomer' set);

b) a non-conserved residue close to the interface between two of the monomer components of the multimeric cytokine (herein termed 'dimer' set);

c) for trimeric cytokines, a non-conserved residue along the central trimeric axis (herein termed 'trimer' set).

This list is not exhaustive—various miscellaneous mutations may also be made dependent on the particular cytokine, that do not fall into any of the three categories above. The identification of non-conserved residues is described above. Similarly, identification of residues that fall into the above classes a) to c) is also described above.

Preferably, a mutation in category a) falls in the external loop that connects that C and D anti-parallel beta strands of the cytokine (the CD loop), following the notation according to Eck (Eck et al., J. Biol. Chem. 267, 2119-2122 (1992)). Preferred examples of such mutations in the TRAIL protein include positions E194 and I196. Equivalent mutations in other β sheet multimeric cytokines will be apparent to those of skill in the art. Preferably, mutations introduced at these residues are E194I and/or I196S.

In the TRAIL protein, when both these mutations are made, this has been found to result in a large improvement of free energy compared to wild-type TRAIL ($\Delta\Delta G=-9.7$ kcal $mol^{-1}$ $monomer^{-1}$). This high energy value is due to the fact that a trimer is being studied, in addition to the presence of significant van der Waals' clashes in the crystal structure (~5 kcal $mol^{-1}$ $monomer^{-1}$), which are removed upon mutation. Preferably, mutations are made at both positions E194 and I196; more preferably, both the mutations E194I and I196S are made. The predicted increase in stability of this double mutant (herein termed M1) can be explained since Glu 194 is surrounded by hydrophobic groups (Trp 231, Phe 192, Ala 235) and the carboxyl group is uncompensated. The mutation Glu 194 to Ile rectifies this situation by replacing the charged residue for a medium-sized hydrophobic residue. Conversely, Ile 196 is surrounded by polar residues (Asn 202, Lys 233) and is very close to the backbone, resulting in probable van der Waals' clashes. Mutation to Ser avoids clashes and allows formation of a hydrogen bond to Asn 202, located in the opposite part of the CD loop. Both mutations improve polar solvation energy, in addition to ameliorating side chain and backbone entropy.

Preferably, a mutation in the dimer set may be made at one or more of the following positions: 125, 163, 185, 187, 232, 234, 237, 203, 205, 239, 241, 271 and 274. In the TRAIL protein, the residues at these positions are the following: H125, F163, Y185, Q187, S232, D234, Y237, D203, Q205, L239, S241, E271 and F274. The skilled reader will be able to identify equivalent positions in other β sheet multimeric cytokine proteins, for example, by multiple alignment or by structural alignment. Preferred mutations in this class include mutations at D203, Q205 and Y237. Preferably, mutations introduced at these positions are one or more of D203I, Q205M and Y237F. More preferably, two or all three of these mutations are made.

A mutant TRAIL protein comprising these three mutations is herein termed M2. The design of M2 leads to the creation of a hydrophobic cluster to stabilize the interaction between residues 203 and 205 (D strand) of one monomer, and residue 237 (F strand) of the adjacent monomer. Gln 205 and Tyr 237 together form an intermolecular hydrogen bond, and Asp 203 points to a gap in the monomer-monomer interface. Mutation to Ile (203), Met (205) and Phe (237) breaks the Q205-Y237 hydrogen bond, but facilitates the tight packing of these residues, improving van der Waals' interactions, hydrophobic and polar solvation energies of the entire TRAIL molecule, without a further increase of van der Waals' clashes.

Preferably, a mutation in the trimer set may be made at one or more of the following positions: 227, 230 and 240. In the TRAIL protein, the residues at these positions are the following: R227, C230 and Y240. The skilled reader will be able to identify equivalent positions in other β sheet multimeric cytokine proteins. A preferred mutation in this class is R227M.

A mutant TRAIL protein comprising this mutation is herein termed M4. The Arg 227 residues of mutant M4 are located in strand E, equidistantly opposed in a central position along the longitudinal axis of the TRAIL trimer. The three arginines are surrounded by hydrophobic (Ile 242), polar (Ser 241, Ser 225) and aromatic (Tyr 240, Tyr 243) residues. These tyrosines direct the hydroxyl groups away from Arg 227, thus creating a rather hydrophobic cavity. The high concentration of positive charges is apparently not well compensated, since it forms only hydrogen bonds with the backbone (carbonyl groups of Ser 241). Thus, the mutation of these positions to Met could help to accommodate the hydrophobic environment, as well as to decrease the repulsion of monomers due to uncompensated positive charges.

Also the combination of C230S and Y240 is preferred. Replacement of the Cys 230 with Ser removes a zinc binding site thereby introducing unfavourable interactions. The second mutation (Y240F) removes unfavourable interactions to restore thermal stability and biological activity.

Preferably, a mutation in the miscellaneous set may be made at one or more of the following positions: 123, 272, 225, 280, 163, 123 and 208. In the TRAIL protein, the residues at these positions are the following: A123, A272, S225, V280, F163, A123 and V208. The skilled reader will be able to identify equivalent positions in other β sheet multimeric cytokine proteins. A preferred mutation in this class is S225A.

A mutant TRAIL protein comprising this mutation is herein termed M3. Residue 225 of M3 (S225A) is located in strand E and is solvent exposed in the monomeric form. However, after trimerization, this position becomes buried in a small pocket, leaving the side chain of the hydrogen bond donor Ser uncompensated. After mutation to Ala, the energy of the model is better than wild-type TRAIL for both polar and hydrophobic solvation energies, in addition to side chain entropy.

A further preferred mutant β sheet multimeric cytokine is one which incorporates a combination of the mutations described above, such as 2, 3, 4, 5, 6, 7, 8, 9, 10 or more such mutations. One example of such a mutant combines mutations at positions 194, 196 and 225. In the TRAIL protein, the residues at these positions are E194, I196 and S225. Preferably, the mutations introduced are E194I, I196S and S225A; a TRAIL mutant containing these three mutations has been engineered and is referred to herein as C1.

The above mutations may be introduced in the full length cytokine sequence. Preferably, however, the above mutations are introduced into soluble forms of β sheet multimeric cytokines. For the TRAIL protein, a preferred soluble template into which these mutations may be introduced comprises amino acids 114-281 of the full length TRAIL protein. However, as the skilled reader will appreciate, variations in this template will very likely retain the properties of this soluble form and show biological activity if additional residues C terminal and/or N terminal of these boundaries in the polypeptide sequence are included. For example, an additional 1, 2, 3, 4, 5, 10, 20 or even 30 or more amino acid residues from the wild-type cytokine sequence, or from a homologous sequence, may be included at either or both the C terminal and/or N terminal of these boundaries, without prejudicing the ability of the polypeptide fragment to fold correctly and exhibit biological activity. Similarly, truncated variants of this template in which one or a few amino acid residues (for example, 1, 2, 3, 4, 5, 10 or more) may be deleted at either or both the C terminus or the N terminus without prejudicing biological activity The methods described above have been applied to a prototypic example, TRAIL, for purposes of illustration. It will be appreciated that this example is intended as illustrative and is not limiting in any way. Novel mutants of TRAIL have been designed in order to increase the stability of the bioactive trimer. As will be evident from the Examples included herein, using this approach succeeded in extending the apparent thermal stability of the β-sheet protein by more than 5° C. This correlates with the preservation of overall structural characteristics as highlighted by the lasting bioactivity of these mutants as tested experimentally. For example, when measuring the residual bioactivity of wild-type TRAIL and TRAIL mutants upon incubation at 73° C. for 1 hour, it was shown that, while wild-type TRAIL was all but thermally inactivated after ~20 min, the TRAIL mutants M1, M2, M3 and C1, significantly, had an improved stability. Although not tested herein, it has been shown that in case of certain therapeutically interesting proteins, improvement of thermal stability can also be indicative of an improved in vivo half-life (Luo et al., *Protein Sci.* 11, 1218-1226 (2002); Filikov et al., *Protein Sci.* 11, 1452-1461 (2002)). Furthermore, the increase in thermal stability did not affect the biological activity of M1, M3 and C1. Significantly, it is shown herein that stabilisation of the CD loop in a single monomer resulted in stabilisation of the entire trimeric molecule.

As stated above, it would be desirable were it to be possible to alter the selectivity/specificity of cytokines for their cognate receptors. The inventors have now achieved, for the first time, the alteration of the receptor binding selectivity/specificity of a large multimeric protein structure using computational redesign. Automated computer algorithms have been used in combination with hand-crafting and selection of pertinent residues to alter receptor binding selectivity of a multimeric all β-sheet protein, TRAIL.

Accordingly, this aspect of the invention provides a method for the alteration of the selectivity of a β sheet multimeric cytokine for a target receptor, the method comprising identifying amino acids in the cytokine that are located in the receptor-binding interface as candidates for mutation;

discarding residues interacting with amino acids that are conserved among receptors bound by the cytokine protein;

discarding residues interacting with the receptor backbone; and substituting each of one or more residues in the cytokine protein for replacement residues that include amino acid side-chain conformations that are predicted to fit into the binding interface with the target receptor so as to provide an increase in binding affinity of the cytokine protein for that target receptor.

Alternatively, one or more residues in the cytokine protein may be substituted for replacement residues so as to decrease the binding affinity of the cytokine protein for a particular target receptor.

The invention also provides a β sheet multimeric cytokine that is obtained or obtainable by the above methodology.

The invention also provides a β sheet multimeric cytokine with selectivity for a target receptor, wherein one or more amino acids in the cytokine that are located in the receptor-binding interface are substituted for replacement residues that include amino acid side-chain conformations that are predicted to fit into the binding interface with the target receptor so as to provide an increase in binding affinity and selectivity/specificity of the cytokine protein for that target receptor, provided that these are not residues interacting with amino acids that are conserved among receptors bound by the cytokine protein.

Alternatively, the invention provides a β sheet multimeric cytokine with selectivity for two or more target receptors wherein selectivity for a first target receptor is achieved by substituting one or more amino acids in the cytokine for replacement residues so as to decrease affinity for one or more different target receptors, provided that these are not residues interacting with amino acids that are conserved among receptors bound by the cytokine protein.

The target receptors referred to herein may be cognate receptors.

As discussed above, alteration of selectivity for receptor is of significant interest in the cytokine field. For example, TNF ligand family members bind to receptors of the TNF receptor family, and upon binding an intracellular signalling cascade is activated. Different cell subtypes have different profiles of TNF receptor family expression. Many TNF ligand family members can signal through more than one type of TNF receptor family member proteins, resulting in different biological activities, depending on the receptor and the expression profiles of these receptors on the cell surface. For a protein therapeutic/diagnostic it may be advantageous to selectively activate (or inhibit) one of the receptors, for example to differentiate between a cell-proliferating activity and a cell-death inducing activity. Using the method of the invention described above, this is now possible even for large multimeric molecules. Furthermore, an improved selectivity/specificity would allow lower concentrations of a therapeutic variant to be administered than would be necessary with respect to wild-type cytokine.

Such selective variants of cytokines are advantageous for use as protein therapeutics or diagnostics, since they exhibit a relatively close resemblance to the wild-type structure and this reduces the risk of immunogenicity. They also have advantages when compared to agonistic or antagonistic antibodies. In contrast to antibodies, variants can be produced in *Escherichia coli* and the mode of signalling resembles the wild-type mode of signalling more closely.

According to the method of this aspect of the invention, selectivity for receptor is of primary importance. Accordingly, affinity for a receptor may be slightly compromised for improvements in selectivity/specificity.

Using a method such as that described herein, novel mutants of the TRAIL protein have been designed in order to shift selectivity/specificity towards its different membrane receptors (DR4 (TRAIL-R1), DR5 (TRAIL-R2), DcR1 (TRAIL-R3) and DcR2 (TRAIL-R4)). As described above, having selective inducers of DR4 (TRAIL-R1) and DR5 (TRAIL-R2) signalling is of considerable interest, due to the different cross-linking requirements of both death receptors. Depending on the cross-linking the signalling pathway could induce the proliferative or the apoptic pathway.

Some residues important for binding and biological activity have been already identified in TRAIL by alanine-scanning mutagenesis (Hymowitz et al., Biochemistry. 2000 Feb. 1; 39(4):633-40), but in this study, the inventors have focused not only in the identification of critical residues for selectivity, also have suggested the best amino acid substitution at these positions to get a maximum effect in selectivity. We show that some residues are critical for receptor binding and selectivity; alanine-scanning mutagenesis could not identify these. The results also confirm that the choice of amino acid chosen for replacement is important.

This example acts as a prototypic example of how the method of the invention may be applied to a large multimeric β sheet protein. As the skilled reader will be aware, methods used in this study are also applicable to other multimeric cytokines, such as TNF family ligands.

For example, a recent significant publication has shown that TRAIL-R3 is upregulated by p53 in breast tumour cell through use of the genotoxic drug, doxorubicin (Ruiz de Almodóvar et al., J. Biol. Chem 6; 279(6):4093-101 (2003). This implies that efficacy of wild-type TRAIL may be diminished in anti-tumour therapy since it also binds the decoy receptors (that do not initiate apoptosis). Therefore, variants of TRAIL, that have altered selectivity/specificity could be directed to the pro-apoptotic receptors, DR4 (TRAIL-R1) or DR5 (TRAIL-R2) and would have ultimately improved application in cancer treatment.

Methods for identifying amino acids that are located in the receptor-binding interface are known in the art. Preferably, this is done through visualisation of the structure of the ligand protein, ideally in complexed form with receptor, using one or other of the many systems available. Such systems are generally designed to import data describing a protein structure (such as a structure from the Protein Data Bank, the PDB) and convert this to a three-dimensional image. Images of protein structure allow intimate analysis of the structure of the protein to evaluate the positions of each residue in the protein structure, and an evaluation of which residues participate in interactions with other moieties, such as a receptor or monomer partner. Selected side chains are those in the protein ligand that are physically close enough to be potentially interacting with receptor.

If no protein structure is available, it is likely that there will be structural information available for one or more homologous ligands and receptors, which allows the complexes to be built by Homology Modelling. This is particularly true in those cases in which the sequence homology is higher then 40% and insertions or deletions are not found in the binding region of ligand and receptor. For example, in the specific case of alteration of the selectivity of the TRAIL protein for DR5 (TRAIL-R2) or towards DR4 (TRAIL-R1), a crystal model of TRAIL in complex with the ectodomain of the DR5 (TRAIL-R2) receptor is available (PDB identifier 1DU3). Models of TRAIL complexed with the three other membrane receptors (DR4 (TRAIL-R1), DcR1 (TRAIL-R3) and DcR2 (TRAIL-R4)) may be obtained using the "What If Homology Modeling web interface" (Vriend. WHAT IF: A molecular modeling and drug design program. *J Mol. Graph.* (1990) 8, 52-56) (available at http://www.cmbi.kun.nl/gv/servers/WIWWWI/). Pdb files of TRAIL in complex with these three receptors can be generated by imposing their backbone atoms over the same atoms of the receptor DR5 (TRAIL-R2), using a program such as Swiss-PdbViewer v3.7b2 (Guex & Peitsch. SWISS-MODEL and the Swiss-PdbViewer: an environment for comparative protein modeling. *Electrophoresis* 18, 2714-2723 (1997)). Finally, template receptor DR5 (TRAIL-R2) is removed from the generated PDB file.

In a similar manner to the method of protein stabilisation described above, it is considered advantageous to use alignment information in order to focus the design on residues that do not interact with conserved residue positions in the target receptor. On occasion, however, altering conserved residues may also lead to changes in selectivity for the receptor. By conserved residue positions, is meant residues that are conserved between the different receptors that bind to the protein of interest. For example, the TNF ligand family TRAIL binds to four different membrane receptors (DR4 (TRAIL-R1), DR5 (TRAIL-R2), DcR1 (TRAIL-R3) and DcR2 (TRAIL-R4)). Residues in the receptor binding interface that are conserved between the different receptors are likely to contribute to the binding of the ligand protein, meaning that their alteration would very likely disrupt important ligand-receptor interactions that are necessary for effective ligand-receptor binding. For the same reason, any residues that are predicted to interact with the receptor backbone are not considered suitable candidates for mutation.

As described above, identification of non-conserved residues can be done using any one of a number of systems known to the person of skill in the art, but preferably, computer-implemented alignment algorithms such as PSI-BLAST or ClustalW are preferred.

The combined approach of the method therefore employs family alignment information and a computational design algorithm. This reduces the sequence space search for every position in the protein being studied and decreases the computing time and power necessary for the methodology. This methodology allows rational design of the occurring interactions between the protein ligand and its receptors. An overall visual inspection of the binding interface of ligand with the different receptors should also be carried out and, if necessary, some rotamers changed.

The method requires that each of one or more residues in the ligand protein are substituted for replacement residues that include amino acid side-chain conformations that are predicted to fit into the binding interface with the target receptor so as to provide an increase in binding affinity for that receptor. This step is preferably performed using a computer design algorithm such as PERLA, which performs inverse folding. Briefly, this algorithm decorates a fixed backbone structure with amino acid side chains from a rotamer library. PERLA thus performs a rotamer search looking for better side chain conformations, aiming to model the expected interactions of the protein ligand with its receptors. Relaxation of strain in the protein structure is achieved via the generation of subrotamers. Most terms of the scoring function are balanced with respect to a reference state, to simulate the denatured protein. The side chain conformers are all weighted using the mean-field theory and finally candidate sequences with modelled structures (PDB coordinates) are produced. Energy evaluation of the modelled structure must also be performed as part of this methodology, preferably using a program such as FOLD-X[7] or an improved version (such as that available at http://fold-x.embl-heidelberg.de). The force field module of FOLD-X evaluates the properties of the structure, such as its atomic contact map, the accessibility of its atoms and residues, the backbone dihedral angles, in addition to the H-bond network and electrostatic network of the protein. The contribution of water molecules making two or more H-bonds with the protein is also taken into account. FOLD-X then proceeds to calculate all force field components: polar and hydrophobic solvation energies, van der Waals' interactions, van der Waals' clashes, H-bond energies, electrostatics, and backbone and side chain entropies.

Using this program, all possible amino acid substitutions (preferably with the exception of Glycine, Proline, and Cysteine) are then introduced at the selected residue positions in the protein ligand in conformations (side chain rotamers) that are compatible with the rest of the structure. Glycine, Proline, and Cysteine are preferably omitted because Gly and Pro can influence the backbone conformation relatively more than other amino acids (Gly is more flexible, Pro less so). Also these residues have relatively large effects in the denatured state (Gly high entropy, Pro lower). Cys can also be difficult and is in an unpaired state that is generally unwanted in proteins, making them prone to aggregation and the like. Favourable mutations are then evaluated in terms of free energy (kcal mol-1), and unfavourable mutations (e.g. high Van der Waals' clashes) eliminated. An output of sequences and coordinates is then obtained and ranked in terms of free energy, for example, using the FOLD-X program. Some of these predictions can be discarded directly after theoretical energy calculations, without further experimental analysis. Others are progressed to mutagenesis studies. In this way, the method of this aspect of the invention substitutes one or more residues in the ligand protein substituted for replacement residues that include amino acid side-chain conformations that are predicted to fit into the binding interface with the target receptor so as to provide an increase in binding affinity for that target receptor.

Favourable mutations may of course be combined and evaluated in terms of free energy (kcal mol-1). Unfavourable combinations (e.g. high Van der Waals' clashes) should be eliminated.

If necessary, outputs of sequences and co-ordinates may subsequent to the design process be reintroduced in the design algorithm for a further round or rounds of design. 2nd, $3^{rd}$, $4^{th}$, $5^{th}$ or more rounds of design may be used.

Preferably, the method of this aspect of the invention may be applied to multimeric β sheet cytokines. Examples of such cytokines are presented in Table 6. Other examples will be known to those of skill in the art.

Of particular interest for the application of the methodology of the invention are the β sheet multimeric cytokines that are members of the tumor necrosis factor ligand family. Ligands belonging to this family are involved in a wide range of biological activities, ranging from cell proliferation to apoptosis, and they share similar structural characteristics.

According to a further aspect of the invention, there is provided a β sheet multimeric cytokine whose sequence has been altered so as to alter its affinity for a particular target receptor.

Accordingly, one aspect of the invention relates to a cytokine that is mutated at one, two, three, four, five, six, seven, eight, nine, ten, eleven or all twelve of these positions. Preferably, such a cytokine is a member of the TNF ligand family. More preferably, such a cytokine is TRAIL (SEQ ID NO:1 herein). All references to amino acid positions in the TRAIL protein sequence presented herein, and to specific TRIAL mutants are intended to refer to the amino acid sequence given in SEQ ID NO:1. Preferably, the TRAIL sequence is altered so as to alter affinity and/or selectivity for the DR4 (TRAIL-R1) or DR5 (TRAIL R2) receptors.

Examples of suitable residues for mutation in TRAIL are those at the following positions: 131, 269, 130, 160, 218, 220, 149, 155, 214, 195, 191 and 267.

Equivalent residues (when crystal structural information is compared by eye or with use of molecular modelling) identified by those skilled in the art could be mutated in other β sheet multimeric cytokines, preference being for the cytokines of the TNF family.

Equivalent substitutions at the above positions, with a specific type of residue are preferred. For example, a preferred mutation at position 131 is to Arg. Preferred mutations at position 269 are to His, Lys or Arg. A preferred mutation at position 130 is to Glu. Preferred mutations at position 160 are Lys and Met. Preferred mutations at position 218 are to Arg, Tyr, Glu, Phe, Lys or His. Preferred mutations at position 220 are to Met or to His. Preferred mutations at position 149 are to Asp or to His. A preferred mutation at position 155 is to Met. A preferred mutation at position 214 is to Arg. A preferred mutation at position 195 is to Arg. A preferred mutation at position 191 is to Glu. A preferred mutation at position 267 is to Arg.

In the TRAIL protein, preferred mutations are G131R, D269H, D269K, D269R, R130E, G160K, D218R, G160M, D218Y, D218E, D218K, D218H, I220M, I220H, R149D, R149H, D218F, E155M, T214R, E195R, R191E and D267R. Particularly preferred TRAIL mutants are G160M, D269H, D218Y, R130E and I220M. In particular, the G160M, D269H, D269K, D269R, T214R and E195R mutants are preferred as these are shown herein to have superior selectivity for the death receptor 5.

Some critical residues identified in TRAIL for receptor binding without distinction between DR4 and DR5 (TRAIL-R2) have been identified as Ile 220, Arg 149, Glu 155, Gly 160 and Asp 218. The I220H and I220M mutants both highly increase DR4 binding, and have no effect on DR5 binding. The R149D mutant decreases binding to both the DR4 and DR5 receptors, whilst the R149H and D218R mutants have no effect on binding to either of these receptors. The E155 mutant highly decreases binding to both the DR4 and DR5 receptors; the D218F and D218Y mutants also decrease affinity, although to a lesser extent. Furthermore, the D218Y mutant demonstrates a larger decrease in DR5-affinity than DR4-affinity. Whereas wild type TRAIL has a higher affinity for DR5 than DR4, this preference is lost in the mutant and the overall effect of the D218Y mutation is to shift selectivity towards DR4 (TRAILR1). In the same way, the D218K, D218R, D218E and D218H mutants have superior selectivity for DR4 (TRAIL-R1). Also, it has been shown that different amino acid substitutions in the same position can have a different effect on receptor binding. Some positions, critical for receptor selectivity, due to a different decrease in receptor binding affinity between DR4 (TRAIL-R1) and DR5 (TRAIL-R2) have been identified as Arg 130, Gly 131 and Asp 269. The R130E and G131R mutants decrease binding to DR4 but only slightly decrease binding to DR5. In contrast, the D269H mutant highly decreases binding to DR4. Initial experiments shows that the D269H mutant had no observable effect on binding to DR5, although more recent experiments confirm that in fact this mutant significantly increases binding to DR5. The same receptor binding preferences are demonstrated by variants D269K and D269R.

The skilled reader will be able to identify equivalent positions in other β sheet multimeric cytokine proteins, for example, using multiple alignment programs or manual inspection of related sequences or structures.

Preferably, affinity for receptor is improved for DR4 (TRAIL-R1) or DR5 (TRAIL-R2) over the affinity for the decoy receptors DcR1 (TRAIL-R3) and DcR2 (TRAIL-R4). More preferably still, affinity for DR5 (TRAIL-R2) receptor is improved over affinity for DR4 (TRAIL-R1). Alternatively, affinity for DR4 (TRAIL-R1) receptor is improved over affinity for DR5 (TRAIL-R2).

The above mutations may be introduced in the full length cytokine sequence. Preferably, however, the above mutations are introduced into soluble forms of β sheet multimeric cytokines. For the TRAIL protein, a preferred soluble template into which these mutations may be introduced comprises amino acids 114-281. Equivalent soluble forms of other cytokines will be clear to the skilled reader. However, as the skilled reader will appreciate, variations in this template will very likely retain the properties of this soluble form and show biological activity if additional residues C terminal and/or N terminal of these boundaries in the polypeptide sequence are included. For example, an additional 1, 2, 3, 4, 5, 10, 20 or even 30 or more amino acid residues from the wild-type cytokine sequence, or from a homologous sequence, may be included at either or both the C terminal and/or N terminal of these boundaries, without prejudicing the ability of the polypeptide fragment to fold correctly and exhibit biological activity. Similarly, truncated variants of this template in which one or a few amino acid residues (for example, 1, 2, 3, 4, 5, 10 or more) may be deleted at either or both the C terminus or the N terminus without prejudicing biological activity.

The skilled reader will appreciate that the methods described herein for the alteration of selectivity of a multimeric β sheet cytokine molecule may be combined. In particular, combinations of the selectivity/specificity mutations to give variants with enhanced selectivity. For example, variants with altered selectivity/specificity can be combined with variants with an increased selectivity/specificity. Preferably, the positions of the combined mutations are far enough away from each other so that they cannot make any predictable interaction with each other. As such, both mutations may contribute to selectivity in an independent way.

Such combinations of receptor selective/specific mutations and the variants they encode are included as specific aspects of the present invention. Examples of such molecules include combinations of one or more of the D269H, E195R, T214R, D267R, D269K, D269R and R191E selectivity/specificity mutants, which give variants with enhanced selectivity/specificity. A particularly preferred example is the combination of the R191E mutation with the D267R mutation to give the R191ED267R variant.

The methods described above have been applied to a prototypic example, TRAIL, for purposes of illustration. It will be appreciated that this example is intended as illustrative and is not limiting in any way. Novel mutants of TRAIL have been designed in order to increase binding to the receptor DR4 (TRAIL-R1) relative to the binding to the receptor DR5 (TRAIL-R2). This selectivity/specificity would allow lower concentrations of the variants to be administered, for example in the case of use as a therapeutic, than would be used with respect to wild-type TRAIL.

The skilled reader will appreciate that the methods described herein, for the stabilisation of a multimeric β sheet cytokine molecule, and for the alteration of selectivity of a multimeric β sheet cytokine molecule, may be combined.

In particular, combinations between the stability variants described above can be made, giving variants with enhanced stability and altered selectivity/specificity. Such combinations of stable and receptor selective/specific cytokine molecules are included as specific aspects of the present invention. Examples of such molecules include any one of the TRAIL M1, M2, M3 and C1 mutants, combined with one or more of the D269H, E195R, T214R, D269HE195R, D269HT214R, D269K, D269R, R191ED267R, G160M, D218Y, D218H, D218K, D218R, R130E and I220M selectivity/specificity mutants, which give variants with enhanced stability and altered selectivity/specificity. A particularly preferred example is the selective and stable variant D269HM1 which has increased selectivity/specificity for DR5 (TRAIL-R2) and increased stability when compared to wild type TRAIL.

Conventional experimental methodologies may be used to supplement the largely computational approach that is outlined above. For example, once amino acid substitutions have been identified, these substitutions should be produced experimentally using site-directed mutagenesis and then tested for stability or selectivity/specificity and for retention of biological activity. Identified molecules can be further mutated using conventional techniques of molecular evolution, to develop more specific therapeutic lead molecules. In the case of molecular evolution, one particularly useful technology is phage display, which when coupled with an effective biopanning strategy, and when integrated with rational design methodologies, should result in rapid molecular evolution of novel therapeutics.

The invention also provides purified nucleic acid molecules which encode a mutant β sheet cytokine as described above. Further aspects of the invention include vectors, such as expression vectors, that contain such nucleic acid molecules, along with host cells transformed with these vectors.

In an further aspect, the invention provides a β sheet multimeric cytokine whose sequence has been altered by a method according to any one of the aspects of the invention described above, or a nucleic acid molecule encoding such a molecule, or a vector containing a nucleic acid molecule as described, for use in the therapy or diagnosis of a disease in which cytokines are implicated. This aspect of the invention includes a method for the treatment of such a disease, comprising administering to a patient, a cytokine, nucleic acid or vector as described above, in a therapeutically-acceptable amount. Such molecules may also be used in diagnosis, for example, by assessing the level of expression or activity of a gene or protein (such as an over-expressed receptor) in tissue from said patient and comparing said level of expression or activity to a control level, wherein a level that is different to said control level is indicative of disease.

A further aspect of the invention may comprise a pharmaceutical composition comprising a mutant cytokine, nucleic acid or vector as described above, in conjunction with a pharmaceutically-acceptable carrier.

A still further aspect of the invention may comprise transgenic or knockout non-human animals that have been transformed to express a mutant cytokine as described above. Such transgenic animals provide useful models for the study of disease and may also be used in screening regimes for the identification of compounds that are effective in the treatment or diagnosis of disease.

Importantly, the generation of mutant cytokine molecules such as those described above allows for the design of screening methods capable of identifying compounds that are effective in the treatment and/or diagnosis of diseases in which these cytokines are implicated. The interacting domains of these molecules have an intrinsic propensity to initiate signalling pathways associated with the modulation of cancer and other chronic diseases, including autoimmune disease, and are starting points for drug design. Such screening methods are included as aspects of the present invention.

Various aspects and embodiments of the present invention will now be described in more detail by way of example. It will be appreciated that modification of detail may be made without departing from the scope of the invention.

BRIEF DESCRIPTION OF DRAWINGS

FIG. 1. A) Side view of the TRAIL trimeric complex, showing the three monomers in red, blue and green. B) Top view of the same complex but viewed along the longitudinal axis, depicting the different sets used for design. Structure figures were generated using MOLMOL (Koradi et al., *J. Mol. Graph.* 14, 51-32 (1996)).

FIG. 2. Binding of wild-type TRAIL (closed circle), M1 (closed box) and M2 (open circle) to DR5 (TRAIL-R2) ( . . . ) and DR4 (TRAIL-R1) (–) receptors.

Figure 3:
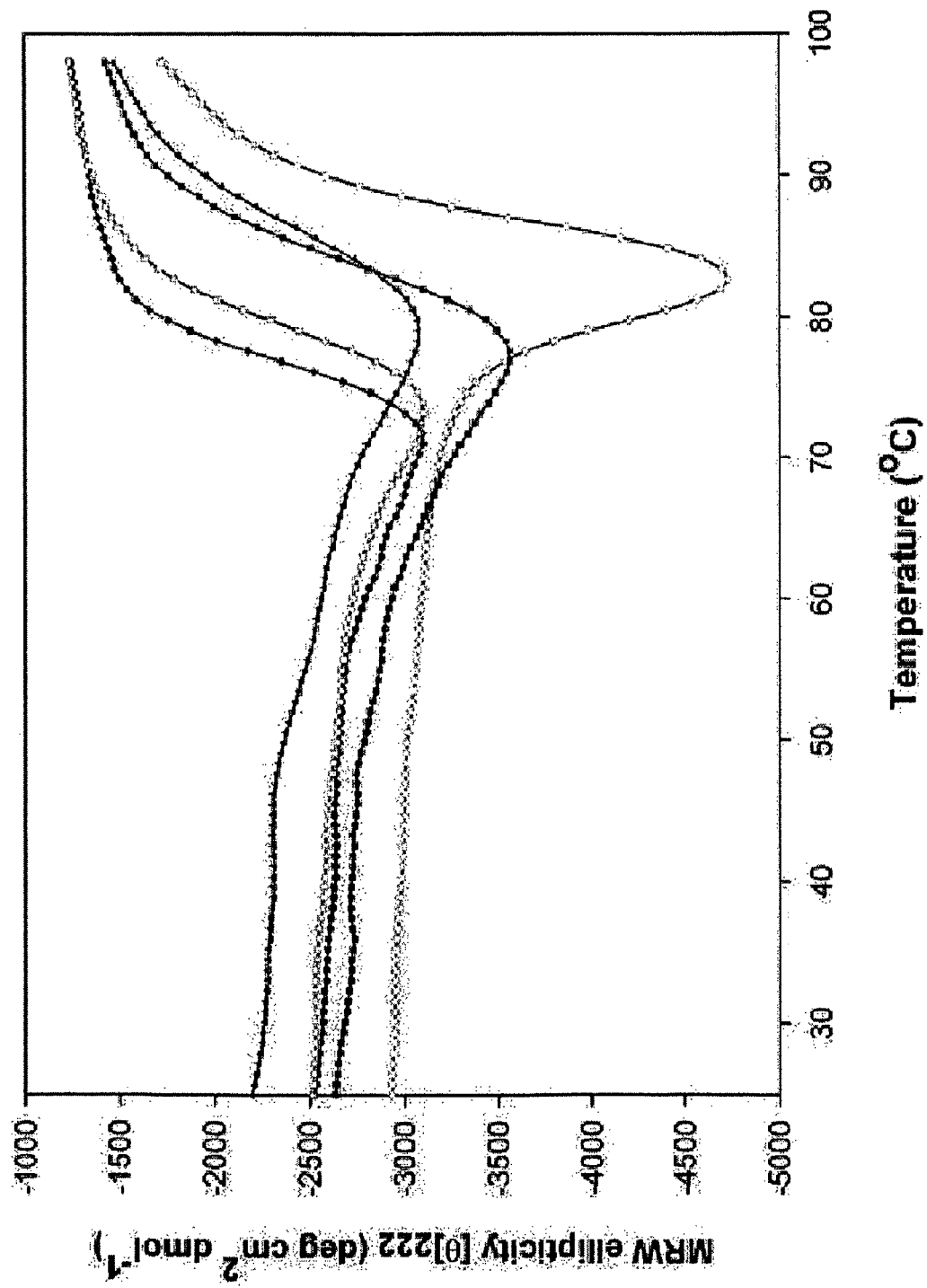

FIG. 3. Thermal denaturation profiles of wild-type TRAIL (closed circle), M1 (closed box), M2 (open circle), M3 (open box) and C1 (closed triangle).

Figure 4:
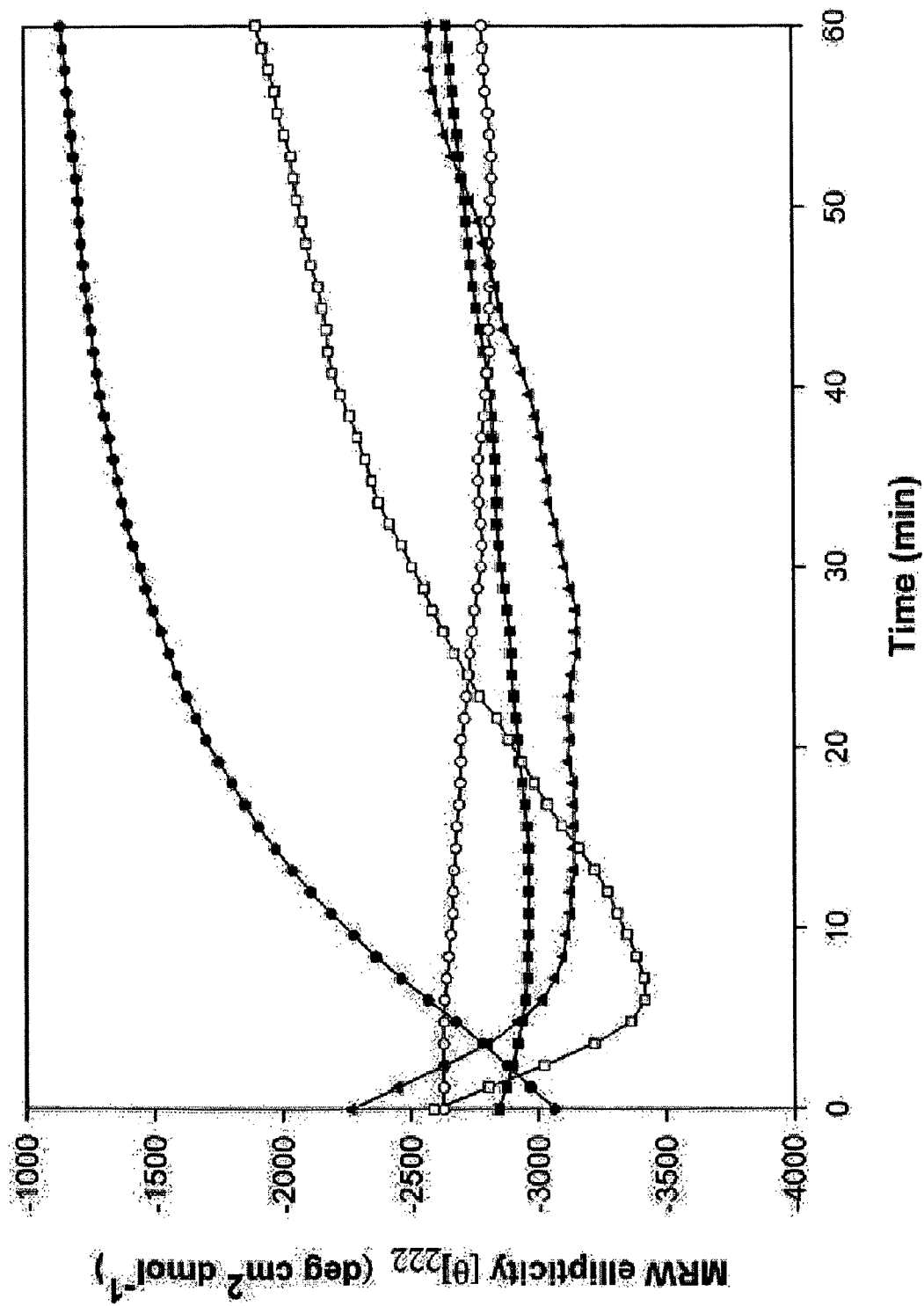

FIG. 4. Stability of wild-type TRAIL (closed circle), M1 (closed box), M2 (open circle), M3 (open box) and C1 (closed triangle) at 73° C. for 60 min.

Figure 5:
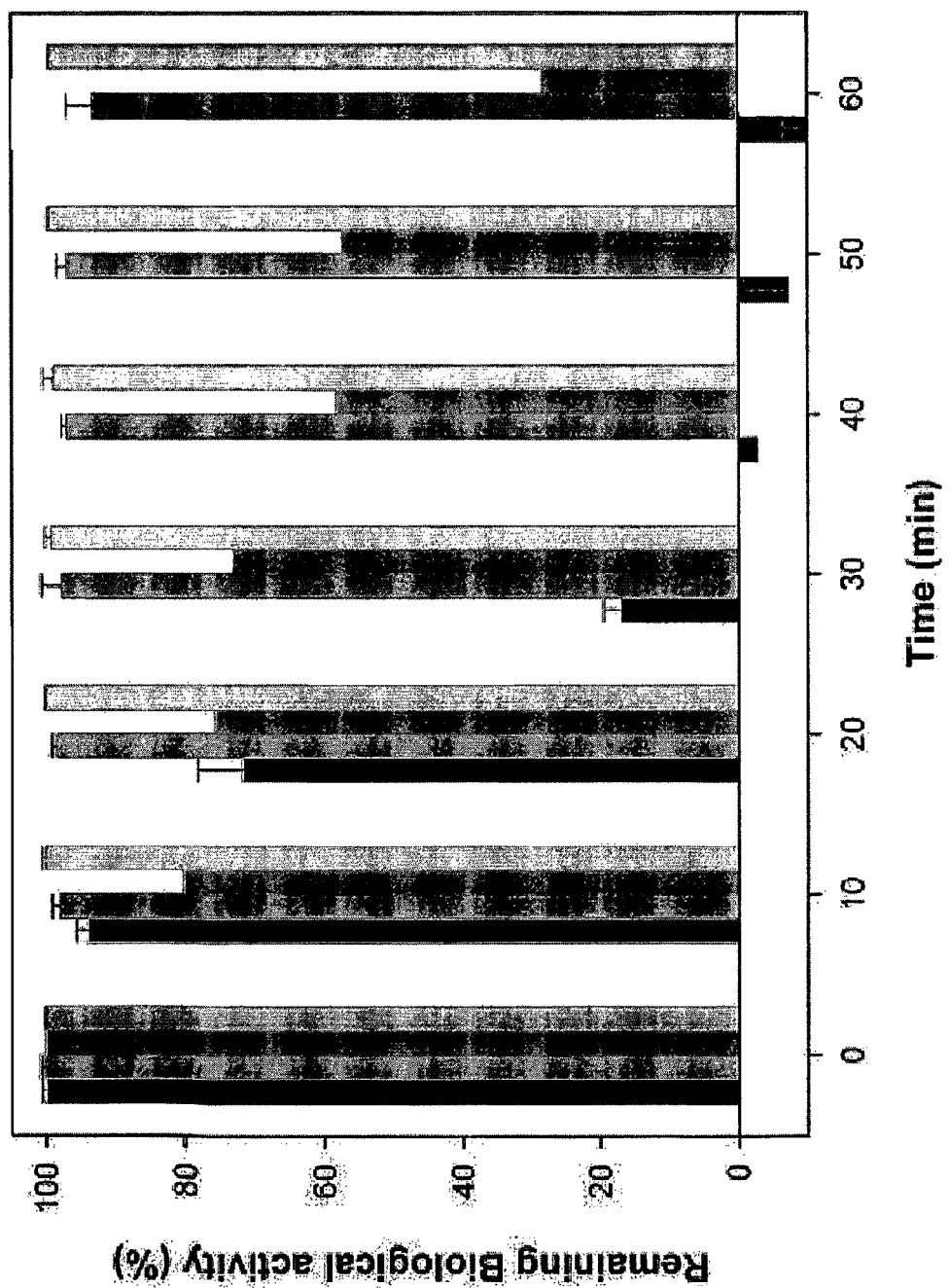

FIG. 5. Remaining biological activity of wild-type TRAIL, M1, M3 and C1 (from left to right) upon incubation at 73° C. during 60 min.

Figure 6:
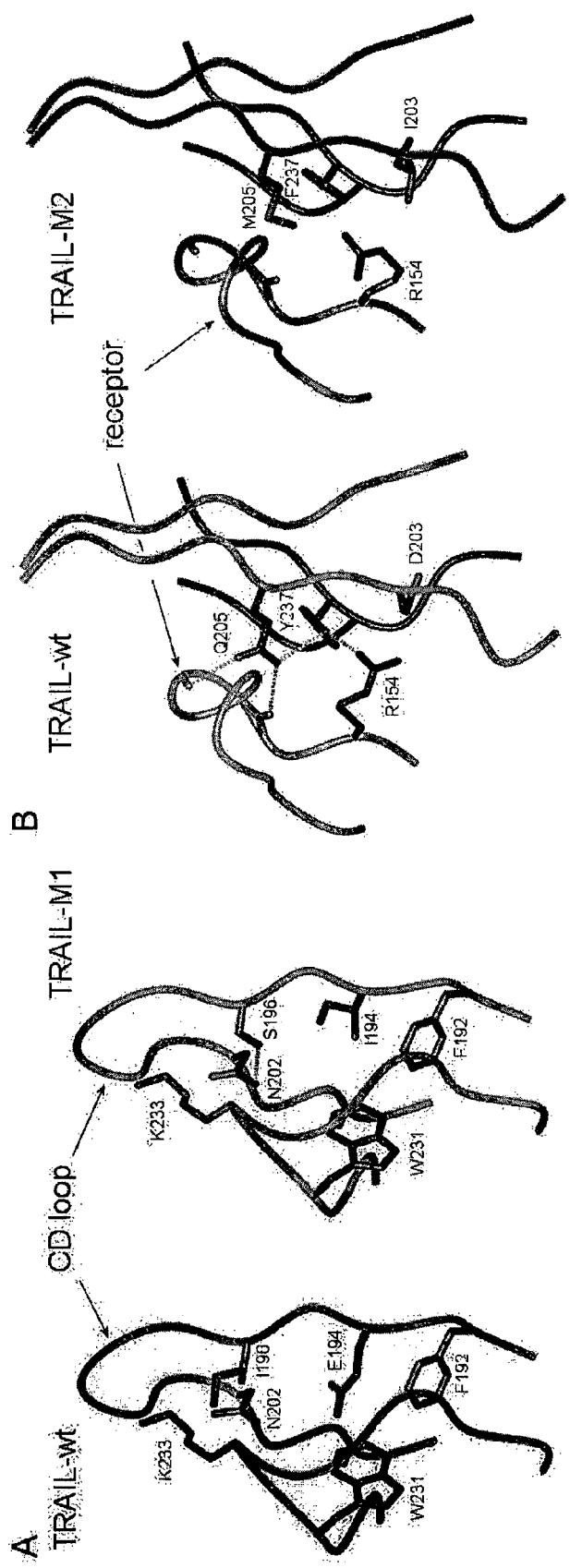

FIG. 6. A) Comparison, between wild-type TRAIL and M1, of the local environment around residues 194 and 196. B) Comparison between wild-type TRAIL and M2. Backbones of the two adjacent monomers are in green and blue, respectively, and the backbone of the DR5 (TRAIL-R2) receptor is in grey. Hydrogen bond interactions are depicted in dashed green lines.

Figure 7:
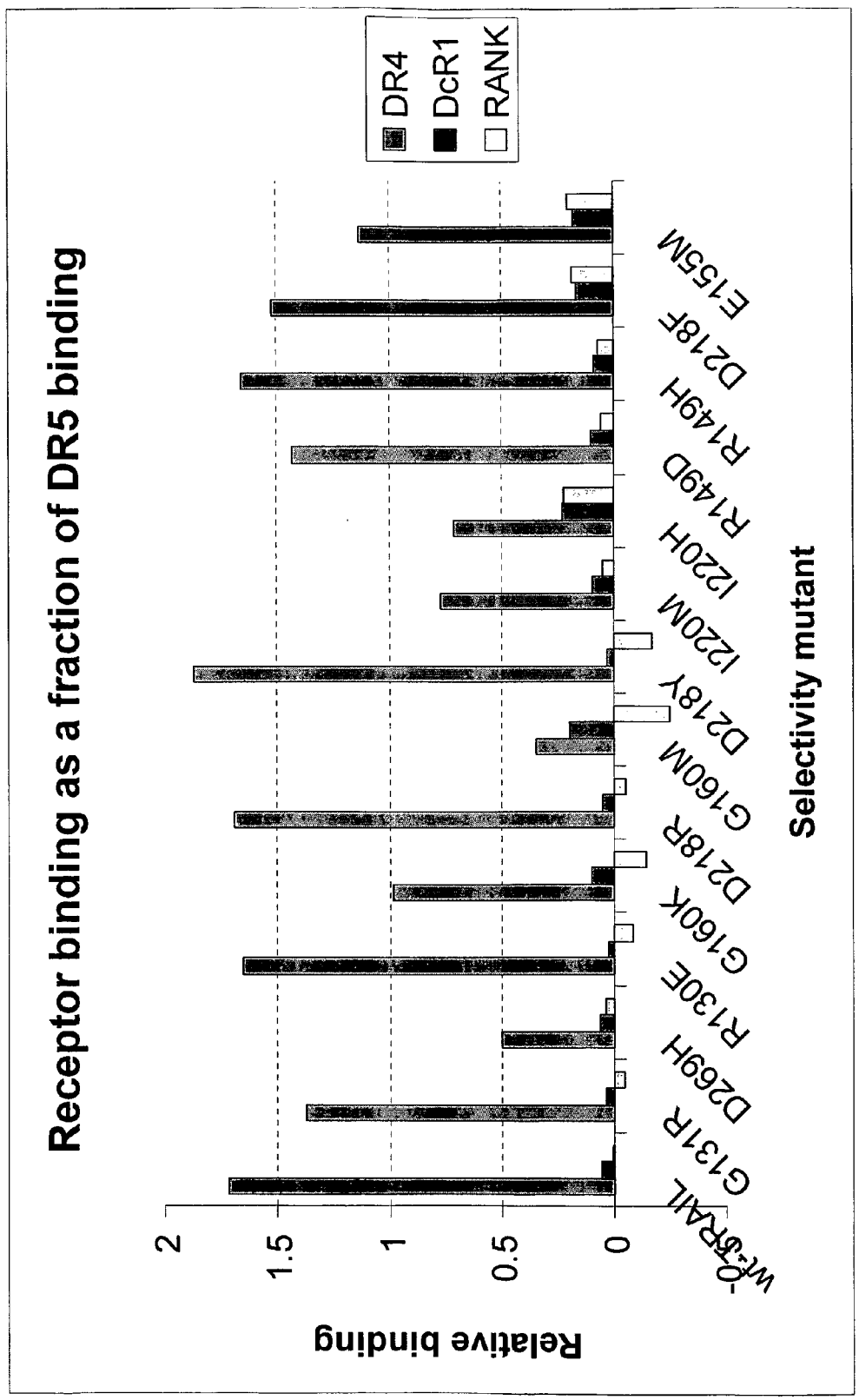

FIG. 7. Receptor binding as a fraction of DR5 (TRAIL-R2) binding.

Figure 8:
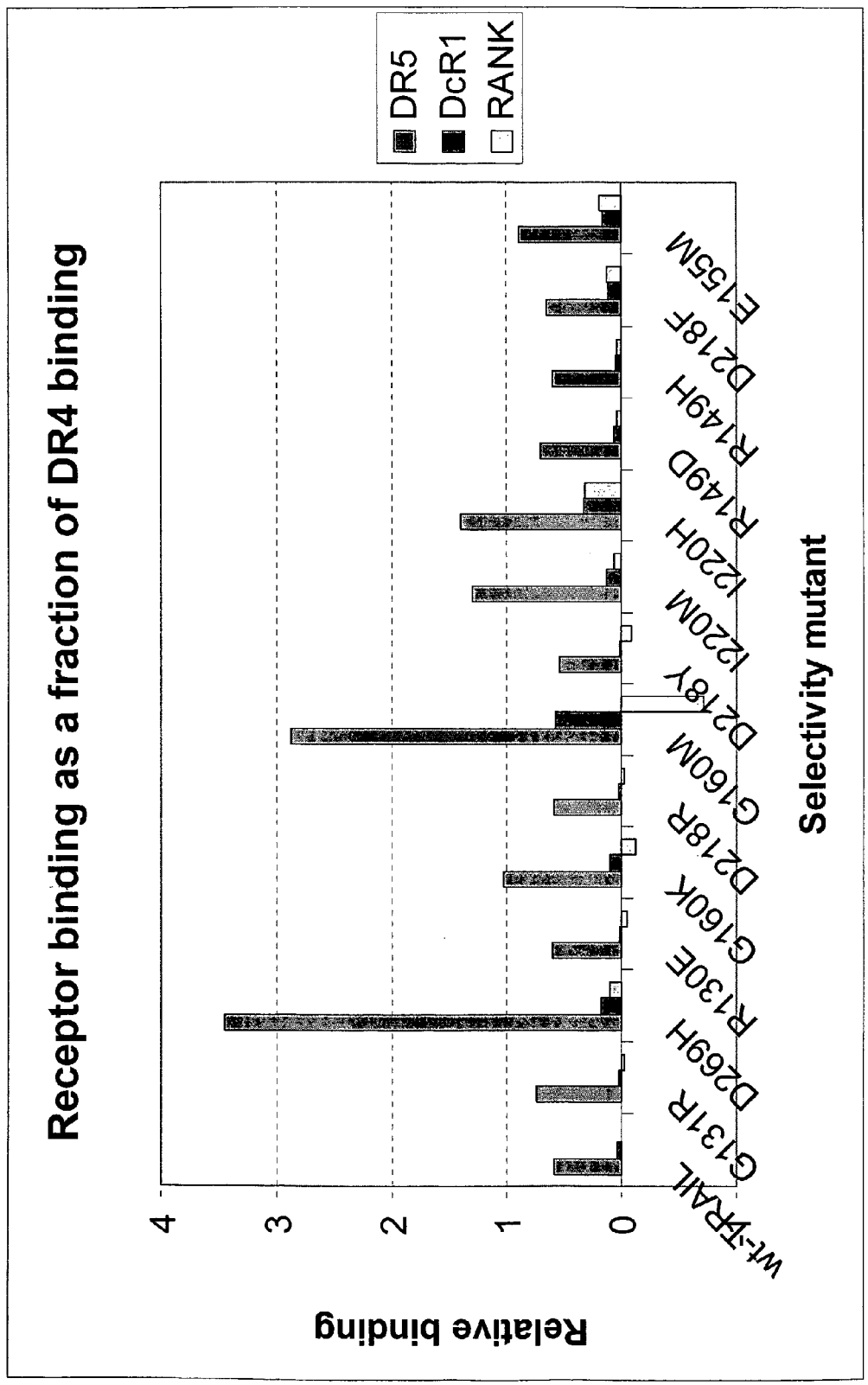

FIG. 8. Receptor binding as a fraction of DR4 (TRAIL-R1) binding.

Figure 9:
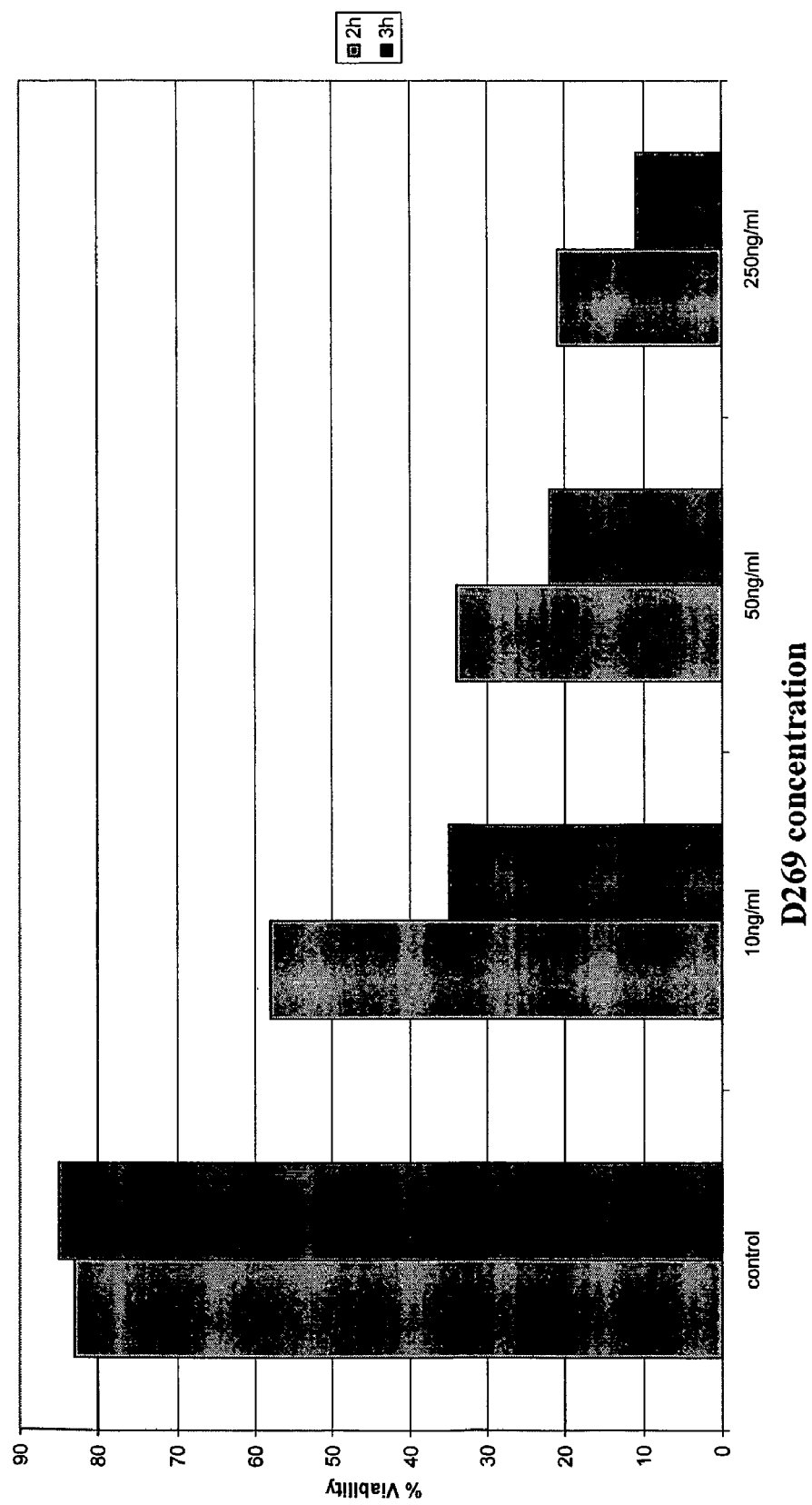

FIG. 9. Cytotoxic potential of D269H—Annexin V staining.

Figure 10:
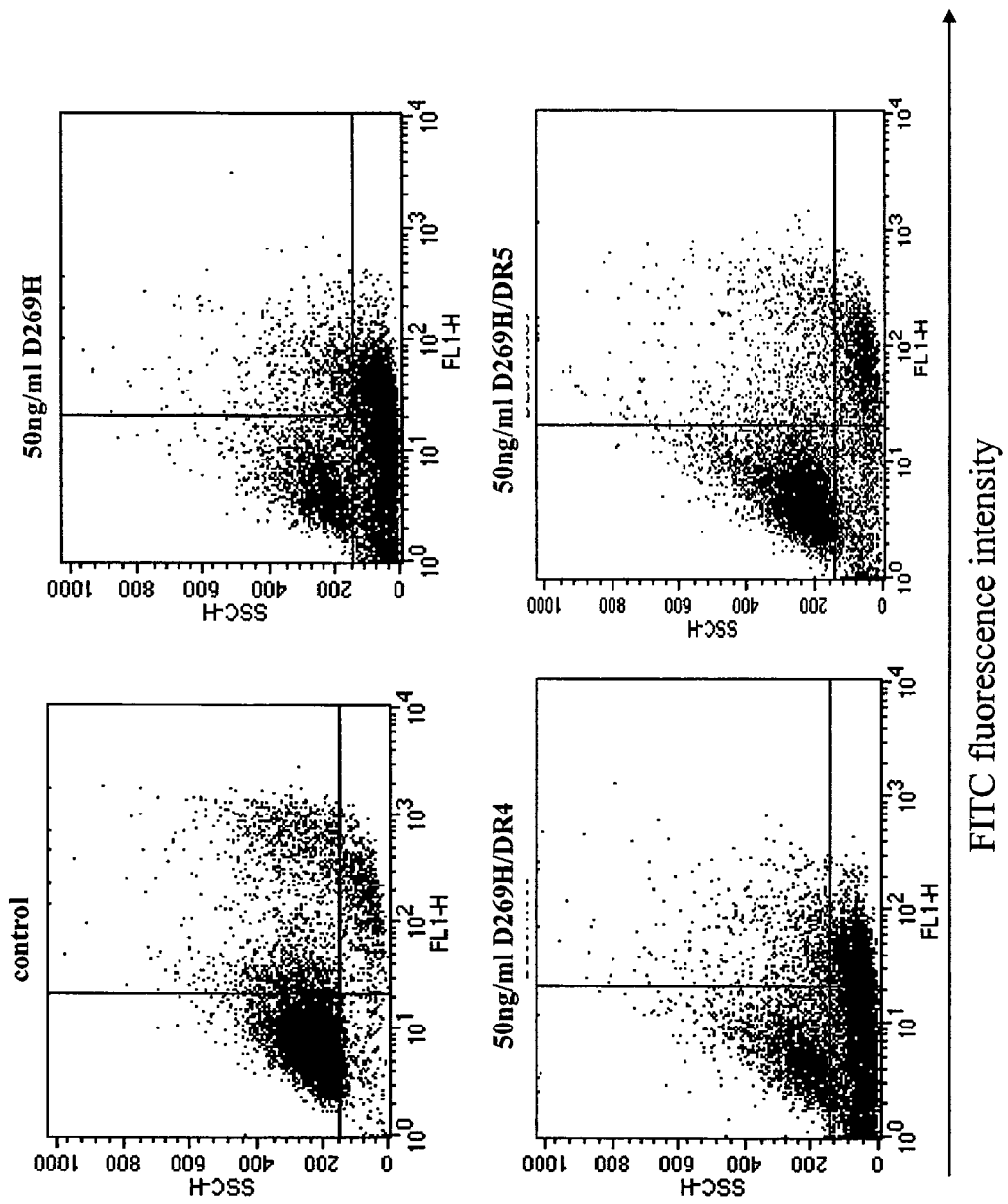

FIG. 10. Testing TRAIL receptor specific killing of D269H mutant—Annexin V staining.

Figure 11:
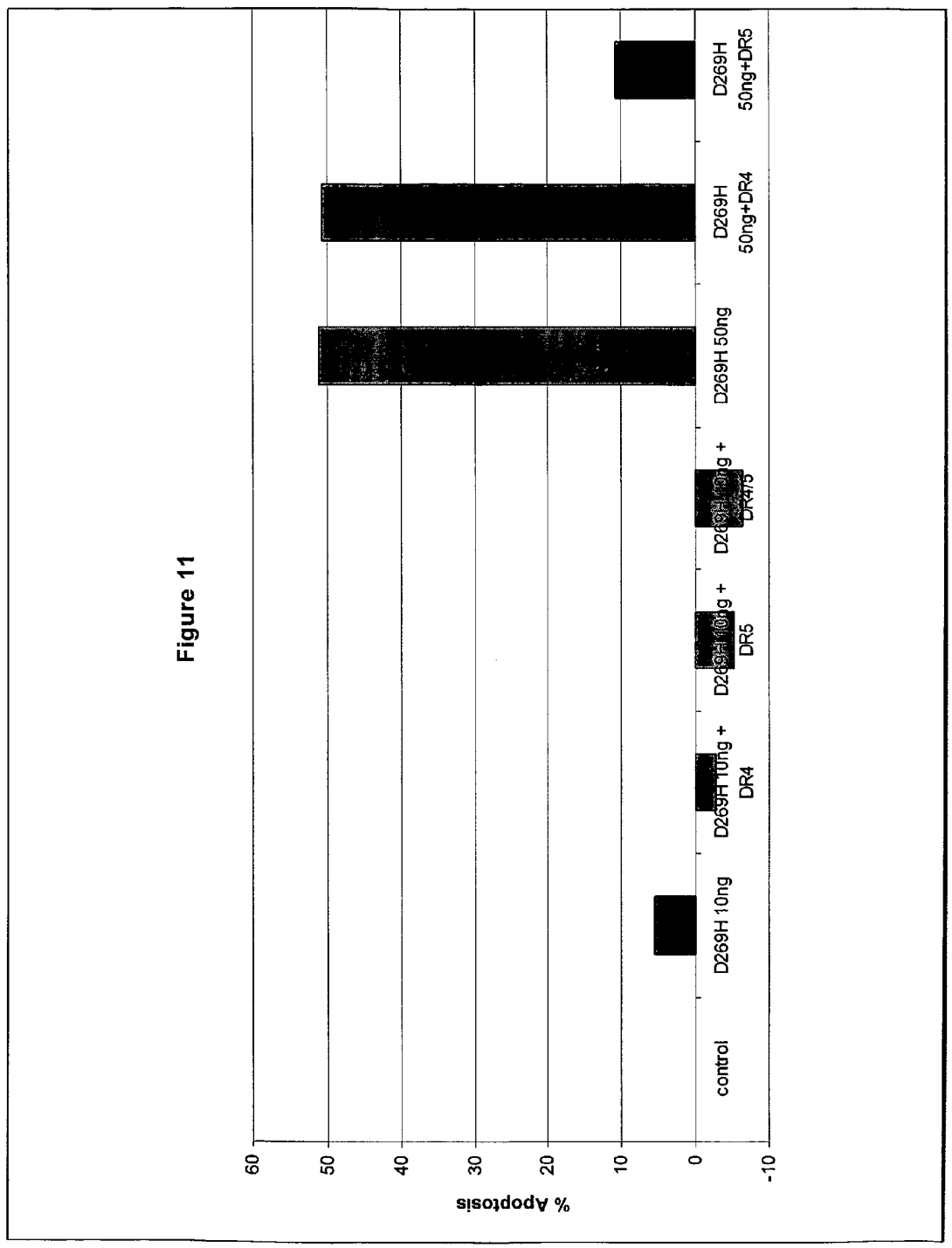

FIG. 11. DR5 (TRAIL-R2) selective killing by D269H—Annexin V staining.

Figure 12:
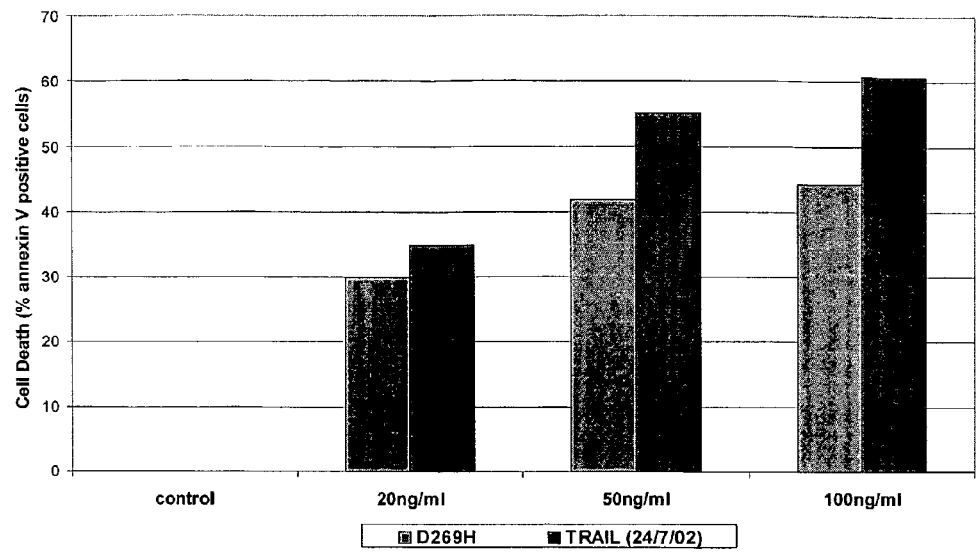
Figure 12:
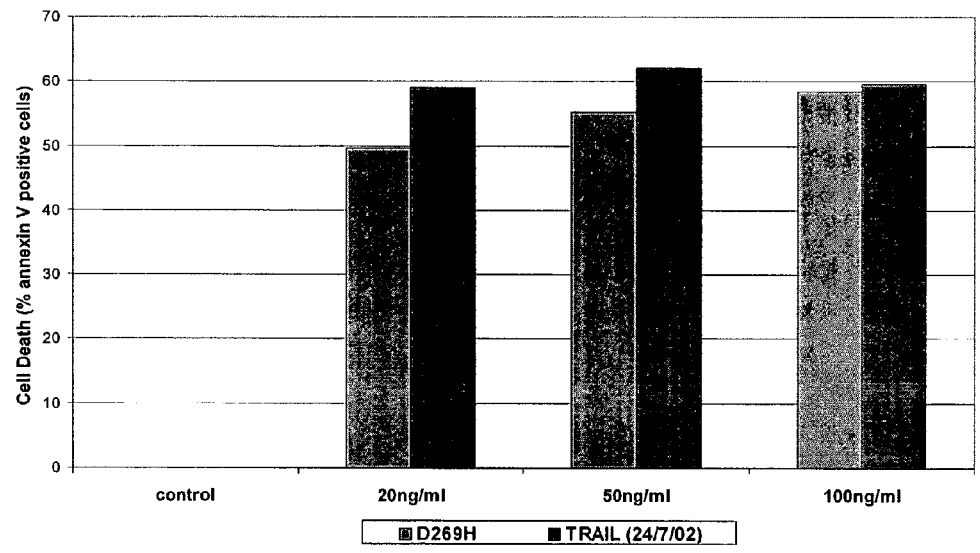

FIG. 12. D269H and TRAIL have comparable cytotoxic potential. A, cells treated with TRAIL and D269H for 2 h; B cells treated for 3 h (B). The graph shows a representative of 2 independent experiments.

Figure 13:
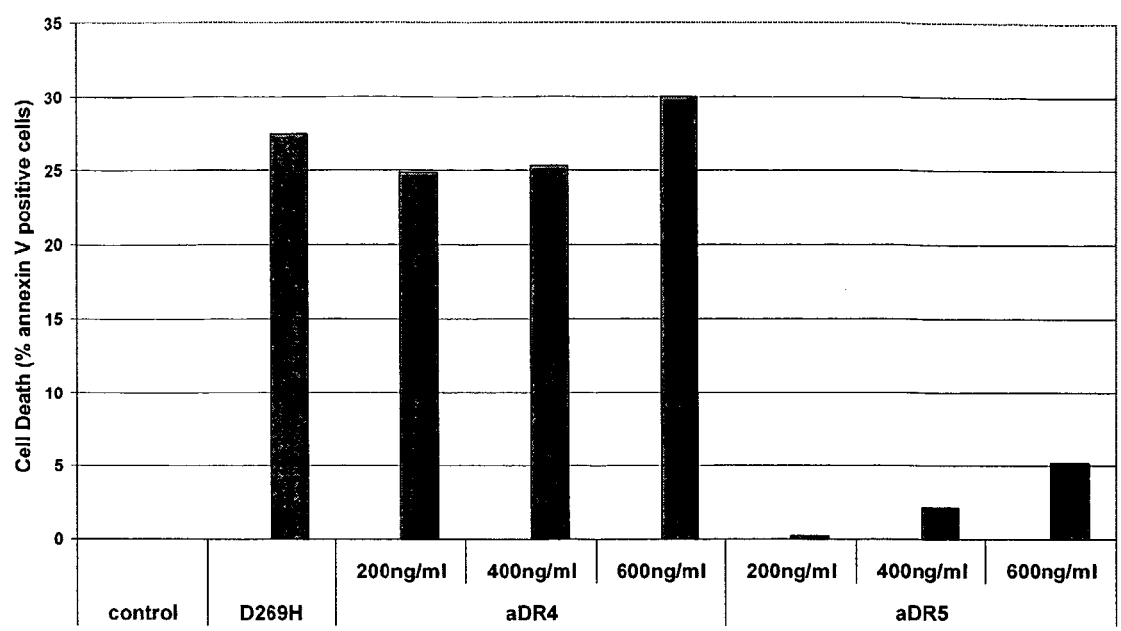

FIG. 13. Neutralisation of DR5, but not DR4 was able to block cell death induced by D269H.

Figure 14:
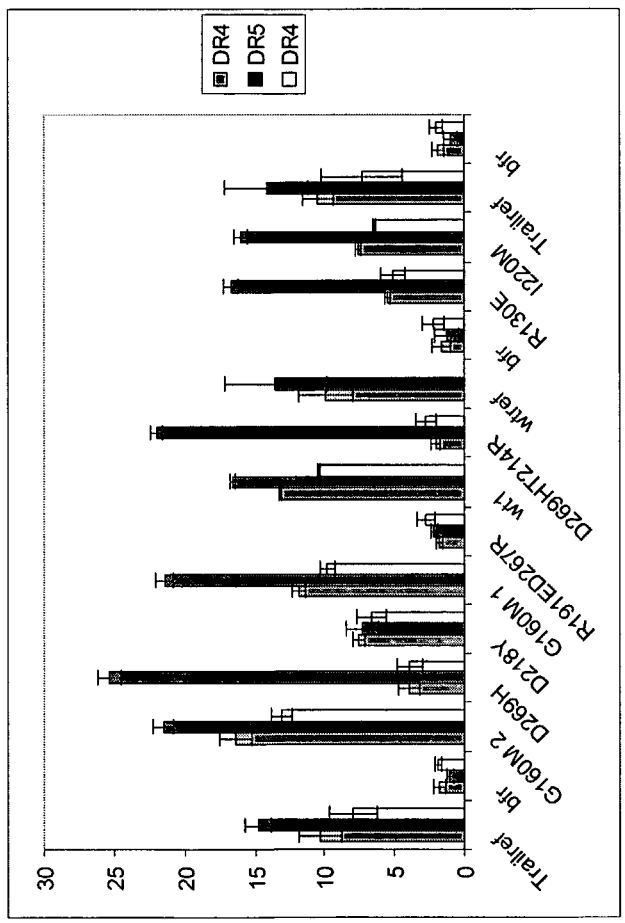

FIG. 14. Receptor binding to DR4 (TRAIL-R1) Fc and DR5 (TRAIL-R2) Fc of purified wild-type TRAIL (wt1) and various purified mutants at a concentration of 60 nM.

Figure 15:
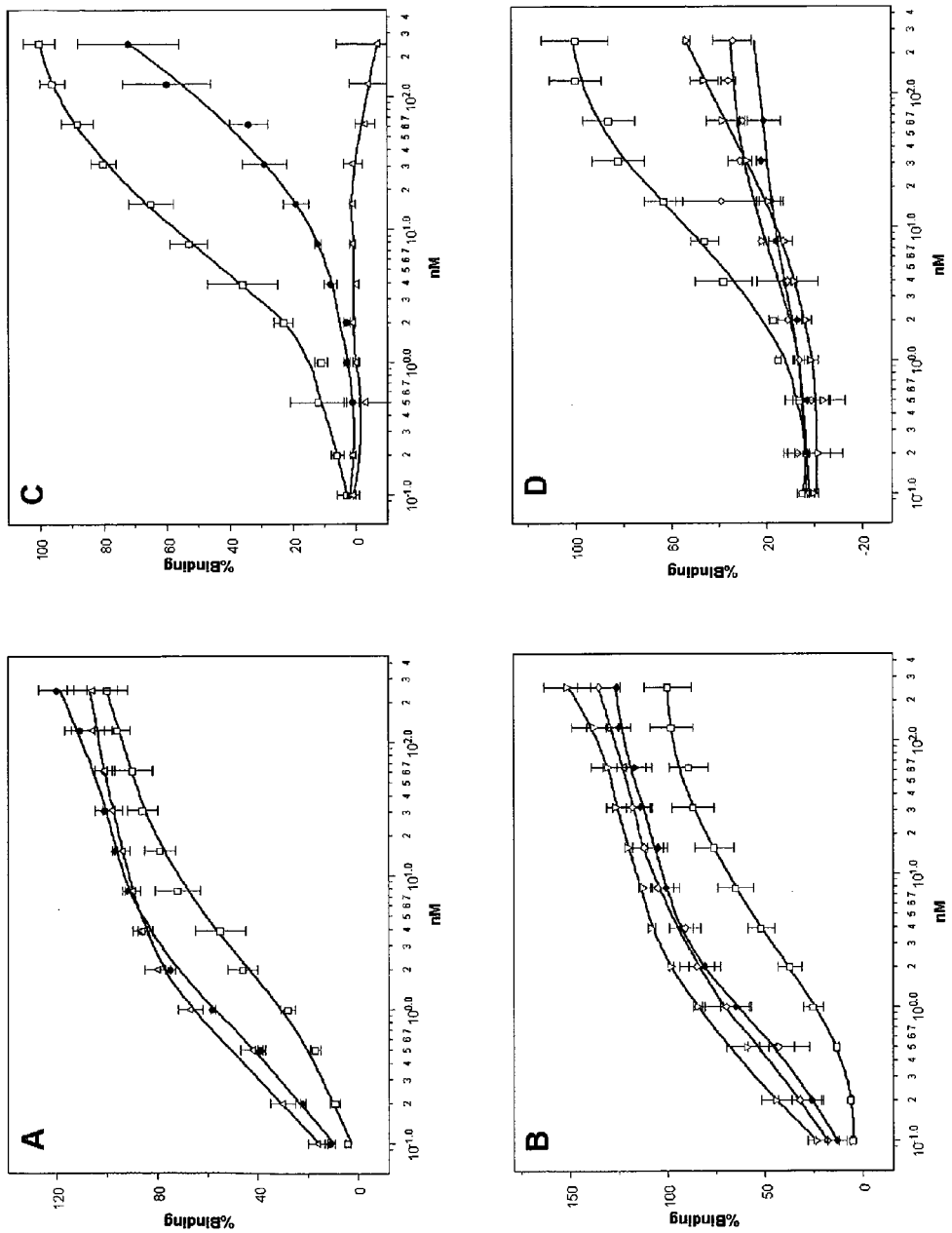

FIG. 15. Panel A & B: Binding to DR5 (TRAIL-R2) Fc; Panel C & D: Binding to DR4 (TRAIL-R1) Fc. Wild-type TRAIL: box (open); D269H: circle (closed); D269HT214R: Triangle (Up&Open); D269K: diamond (closed); D269R: diamond (open); D269HE195R: Triangle (down&Open)

Figure 16:
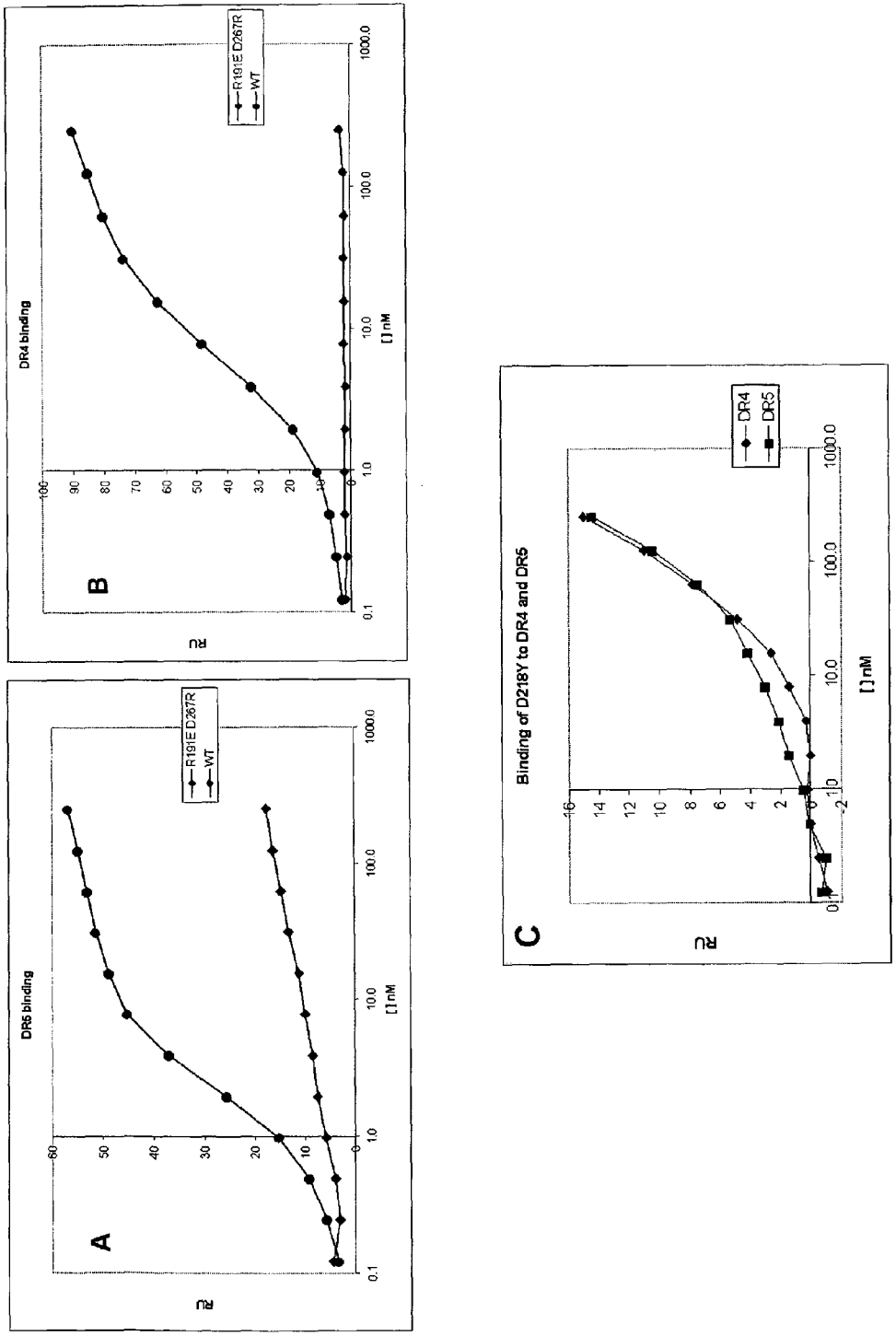

FIG. 16. Panel A: Binding of wild-type TRAIL (wt) and R191ED267R to DR5 (TRAIL-r2) Fc; Panel B: Binding of wild-type TRAIL (wt) and R191ED267R to DR4 (TRAIL-R1) Fc; Panel C: Binding of D218Y to DR4 (TRAIL-R1) Fc and DR5 (TRAIL-R2) Fc.

Figure 17:
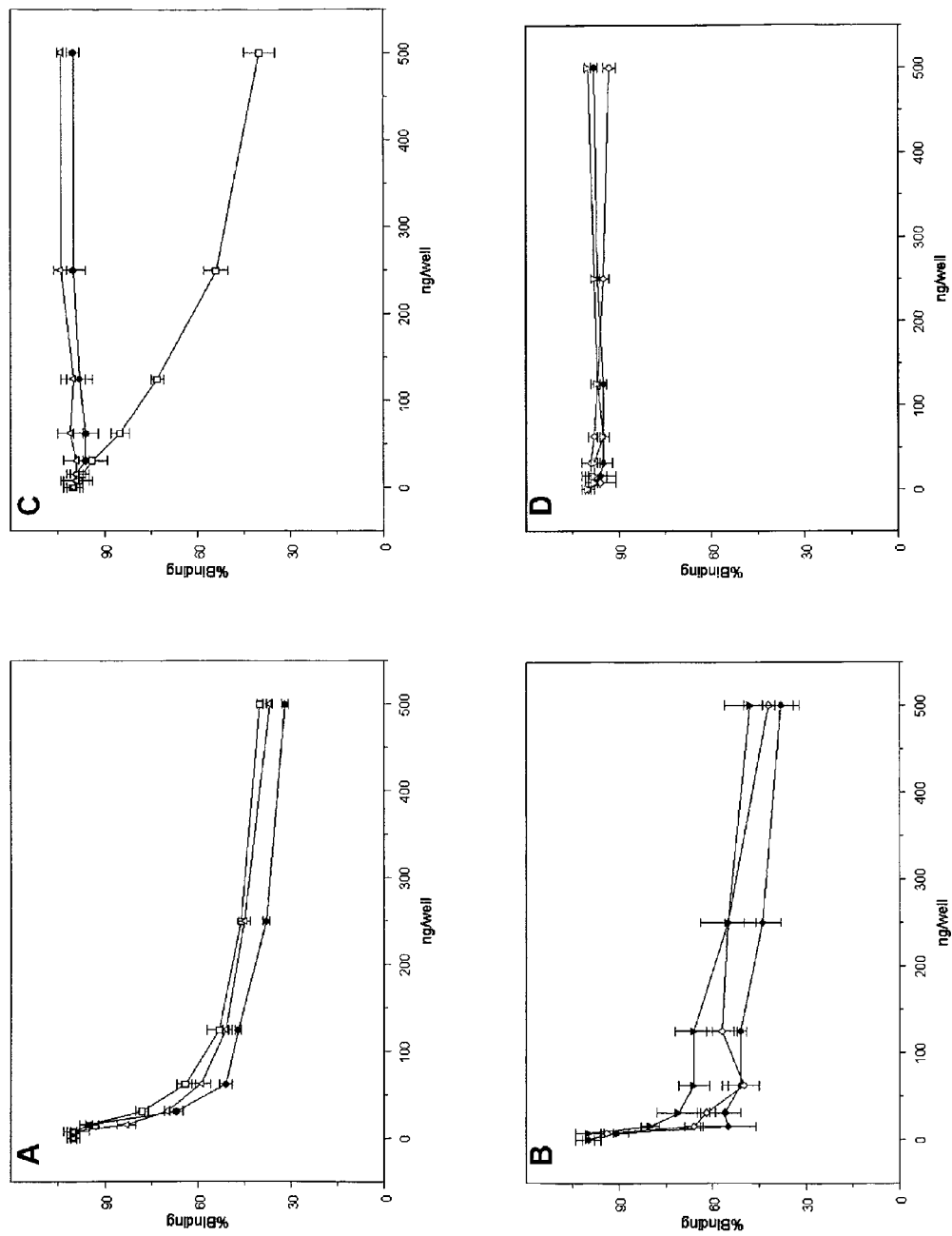

FIG. 17. Competition ELISA. Panel A&B: Titration (blocking) with DR5 (TRAIL-R2) Fc; Panel C&D: Titration (blocking) with DR4 (TRAIL-R1) Fc. Wild-type TRAIL: box (open); D269H: circle (closed); D269HT214R: Triangle (Up&Open); D269K: diamond (closed); D269R: diamond (open); D269HE195R: Triangle (down&Open)

Figure 18:
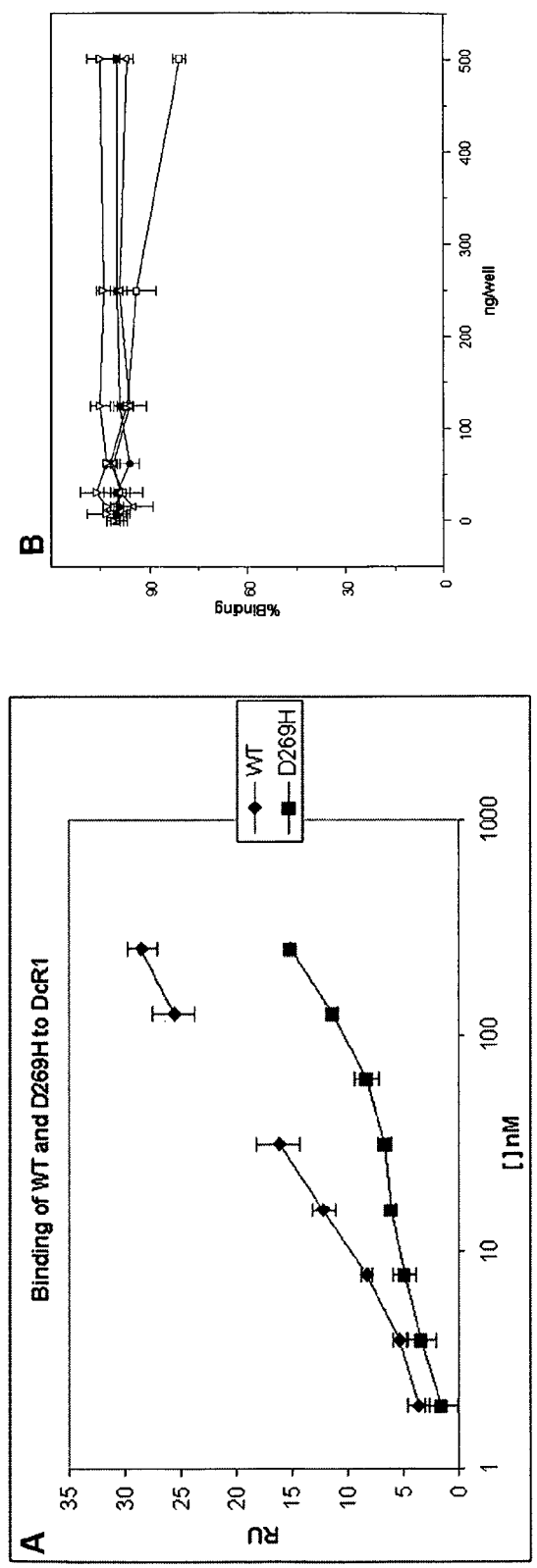

FIG. 18. Panel A: Receptor binding of wild-type TRAIL and D269H to DcR1 (TRAIL-R3) Fc: Panel B: Competition ELISA. Titration with DcR1 (TRAIL-R3) Fc. Wild-type TRAIL: box (open); D269H: circle (closed); D269HT214R: Triangle (Up&Open); D269HE195R: Triangle (down&Open)

Figure 19:
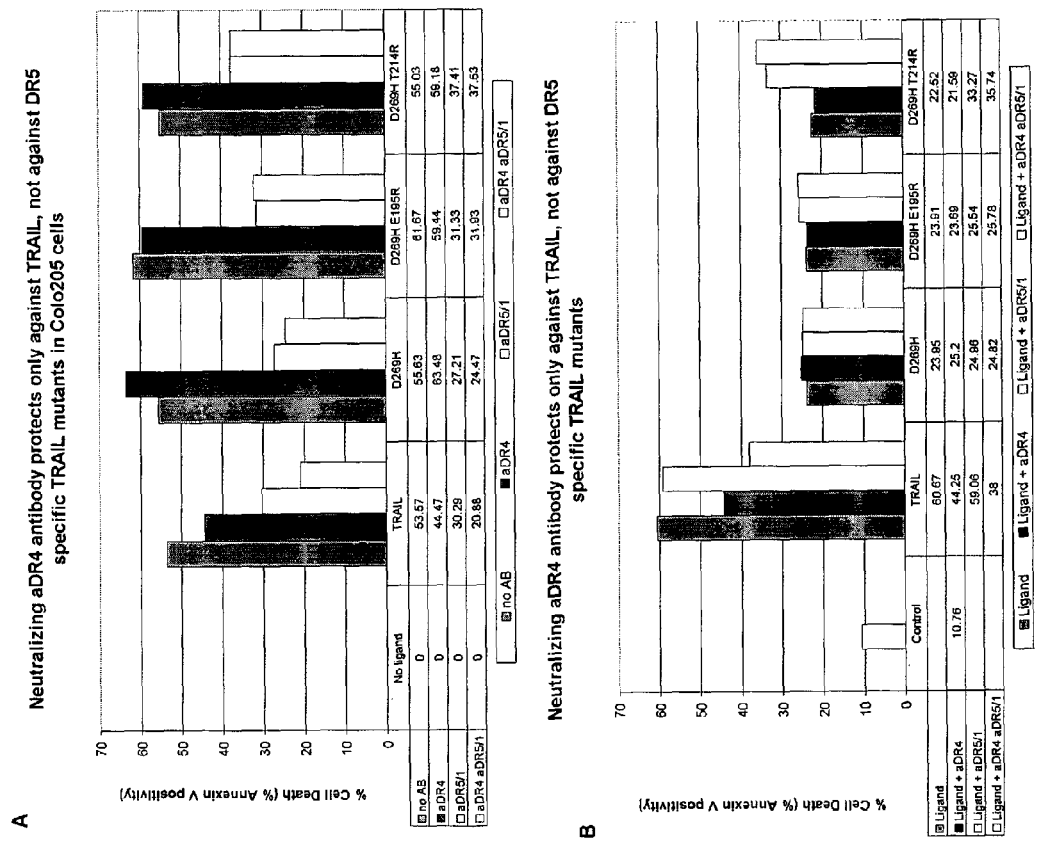

FIG. 19. Panel A: Induction of Apoptosis in Colo205 cells by wild-type TRAIL and D269H, D269HE195R and D269HT214R mutants and blocking of apoptosis with neutralizing anti-DR4 and anti-DR5 antibodies. Panel B: Induction of Apoptosis in ML-1 cells by wild-type TRAIL and D269H, D269HE195R and D269HT214R mutants and blocking of apoptosis by addition of neutralizing anti-DR4 and/or anti-DR5 antibodies.

Figure 20:
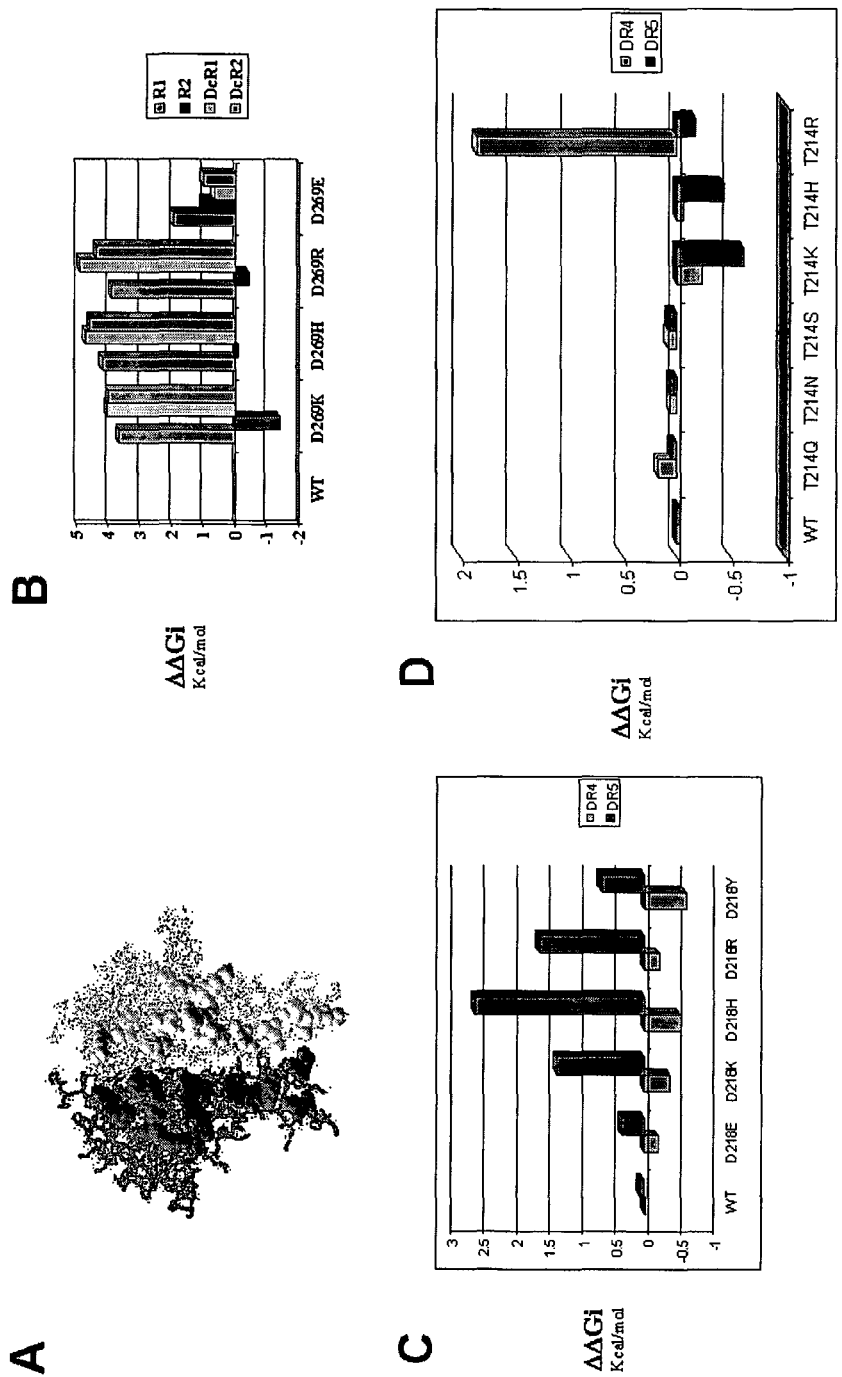

FIG. 20. A: Side view of TRAIL receptor-binding interface formed by two monomer units (third monomer, not involved in this receptor-binding interface, stays behind these two monomers; receptor binds in front of them. They have been removed for a better view of the interface). TRAIL residues highlighted with Van der Waals radius were the selected residues for the in silico mutagenesis scanning. B: Most significant predicted shifts in TRAIL-receptor binding affinity of single mutants in position 269. D269E is added for comparison. C: Most significant predicted shifts in TRAIL-receptor binding affinity of single mutants in position 218. D: Predicted shifts in TRAIL-receptor binding affinity of single mutants in position 214. (Panel B-D: predicted shifts are calculated using PERLA and Fold-X).

FIG. 21. Panel A: Binding of wild-type TRAIL (wt) and D269HM1 to DR5 (TRAIL-R2) Fc; Panel B: Binding of wild-type TRAIL (wt) and D269HM1 to DR4 (TRAIL-R1) Fc. Panel C: Remaining biological activity of wild-type TRAIL (wt) and D269HM1 upon incubation at 73° C. for 50 min. Biological activities are calculated relative to the value observed at 0 min.

EXAMPLES

Example 1

Stable TRAIL Proteins

Methods

All reagents were of analytical grade unless specified otherwise. Isopropyl-β-D-1-thiogalactoside (IPTG), ampicillin and dithiotreitol (DTT) were from Duchefa. Chromatographic columns and media were from Amersham Biosciences. Restriction enzymes used were purchased from New England Biolabs.

All other chemicals were from Sigma.

Computational Design of Mutants

A detailed description of the protein design algorithm, PERLA, is available elsewhere (Lacroix, E. Protein design: a computer based approach, Ph.D. thesis. (U. Libre de Bruxelles, 1999)) (http://ProteinDesign.EMBL-Heidelberg.DE) and its use has been previously described (see, for example, Ventura et al., *Nat. Struct. Biol.* 9, 485-493 (2002). In the case of oligomeric proteins like TRAIL, protein design with PERLA requires the following steps: Firstly, residues of a monomer that could establish specific interactions with the contiguous monomer must be identified and selected. Secondly, side chains that contact the residues to be mutated, must be identified to allow side chain movements that are necessary to accommodate the new residues introduced by the algorithm. PERLA automatically selects these residues based on a geometrical approach that takes Ca-Ca distances and the angle between Ca-Cβ vectors into consideration. Thirdly, the algorithm places the amino acid repertoire at each position selected from a set of naturally occurring amino acids in a multiple sequence alignment of the TNF ligand family, and eliminates those side chain conformations and amino acids that are not compatible with the rest of the structure. Fourthly, all possible pair-wise interactions are explored to eliminate those combinations that are less favourable. Finally, an output of sequences and PDB coordinates corresponding to the best calculated solution (in terms of energy) is produced. The resultant PDB files containing the mutations were energy minimized using GROMOS 43B1 as implemented in Swiss-PdbViewer v3.7b2 (Guex, & Peitsch. *Electrophoresis* 18, 2714-2723 (1997))), and evaluated by FOLD-X (http://fold-x.embl-heidelberg.de). The final energies of the models are compared to the reference, wild-type TRAIL structure and expressed as ?? G (kcal mol$^{-1}$).

Cloning and PCR cDNA corresponding to human soluble TRAIL (aa 114-281) was cloned in pET15B (Novagen) using NcoI and BamHI restriction sites. The N-terminal sequence encoding a His-tag and protease recognition site was therefore removed. Mutants were constructed by PCR using the Quick Change Method (Stratagene) or a modified megaprimer method (Picard et al., *Nucleic Acids Res.* 22, 2587-2591 (1994)). The polymerase used was Pfu Turbo supplied by Stratagene. Purified mutagenic oligonucleotides were obtained from Invitrogen. Introduction of mutations was confirmed by DNA sequencing.

Expression and Purification of Wild-type TRAIL and Mutants

The wild-type TRAIL and TRAIL mutant constructs were transformed to *Escherichia Coli* BL21 (DE3) (Invitrogen). Wild-type TRAIL and M1 were grown at a 5 l batch scale in a 7.5 l fermentor (Applicon) using 4×LB medium, 1% (w/v) glucose, 100 µg/ml ampicillin and additional trace elements. The culture was grown to mid-log phase at 37° C., 30% oxygen saturation and subsequently induced with 1 mM IPTG. ZnSO$_4$ was added at a concentration of 100 µM to promote trimer formation. Temperature was lowered to 28° C. and the culture was grown until stationary phase. Other mutants were grown in shake flasks at a 1 l scale at 250 rpm, using a similar protocol. Protein expression was induced when the culture reached OD$_{600}$ 0.5 and induction was continued for 5 h. In this case, the medium used was 2×LB without additional trace elements.

The isolated pellet was resuspended in 3 volumes extraction buffer (PBS pH 8, 10% (v/v) glycerol, 7 mM β-mercapto-ethanol). Cells were disrupted using sonication and extracts were clarified by centrifugation at 40,000 g. Subsequently, the supernatant was loaded on a nickel charged IMAC Sepharose fast-flow column and wild-type TRAIL and TRAIL mutants were purified as described by Hymowitz (Hymowitz et al., *Biochemistry* 39, 633-640 (2000)) with the following modifications: 10% (v/v) glycerol and a minimal concentration of 100 mM NaCl were used in all buffers. This prevented aggregation during purification. After the IMAC fractionation step, 20 µM ZnSO$_4$ and 5 mM of DTT (instead of β-mercapto-ethanol) was added in all buffers. Finally, a gelfiltration step, using a Hiload Superdex 75 column, was included. Purified proteins were more than 98% pure as determined using a colloidal coomasie brilliant blue stained SDS-PAGE gel. Purified protein solutions were flash frozen in liquid nitrogen and stored at −80° C.

CD Spectroscopy

CD spectra were recorded on a Jasco J-715 CD spectrophotometer (Jasco Inc.) equipped with a PFD350S Peltier temperature control unit (Jasco Inc.). Rectangular quartz cuvettes with a pathlength of 0.2 cm were used. Protein samples were dialyzed against PBS pH 7.3 and adjusted to a final concentration of 100 µg/ml. Wavelength spectra were recorded between 250-205 nm using a 0.2 nm stepsize and 1 nm band-width at 25° C. Temperature scans from 25-98° C. were performed at 222 nm with a scan rate of 40° C./h. Thermal decay measurements were performed at 73° C. for 1 h at 222 nm.

Bioactivity of TRAIL Mutants In Vitro

Bioactivity of wild-type TRAIL and TRAIL mutants was determined using a viability assay according to the manufacturer's instructions (Celltiter Aqueous One, Promega). Colo205 human colon carcinoma cells (ATCC number CCL-222) were cultured in RPMI 1640 Glutamax containing 10% heat inactivated fetal calf serum and 100 units/ml Penicillin-Streptomycin. All reagents were supplied by Invitrogen. A concentration series of the wild-type TRAIL or TRAIL mutants was made in cell culture medium. 50 µl of each dilution was added to a 96-well tissue culture micro plate (Greiner) and 100 µl of cell suspension was added, to a final cell number of 1×10$^4$ cells/well. Mixtures were incubated for 16 h at 37° C. under a humidified atmosphere containing 5% CO$_2$. Subsequently, 20 µl of MTS reagent was added. Cell viability was determined after 30 min incubation by measuring the absorption at 490 nm.

Receptor Binding

Binding experiments were performed using a surface plasmon resonance-based biosensor Biacore 3000 (Biacore AB, Uppsala, Sweden), at 25° C. Recombinant receptors were ordered from R&D systems (R&D systems, Minneapolis, Minn., USA). Immobilization of the receptors on the sensor surface of a Biacore CM5 sensor chip was performed following a standard amine coupling procedure according to the manufacturer's instructions. A reference surface was generated simultaneously under the same conditions but without receptor injection and used as a blank to correct for instrument and buffer artifacts. Purified wild-type TRAIL and TRAIL mutants were injected in two-fold at a concentration of 2 µg/ml and at a flow rate of 20 µl/min flow rate. Binding of ligands to the receptors was monitored in real-time. The receptor/sensor surface was regenerated using 3 M sodium acetate pH 5.2 injections.

Computer Screening

Novel mutants of TRAIL have been designed in order to increase the stability of the bioactive trimer. Predictions were based on the automated computer algorithm, PERLA, as described above. Briefly, the program performs strict inverse folding: a fixed backbone structure is decorated with amino acid side chains from a rotamer library. Relaxation of strain in the protein structure is achieved via the generation of subrotamers. Most terms of the scoring function are balanced with respect to a reference state, to simulate the denatured protein. The side chain conformers are all weighted using the mean-field theory and finally candidate sequences with modelled structures (PDB coordinates) are produced. Energy evaluation of the modelled structures was carried-out by a modified version (Schymkowitz, J., Borg, J., Rousseau, F. & Serrano, L, "manuscript in preparation") of FOLD-X, available at (http://fold-x.embl-heidelberg.de). The force field module of FOLD-X evaluates the properties of the structure, such as its atomic contact map, the accessibility of its atoms and residues, the backbone dihedral angles, in addition to the H-bond network and electrostatic network of the protein. The contribution of water molecules making two or more H-bonds with the protein is also taken into account. FOLD-X then proceeds to calculate all force field components: polar and hydrophobic solvation energies, van der Waals' interactions, van der Waals' clashes', H-bond energies, electrostatics, and backbone and side chain entropies.

Selection of the Template Sequence

The template selected was 1DU3 (Cha et al., *J. Biol. Chem.* 275, 31171-31177 (2000)). The crystal structure at 2.2 Å resolution contains the trimeric structure of human TRAIL in complex with the ectodomain of the DR5 (TRAIL-R2) receptor. The TRAIL monomer lacks an external, flexible loop (130-146), not involved in receptor binding or in monomer-monomer interaction. To complete the molecule, this loop was modelled using the structure of 1D4V (2.2 Å) (Mongkolsapaya et al., *Nat. Struct. Biol.* 6, 1048-1053 (1999)), a monomeric TRAIL in complex with DR5 (TRAIL-R2) receptor, having the atomic coordinates of the loop. Finally, the TRAIL molecule was isolated by removing the receptor molecules from the PDB file.

Computational Design of Mutants

The visual inspection of the isolated monomers, monomer-monomer interface and central core of TRAIL showed several residues as potential candidates for mutagenesis. The highly conserved hydrophobic residues were discarded from this list, as well as residues involved in receptor binding. These residues could not be mutated without disrupting interactions with the receptor. One TRAIL variant (M2), however, that showed a significant predicted increase in stability but also contained residues involved in receptor interaction, was retained for subsequent experimental analysis.

The sequence space search for every position was simplified by checking the naturally occurring amino acids in a multiple sequence alignment of proteins belonging to the TNF ligand family, thus decreasing the computing time, and subsequently focusing on non-conserved residues. The use of protein rational design and force field algorithms (PERLA, FOLD-X) allowed the identification of a list of mutant sequences with potential relevance for TRAIL stability. Four sets of residues were selected for design (FIG. 1b and Table 1): (1) non-conserved residues at the surface of the monomer ('monomer' set), (2) non-conserved residues near positions close to the interface between two monomers ('dimer' set), (3) non-conserved residues along the central trimeric axis ('trimer' set) and (4) a miscellaneous set ('misc. set'). The automated computer algorithm PERLA was applied as previously described (Angrand et al., *Biomol. Eng* 18, 125-134 (2001)). Amino acid substitutions were introduced at the non conserved residue positions in conformations (side chain rotamers) compatible with the rest of the structure. Subsequently, favourable mutations were combined and evaluated in terms of free energy (kcal mol$^{-1}$), and unfavourable combinations (e.g. high Van der Waals' clashes) were eliminated. An output of sequences and coordinates was produced and ranked in terms of free energy using FOLD-X and subsequently reintroduced in the design algorithm for a $2^{nd}$, $3^{rd}$ or $4^{th}$ round of design, if necessary. Table 1 summarizes the list of mutants assayed in silico for increased stability of TRAIL. Some of these predictions were discarded directly after theoretical energy calculations, without further experimental analysis.

Results

Description of the Tested Mutations

Predicted mutants were energy minimized and subsequently analyzed with FOLD-X. The energy values obtained were compared to that of the wild-type structure and used for discrimination of candidates. Mutants were selected based on an improvement in free energy relative to wild-type TRAIL (Table 2). In the monomeric set, M1 (E194I, I196S) was selected because of the large improvement of energy compared to wild-type TRAIL ($\Delta\Delta G$=-9.7 kcal mol$^{-1}$ monomer$^{-1}$). This high energy value is due to the fact that a trimer is being studied, in addition to the presence of significant van der Waals' clashes in the crystal structure (~5 kcal mol$^{-1}$ monomer$^{-1}$), which are removed upon mutation. The mutations are located in the external loop connecting the C and D anti-parallel beta strands (CD loop), following the notation according to Eck (Eck et al., *J. Biol. Chem.* 267, 2119-2122 (1992)). The predicted increase in stability of M1 can be explained since Glu 194 is surrounded by hydrophobic groups (Trp 231, Phe 192, Ala 235) and the carboxyl group is uncompensated. The mutation Glu 194 to Ile rectifies this situation by replacing the charged residue for a medium sized hydrophobic residue. Conversely, Ile 196 is surrounded by polar residues (Asn 202, Lys 233) and is very close to the backbone, resulting in probable van der Waals' clashes. Mutation to Ser avoids clashes and allows formation of a hydrogen bond to Asn 202, located in the opposite part of the CD loop (FIG. 6a). Both mutations improve polar solvation energy, in addition to ameliorating side chain and backbone entropy.

In the dimeric set (Table 2), the design of M2 (D203I, Q205M, Y237F) leads to the creation of a hydrophobic cluster to stabilize the interaction between residues 203 and 205 (D strand) of one monomer, and residue 237 (F strand) of the adjacent monomer. Gln 205 and Tyr 237 together form an intermolecular hydrogen bond, and Asp 203 points to a gap in the monomer-monomer interface. Mutation to Ile (203), Met (205) and Phe (237) breaks the Q205-Y237 hydrogen bond, but facilitates the tight packing of these residues, improving van der Waals' interactions, hydrophobic and polar solvation energies of the entire TRAIL molecule, without a further increase of van der Waals' clashes (FIG. 6b). Although FOLD-X predicted that the affinity of M2 for the DR5 (TRAIL-R2) receptor is lower ($\Delta\Delta G_{binding}$=7.3 kcal mol$^{-1}$ monomer$^{-1}$) than for wild-type TRAIL, this mutant was retained as a control to evaluate the accuracy of the procedure.

Residue 225 of M3 (S225A), belonging to the 'Miscellaneous set', is located in strand E and is solvent exposed in the monomeric form. However, after trimerization, this position becomes buried in a small pocket, leaving the side chain of the hydrogen bond donor Ser uncompensated. After mutation to Ala, the energy of the model is better than wild-type TRAIL for both polar and hydrophobic solvation energies, in addition to side chain entropy.

The Arg 227 residues of the trimeric set mutant (M4) are located in strand E, equidistantly opposed in a central position along the longitudinal axis of the TRAIL trimer. The three arginines are surrounded by hydrophobic (Ile242), polar (Ser241, Ser225) and aromatic (Tyr 240, Tyr 243) residues. These tyrosines direct the hydroxyl groups away from Arg 227, thus creating a rather hydrophobic cavity. The high concentration of positive charges is apparently not well compensated, since it forms only hydrogen bonds with the backbone (carbonyl groups of Ser241). Thus, the mutation of these positions to Met could help to accommodate the hydrophobic environment, as well as to decrease the repulsion of monomers due to uncompensated positive charges.

Mutagenesis and Purification of Mutants

The highest ranking mutants M1 and M2 together with M3 and M4, were selected for further experimental analysis (Table 2). A mutant (C1) combining the mutations of M1 and M3 was also constructed. All the designed TRAIL mutants were expressed in *E. coli* and purified successfully with a protein yield of ~0.7-2 mg/l. Far-UV CD wavelength spectra indicated that all mutants were properly folded with characteristics of a β-sheet containing protein, similar to that of wild-type TRAIL. Gel-filtration and dynamic light scattering measurements showed that all mutant protein solutions contained a single molecule species, consistent with a trimeric oligomerization state. Analytical ultracentrifugation with wild-type TRAIL and M1 corroborated this finding (data not shown).

In Vitro Bioactivity and Binding of Designed Mutants

Figure 2:
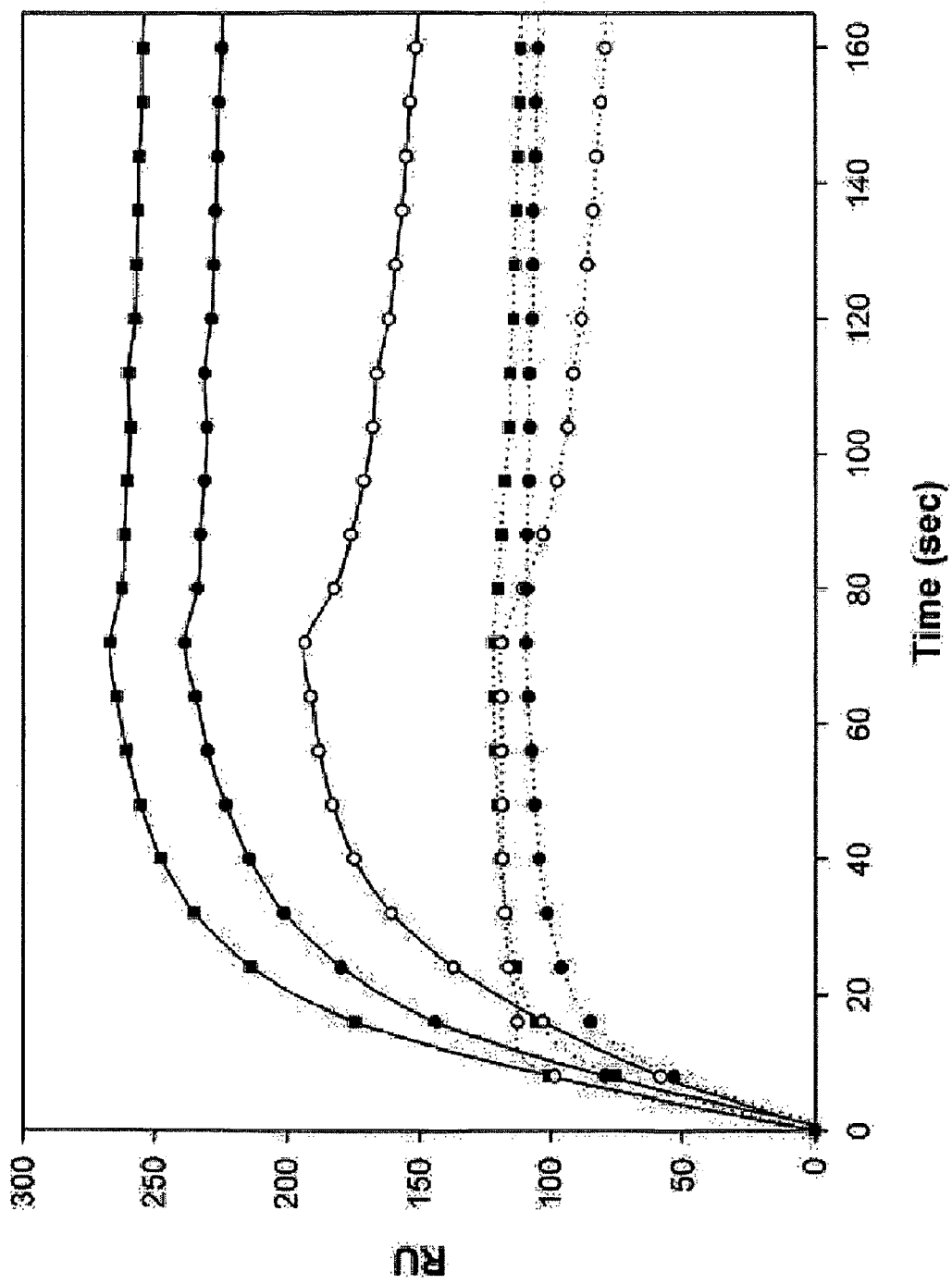

Bioactivity of the TRAIL mutants was assessed in vitro using the Colo205 human colon cancer cell line with a MTT based viability assay. A reduction in viability was measured using increasing concentrations of wild-type TRAIL or TRAIL mutants relative to the control. While M1, M3 and C1 showed a bioactivity comparable to that of wild-type TRAIL ($ED_{50}$~5 ng/ml), M2 exhibited bioactivity of nearly one order of magnitude lower ($ED_{50}$~50 ng/ml). Real-time binding of wild-type TRAIL and TRAIL mutants to the death receptors DR4 (TRAIL-R1) and DR5 (TRAIL-R2) was assessed using surface plasmon resonance with a Biacore 3000 instrument. Sensograms of M1, M3 and C1 were identical to that of wild-type TRAIL. In contrast, M2 whilst showing a similar level of binding to both receptors, displayed an increased off-rate when compared to the wild-type TRAIL sensogram (FIG. 2).

Thermal Unfolding

The thermal unfolding of wild-type TRAIL and TRAIL mutants was monitored by measuring changes in molar ellipticity at 222 nm upon heating. FIG. 3 shows the heat induced changes of wild-type TRAIL and TRAIL mutants. TRAIL shows an onset of unfolding at approximately 70° C. and has a transition midpoint of 77° C. The TRAIL mutants show however, onset of unfolding at increased temperatures and higher transition midpoints (FIG. 3). For M1 the onset of unfolding was at approximately 76° C. and the transition midpoint was at 85° C. M2 showed an onset of unfolding at approximately 74° C. M3 gave intermediate values between those of wild-type TRAIL and M1, with an onset of unfolding of 73° C. and a transition midpoint of 80° C. Mutant C1, representing the combined mutations of M1 and M3 showed values comparable to that of M1. The mutant belonging to the trimeric set (M4), however, showed an experimentally determined stability of approximately 3° C. less than wild-type TRAIL, and was therefore discontinued. The initial increase in molar ellipticity around 76° C. for M2 is due to an overall change of the far UV spectrum, reflecting a loss of structural properties of the starting material (data not shown). Upon cooling all protein solutions were turbid, indicating irreversible aggregation, therefore no thermodynamic parameters could be derived. Far and near UV wavelength CD scans at increasing temperatures confirmed the above findings (data not shown).

Accelerated Thermal Stability Study

In order to test the stability of TRAIL and TRAIL mutants over time, an accelerated thermal stability measurement was performed. The temperature of 73° C. was chosen to measure effects on stability within a 1 h timeframe. At this temperature wild-type TRAIL starts to unfold, while the mutants are still properly folded (FIG. 3). Protein solutions with the same concentration as used in the thermal unfolding measurements were incubated at 73° C. for 1 h and changes in molar ellipticity at 222 nm were measured (FIG. 4). The ellipticity of wild-type TRAIL decreased from the onset, giving a half-life of approximately 13 min. The signal for the M1, M2 and C1 mutants remained essentially constant, indicating an increased thermal stability. M3 showed a half-life of approximately 24 min. These measurements, however, are not indicative of the bioactive trimeric structure of the TRAIL molecule, but of the secondary structure of the monomeric unit. To monitor a concomitant increase in biological activity at elevated temperatures of the mutants with unchanged biological activity (M1, M3 and C1), protein solutions with the same concentrations as used in the thermal unfolding measurements were incubated at 73° C. and samples were taken at regular intervals for 1 h. Samples were subsequently diluted in tissue culture medium and added to Colo205 cells, resulting in a final concentration of 100 ng/ml. After overnight incubation the viability of the cells was measured using a MTT assay. Wild-type TRAIL showed decrease in bioactivity after 20 min of incubation, while M1 and C1 retained full bioactivity after incubation at 73° C. for 1 h (FIG. 5). M3 displayed an intermediate bioactivity between wild-type TRAIL and the other mutants. The increases in thermal stability of the mutants as measured with CD could therefore be correlated with a more stable biologically active trimeric molecule.

Discussion

Others have previously applied computational engineering techniques to improve thermal stability of alpha-helical proteins or monomeric beta-sheet molecules. However, frequently, monomeric proteins of less than 100 amino acids were used as targets. To our knowledge, this report is the first example of computational redesign of a large trimeric all-β-sheet protein towards a more thermal-stable variant. Significantly, it shows that the principles learned from design and engineering of small proteins can also be applied for large multimeric protein complexes.

The wild-type TRAIL (114-281) molecule has a relatively high thermal stability if compared to some members of the TNF ligand family. Human tumor necrosis factor alpha (TNF-α), for example, has an apparent $T_m$ of 65° C. as measured with circular dichroism (CD) (Narhi et al., *Biochemistry* 35, 11447-11453 (1996)) and the CD40L receptor binding domain has an apparent $T_m$ of 60° C. as measured with differential scanning calorimetry (DSC) (Morris et al., *J. Biol. Chem.* 274, 418-423 (1999)). In parallel investigations, we can show using CD that RANKL however, is more thermal stable than TRAIL, with an apparent $T_m$ of 5° C. higher than wild-type TRAIL, confirming another study (Willard et al., *Protein Expr. Purif* 20, 48-57 (2000)). In this study, we investigated the possibility of further increasing the thermal stability of TRAIL, as a model for all-β-sheet proteins, through the use of computational engineering.

We succeeded in extending the apparent thermal stability of the β-sheet protein by more than 5° C. by using a combined approach, employing both TNF ligand family alignment information and an automated computational design algorithm. Due to the non-reversible nature of the unfolding reaction, the apparent $T_m$ is not a perfect indication of an increase in stability. From a functional point of view, therefore, it also makes sense to study the time taken for the protein to denature at high temperature and to relate this to an effect on biological activity. The accelerated thermal stability study showed that the increase in thermal stability of the mutants as measured with CD spectroscopy (FIG. 4) can be correlated with the preservation of overall structural characteristics as highlighted by the lasting bioactivity of M1 during the experimental timeframe (FIG. 5). When measuring the residual bioactivity of wild-type TRAIL and TRAIL mutants upon incubation at 73° C. for 1 h, it was shown that, while wild-type TRAIL was all but thermally inactivated after ~20 min, the mutants, significantly, had an improved stability with respect to wild-type TRAIL (FIG. 5). Thus measuring the stability of wild-type TRAIL and M1 at 73° C. is in this case indicative of an increased stability for M1 at more relevant temperatures, such as 37° C. or room temperature. Although not tested in this study, it has been shown that in case of certain therapeutically interesting proteins, improvement of thermal stability can also be indicative of an improved in vivo half-life (Luo et al., *Protein Sci.* 11, 1218-1226 (2002); Filikov et al., *Protein*

Sci. 11, 1452-1461 (2002)). We are currently conducting studies to confirm this for our mutants. It is advantageous to use alignment information in order to focus the design on non-conserved residue positions. The reason for this is that conserved residues are usually retained in a family for a good reason and it is probable that any mutation will decrease protein stability (Serrano et al., *J. Mol. Biol.* 233, 305-312 (1993); Steipe et al., *J. Mol. Biol.* 240, 188-192 (1994)). On the other hand, regions with high sequence variability are tolerant to mutation and it can be expected that variants that stabilize the protein can be found in these regions (Serrano et al., *J. Mol. Biol.* 233, 305-312 (1993)). To accomplish our goal of redesigning a β-sheet protein, TRAIL, and to generate stable variants with the minimum number of mutations, the conserved residues forming the trimeric interface were therefore largely excluded from the prediction/optimization strategy. This resulted in an approach which focused mainly on improvement of the stability of the monomer (intra-chain stabilization; monomeric set) or improving monomer-monomer contacts (inter-chain stabilization; dimeric set). See Table 1.

M1, M2, M3 and C1 showed, in agreement with our predictions, an increase in thermal stability (Table 2; FIG. 3-5). Different basic principles were used in the M1, M2 and M3 designs. M1 shows an example of intra-chain stabilization. Stabilization of the flexible CD loop at the surface of each TRAIL monomer results in an increased stability of the entire trimer. This loop is not directly involved in receptor binding and is disordered in un-complexed wild-type TRAIL structures (Cha et al., *Immunity.* 11, 253-261 (1999); Hymowitz et al., *Biochemistry* 39, 633-640 (2000)), but becomes ordered on binding to DR5 (TRAIL-R2) (Mongkolsapaya et al., *Nat. Struct. Biol.* 6, 1048-1053 (1999); Hymowitz et al., *Mol. Cell* 4, 563-571 (1999); Cha et al., *J. Biol. Chem.* 275, 31171-31177 (2000)). M2, however, illustrates the optimization of the interactions between two adjacent monomers, i.e. interchain stabilization. M4 displays the stabilization of the trimeric molecule by removing a buried unsatisfied hydrogen bond donor. Contrary to our expectations, the combination mutant, C1 (M1 and M3 combined) did not result in significant additive thermal stability. This might be due to the effects of local unfolding around residue 194 and 196, which could be more dominant than the effects of unfolding around residue 225. Although the predicted free energy change relative to wild-type TRAIL (−9.1 kcal mol$^{-1}$ monomer$^{-1}$) is favourable for M4, the experimentally determined stability was approximately 3° C. less than wild-type TRAIL. This is probably due to the fact that, the three central arginines, in addition to the hydrogen bonds formed with the backbone, trap water in the central core of the trimer. Water bridges are thus formed to compensate the positive charges and this results in further stabilization of the trimer. The mutation Arg 227 Met is presumably less stable since the backbone's carbonyl groups are uncompensated and destabilize the trimer.

The increase in thermal stability did not affect the biological activity of M1, M3 and C1. M2 was more stable than wild-type TRAIL but the formation of an electrostatic interaction between Gln 205 and Arg 154 of the DR5 (TRAIL-R2) receptor was prevented (FIG. 6*b*). This resulted in a subsequent 10-fold decrease in biological activity (50 ng/ml) when compared to wild-type TRAIL (5 ng/ml), as predicted by FOLD-X ($\Delta\Delta G_{binding}$=7.3 kcal mol$^{-1}$ monomer$^{-1}$). Our findings confirmed an earlier study showing decreased bioactivity of alanine mutants at these positions (Hymowitz et al., *Biochemistry* 39, 633-640 (2000)). Analysis of binding to the DR4 (TRAIL-R1) and DR5 (TRAIL-R2) receptors, using surface plasmon resonance, shows an increased off-rate for M2, indicating a lower affinity for both receptors, when compared to wild-type TRAIL and M1 (FIG. 2). Since ligand-receptor binding sites are normally "high energy regions", the M2 mutations were expected to stabilize the TRAIL molecule. Thus, this could be regarded as an example of a possible increase in stability which is counterbalanced in evolution by loss of function. Frequently, other computational redesign studies limited the screening for improvement of thermal stability to the core of the molecule (Malakauskas & Mayo, Nat. Struct. Biol. 5, 470-475 (1998); Luo et al., *Protein Sci.* 11, 1218-1226 (2002); Filikov et al., *Protein Sci.* 11, 1452-1461 (2002)). Here we show that computational redesign techniques can also involve inter-chain interfaces and surface residues of the molecule, to successfully stabilize the structure.

Performance of PERLA/FOLD-X was successful in the case of the intra-chain (monomer) set, the inter-chain (dimeric) set and the miscellaneous set. The experimental data corresponding to these designs showed all variants within these sets were more stable than wild-type TRAIL. Significantly, we could show that stabilization of the CD loop in a single monomer resulted in stabilization of the entire trimeric molecule (FIG. 6*a*).

Our studies have shown that computer redesign of a more thermal stable multimeric all β-sheet protein is achievable. Computational protein redesign is therefore a valuable addition to other protein engineering methodologies, such as directed evolution or experimental high throughput approaches, as a tool for the improvement of protein properties. Since the computational method used in our study is based on general physical principles, our findings can be further applied to design other TNF ligand family members with improved thermal stability.

Example 2

TRAIL Variants Selective for the DR4 (TRAIL-R1) or DR5 (TRAIL-R2) Receptor

Methods

All reagents were of analytical grade unless specified otherwise. Isopropyl-β-D-1-thiogalactoside (IPTG), ampicillin and dithiotreitol (DTT) were from Duchefa. Complete® protease inhibitor cocktail was purchased from Roche. Chromatographic columns and media were from Amersham Biosciences. Restriction enzymes used were purchased from New England Biolabs. All other chemicals were from Sigma.

Computational Design of Mutants

Computational design using the protein design algorithm, PERLA and FOLD-X has been described above. Similarly, the resultant PDB files containing the mutations were energy minimized using GROMOS 43B1 as implemented in Swiss-PdbViewer v3.7b2, and evaluated by FOLD-X (http://fold-x.embl-heidelberg.de). The final energies of interaction from the designs of TRAIL mutants interacting with its different receptors are compared to the reference, wild-type TRAIL in complex with its four membrane receptors and expressed as $\Delta\Delta G$ (kcal mol$^{-1}$).

Computer Screening

Novel mutants of TRAIL have been designed in order to shift selectivity/specificity towards its different membrane receptors (DR4(TRAIL-R1), DR5(TRAIL-R2), DcR1 (TRAIL-R3) and DcR2 (TRAIL-R4)). These receptors are described by Pan et al., Science. 1997 Apr. 4; 276(5309): 111-3 (DR4); Screaton et al., Curr Biol. 1997 Sep. 1; 7(9): 693-6 (DR5); Degli-Esposti et al., J Exp Med. 1997 Oct. 6;

186(7):1165-70 (DcR1 (TRAIL-R3)) and Marsters et al., Curr Biol. 1997 Dec. 1; 7(12):1003-6 (DcR2 (TRAIL-R4)).

Designs were based on the automated computer algorithm, PERLA, as described above. Briefly, this algorithm performs strict inverse folding: a fixed backbone structure is decorated with amino acid side chains from a rotamer library. Relaxation of strain in the protein structure is achieved via the generation of subrotamers. Most terms of the scoring function are balanced with respect to a reference state, to simulate the denatured protein. The side chain conformers are all weighted using the mean-field theory and finally candidate sequences with modelled structures (PDB coordinates) are produced. Energy evaluation of the modelled structures was carried-out by a modified version (Schymkowitz, J., Borg, J., Rousseau, F. & Serrano, L, "manuscript in preparation") of FOLD-X, (available at http://fold-x.embl-heidelberg.de). The force field module of FOLD-X evaluates the properties of the structure, such as its atomic contact map, the accessibility of its atoms and residues, the backbone dihedral angles, in addition to the H-bond network and electrostatic network of the protein. The contribution of water molecules making two or more H-bonds with the protein is also taken into account. FOLD-X then proceeds to calculate all force field components: polar and hydrophobic solvation energies, van der Waals' interactions, van der Waals' clashes, H-bond energies, electrostatics, and backbone and side chain entropies.

Selection of the Template Sequence

Template was selected from the Protein Data Bank, PDB identifier 1DU3. This is the crystal structure at 2.2 Å resolution of the trimeric structure of human TRAIL in complex with the ectodomain of the DR5 (TRAIL-R2) receptor. In this structure TRAIL monomers lack an external, flexible loop (residues 130-146), not involved in receptor binding. To complete this template, this loop was modelled using the crystal structure of 1D4V (2.2 Å), a monomeric TRAIL in complex with DR5 (TRAIL-R2) receptor, which has the atomic coordinates of this loop.

Modeling TRAIL Non-crystallized Receptors

Models of the three other TRAIL membrane receptors (DR4 (TRAIL-R1), DcR1 (TRAIL-R3) and DcR2 (TRAIL-R4)) were obtained using "What If Homology Modeling web interface" (available at http://www.cmbi.kun.nl/gv/servers/WIWWWI/). Afterwards, pdb files of TRAIL in complex with these three receptors were generated by imposing their backbone atoms over the same atoms of the receptor DR5 (TRAIL-R2), using Swiss-PdbViewer v3.7b2. Finally, template receptor DR5 (TRAIL-R2) was removed from the generated PDB file.

Modeling Interactions Between TRAIL and Modelled Receptors

Rational design of the occurring interactions between TRAIL and the three modelled receptors was carried out in the following way: First, receptors' binding interface with TRAIL were studied looking for target amino acids for rotamer replacement. Selected side chains were the ones physically close enough to TRAIL to be potentially interacting with it. Conserved residues with receptor DR5 (TRAIL-R2) were discarded from this rotamer replacement. Second, PERLA performed a rotamer search looking for better side chains conformations, aiming to model the expected interactions of TRAIL with these receptors. Finally, an overall visual inspection of the binding interface of TRAIL with the different receptors was carried out and some rotamers were changed.

Computational Design of Mutants

Only TRAIL amino acids located in the receptor-binding interface were considered as potential candidates for in silico mutagenesis. Residues interacting either with conserved amino acids among the four different receptors or with receptor backbone were discarded from this list. The use of protein rational design and force field algorithms (PERLA, FOLD-X) allowed the identification of a list of mutant sequences with potential relevance for TRAIL selectivity/specificity.

The automated computer algorithm PERLA was applied as previously described. All possible amino acid substitutions (with the exception of Glycine, Proline, and Cysteine) were introduced at the previously selected residue positions in conformations (side chain rotamers) compatible with the rest of the structure. Subsequently, favourable mutations were evaluated in terms of free energy (kcal mol-1), and unfavourable mutations (e.g. high Van der Waals' clashes) were eliminated. An output of sequences and coordinates was obtained and ranked in terms of free energy using FOLD-X. Some of these predictions were discarded directly after theoretical energy calculations, without further experimental analysis.

Cloning and PCR cDNA corresponding to human soluble TRAIL (aa 114-281) was cloned in pET15B (Novagen) using NcoI and BamHI restriction sites. The N-terminal sequence encoding a His-tag and protease recognition site was therefore removed. Mutants were constructed by PCR using the Quick Change Method (Stratagene) or a modified megaprimer method. The polymerase used was Pfu Turbo supplied by Stratagene. Purified mutagenic oligonucleotides were obtained from Invitrogen. Introduction of mutations was confirmed by DNA sequencing.

Screening for Selectivity Mutants

TRAIL mutant constructs were transformed to *Escherichia Coli* BL21 (DE3) (Invitrogen). Mutants and wild-type TRAIL were grown at a 10 ml scale, using a 2×LB medium. Cultures were grown to $OD_{600}$ 0.5 at 37° C. and 250 rpm, and protein expression was subsequently induced with 1 mM IPTG. $ZnSO_4$ was added at a concentration of 100 μM to promote trimer formation. Temperature was lowered to 28° C. and induction was continued for 5 h. Cells were harvested by centrifugation. Pellet was resuspended in extraction buffer (PBS pH 7.3, 10% (v/v) glycerol and Complete® protease inhibitor cocktail), in 25% of the original volume. Cells were disrupted using sonication and extracts were clarified by centrifugation at 20,000 g. TRAIL mutant protein expression was assessed using SDS-PAGE. Clarified extracts of mutants that were well expressed, were subsequently diluted 1:50 in HBS-EP buffer. These dilutions of the wild-type TRAIL and TRAIL mutants were injected in two-fold, at a flow rate of 50 μl/min on a Biacore 2000. A Biacore CM5 sensor chip coated with the TRAIL receptors DR4 (TRAIL-R1), DR5 (TRAIL-R2) and DcR1 (TRAIL-R3) and with RANK (receptor) as control surface, was used. Binding of ligands to the receptors was monitored in real-time. The receptor/sensor surface was regenerated using 3 M sodium acetate pH 5.2 injections. Ratios of binding for the different receptors were calculated relative to DR4 (TRAIL-R1) or DR5 (TRAIL-R2) binding, respectively. Mutants having different binding profiles compared to the binding profiles of wild-type TRAIL were chosen for subsequent analysis.

Expression and Purification of Wild-type TRAIL and Mutants

The chosen mutants were grown in shake flasks at a 1 l scale at 250 rpm and 37° C., using a 2×LB medium. Protein expression was induced with 1 mM IPTG when the culture reached $OD_{600}$ 0.5, $ZnSO_4$ was added at a concentration of 100 μM. Temperature was lowered to 28° C. and induction was continued for 5 h. The isolated pellet was resuspended in 3 volumes extraction buffer (PBS pH 8, 10% (v/v) glycerol, 7 mM β-mercapto-ethanol). Cells were disrupted using sonication and extracts were clarified by centrifugation at 40,000 g. Subsequently, the supernatant was loaded on a nickel charged IMAC Sepharose fast-flow column and wild-type TRAIL and TRAIL mutants were purified as described by Hymowitz (see above) with the following modifications: 10% (v/v) glycerol and a minimal concentration of 100 mM NaCl were used in all buffers. This prevented aggregation during purification. After the IMAC fractionation step, 20 μM $ZnSO_4$ and 5 mM of DTT (instead of β-mercapto-ethanol) was added in all buffers. Finally, a gelfiltration step, using a Hiload Superdex 75 column, was included. Purified proteins were more than 98% pure as determined using a colloidal coomasie brilliant blue stained SDS-PAGE gel. Purified protein solutions were flash frozen in liquid nitrogen and stored at −80° C.

Screening for Selectivity Mutants

Extracts of 16 expressing mutants were evaluated for binding to DR4 (TRAIL-R1), DR5 (TRAIL-R2) and DcR1 (TRAIL-R3) receptors using surface plasmon resonance with a Biacore 3000 instrument. Binding to murine RANK (receptor) was monitored as control as wild-type TRAIL does not bind to this receptor. Control extracts of BL21 (DE3) culture without an over-expression plasmid and of a BL21 (DE3) culture with plasmid over-expressing SH3 domain were also injected. No binding was observed for these extracts. The ratio of DR4 (TRAIL-R1), DcR1 (TRAIL-R3) or RANK (receptor) binding with respect to DR5 (TRAIL-R2) receptor binding (FIG. 7) and of DR5 (TRAIL-R2), DcR1 (TRAIL-R3) or RANK (receptor) binding with respect to DR4 (TRAIL-R1) receptor binding (FIG. 8), were calculated. The ratios values obtained for TRAIL selectivity mutants binding were compared to the ratios obtained for wild-type TRAIL binding. Receptor binding curves were also visually inspected for alterations in on and off rates when compared to the on and off rates of wild-type TRAIL.

Two mutants, D269H and G160M, with a reduced binding to the DR4 (TRAIL-R1) and unchanged binding to the DR5 (TRAIL-R2) receptor ("selective" for DR5 (TRAIL-R2)) were chosen for further analysis. We have shown an increased off-rate of D269H w.r.t. DR4 but this does not imply that we have seen an increased binding for DR5. Our current data does imply that we have directed the binding of this mutant towards DR5 binding, hence it is more selective/specific for the DR5 receptor. Affinity can of course be improved after selectivity variants are chosen. I220M and E195R (not shown) were also elected, as they also showed a reduced binding to the DR4 (TRAIL-R1) and increased binding to the DR5 (TRAIL-R2) receptor. The effects, however, were smaller than that of the previous two mutants. D218Y was chosen for further analysis, as it showed a small preference for binding to the DR4 (TRAIL-R1) receptor, compared to wild-type TRAIL. R130E was chosen as it showed a small reduction in binding to the DcR1 (TRAIL-R3) receptor (less "selective" for DcR1 (TRAIL-R3)).

Determination of Receptor Binding

Mutants R130E, G160M, D218Y, I220M and D269H were purified. Binding of the purified mutants was assessed in real time using surface plasmon resonance on a Biacore 3000 with a sensor chip as described above. Mutants and purified wild-type TRAIL were injected in a concentration series of 17.3, 34.5, 69, 138 and 276 mM at a flow rate of 70 μl/min. Measurements performed at 37° C. to allow increased $k_{off}$ and dissociation was monitored for 20 min. Measured $k_{on}$ and $k_{off}$ rates were used to calculate apparent $K_d$ values for the mutants for the respective receptors. A global fit procedure was used and a 1:1 Langmuir interaction model. A biphasic behavior was found for the $k_{on}$ and $k_{off}$. The preliminary apparent $K_d$ values were calculated and are shown in table 3.

In vitro studies of the TRAIL mutants D269H

Experimental Conditions

Cell line and treatment: Colo205 colon cancer cells were maintained in RPMI1640 medium, 10% FCS, 1% penicillin, 1% streptomycin in humified incubator, 37° C., in 5% CO2 environment. TRAIL receptor inhibitors (neutralising antibodies) were always added 1 h before TRAIL addition. The Colo205 cells were seeded the day before the experiment at $10^5$ cells/ml in 24 well plates, 1 ml/well were treated with increasing concentration of antiDR4 and anti DR5 neutralising antibodies for 1 h. 20 ng/ml D269H was added to the cells and incubated for 2 h and 30 minutes. After treatment, the cells were harvested by scraping them gently off the wells and spun down.

Annexin V Staining:

Control or treated Colo205 cells were harvested and collected by centrifugation, washed once in Annexin V incubation buffer and resuspended in 400 μl fresh incubation buffer. 1 μl Annexin V was added to the samples, incubated at room temperature for 10 minutes and measured immediately on a FACSCalibur Flow cytometer (Beckton Dickinson), results being expressed as % of annexin V positive cells.

Caspase assay: Colo205 cells were plated in 6 well plates at 200,000 cells/ml, 3 ml/well on the day before the experiment. R2C16 (100 ng/ml and 500 ng/ml), antiDR4 (TRAIL-R1) and antiDR5 (TRAIL-R2) neutralizing antibodies (Alexis) (200 ng/ml) were added into the culture medium 1 h before adding TRAIL (10 ng/ml). Cells were harvested for caspase activity assay after 2 h treatment with TRAIL.

Cells were pelleted, washed twice in ice cold PBS, resuspended in 50 ml PBS, 2×25 ml cell suspension was snap frozen. Caspase enzyme activity was measured using fluorescently tagged DEVD-MCA (for caspase-3 and -7-like activity), or IETD-MCA (for caspase-8) tetrapeptides. The fluorescence intensity caused by the released MCA was measured kinetically in 25 cycles with 60 sec intervals. The enzyme activity was calculated as nmole MCA released per minute by 1 mg total protein.

MTT assay: Colo205 cells were seeded in 96 well plates at 200,000 cells/ml, 100 μl/well. Each treatment was carried out in triplicates. After 24 h treatment 500 μg/ml MTT stain was added to the wells and was incubated at 37° C. for 3 h. The reaction was stopped and the formazan precipitate was dissolved by adding 100 μl 20% SDS in 50% dimethylformamide.

Results

For the analysis of the apoptosis inducing potential of D269H TRAIL sensitive Colo205 colon carcinoma cells were treated with increasing concentrations of TRAIL (aa 114-281) or D269H for 2 and 3 hours. Annexin V labelling of the apoptotic cells was used to monitor the level of cell death induced.

Our results (see FIGS. 9, 10 and 11) revealed that the two ligands have comparable death inducing potential in Colo205 cells. Thus, the designed mutations in D269H did not decrease its cytotoxic potential significantly (FIG. 12).

In order to examine which TRAIL receptor is more involved in D269H induced death, 1 hour prior to D269H treatment of Colo205 cells, increasing amounts of neutralizing antiDR4 or antiDR5 antibodies were administered. The presence of the antiDR4 antibody failed to prevent death induced by D269H. On the other hand, already the lowest concentration (200 ng/ml) of antiDR5 antibody almost completely prevented cell death (FIG. 13). These results suggest that D269H induces cell death primarily through ligation of TRAIL receptor 2 (DR5). Similar studies on different cell lines will be required to prove that this effect is not cell type specific and these are on-going.

Example 3

Receptor Specific TRAIL Variants: Binding Analysis by SPR

Binding experiments were performed using a surface plasmon resonance-based biosensor Biacore 3000 (Biacore AB, Uppsala, Sweden), at 37° C. Recombinant receptors were ordered from R&D systems (R&D systems, Minneapolis, Minn., USA). Immobilization of the DR4, DR5 and RANK receptors on the sensor surface of a Biacore CM5 sensor chip was performed following a standard amine coupling procedure according to the manufacturer's instructions. Receptors were coated at a level of ~600-800 RU. Purified wild-type TRAIL and TRAIL mutants were injected in three-fold at concentrations ranging from 250 nM to 0.1 nM at 70 µl/min flow rate and at 37° C. Between injections the receptor/sensor surface was regenerated using 30 µl of 3 M sodium acetate pH 5.2.

Mutants R130E, G160M, D218Y, I220M, D269H, D269K, D269R, D269HT214R, D269HE195R and R191ED267R were purified as described in Example 2. Binding of the purified mutants to immobilized TRAIL-R1, TRAIL-R2 and TRAIL-R3 Fc receptor was assessed in real time using surface plasmon resonance. Mutants and purified wild-type TRAIL were initially analyzed at a concentration of 60 µM (FIG. 14). Binding curves of variants showing a significant change in the ratio TRAIL-R1(DR4)/TRAIL-R2(DR5) binding were subsequently recorded for concentrations ranging from 0.1 to 250 nM. All variants comprising a D269H/R/K substitution were found to be TRAIL-R2 Fc selective. Variants D269H/R/K and D269HE195R showed >10 fold improvement in binding to TRAIL-R2 Fc and >15 fold reduction in binding to TRAIL-R1 Fc relative to wild-type TRAIL (FIG. 15 a,b,c&d). The D269HT214R variant had a comparable improvement as the D269H single mutant in TRAIL-R2 Fc binding, however no detectable binding to TRAIL-R1 Fc was found (FIG. 15 a&c). Variant R191ED267R was also found to be selective for TRAIL-R2; it showed decreased binding to TRAIL-R2 Fc but complete abolishment of binding to TRAIL-R1 Fc (FIG. 16 a&b). Binding of D269H towards the decoy TRAIL-R3 Fc receptor was ~10 fold decreased when compared to wild-type TRAIL (FIG. 18a).

Mutation D218Y was designed to result in a DR4 (TRAIL-R1) specific TRAIL variant. Whereas wild-type TRAIL has a higher affinity for DR5 than DR4 this preference is lost in the mutant (FIG. 16c).

Example 4

TRAIL Variants Selective for DR5: Competition ELISA

To assess the selectivity of the TRAIL-R2 (DR5) selective mutants towards the TRAIL-R2 receptor in the presence of another TRAIL receptor a competition ELISA experiment was performed. Nunc Maxisorb plates were coated during 2 hr with TRAIL-R2-Fc (100 ng/well) in 0.1 M Sodium Carbonate/Bicarbonate buffer pH 8.6 and remaining binding places were subsequently blocked with 2% BSA for 1 hr. After 6 times washing with TBST (TBS-0.5% Tween-20 pH 7.5), pre-incubated (30 min) serial dilutions of soluble TRAIL-R1 (DR4), TRAIL-R2(DR5) or TRAIL-R3 Fc (0-500 ng/well) and 10 ng/well purified rTRAIL or mutants (purified as described in example 2) were added to the wells and incubated for 1 hr at RT. After 6× washing with TBST a 1:200 dilution of anti-TRAIL antibody (R&D systems) was added and incubated for 1 hr at RT and after 6× washing with TBST, subsequently, incubated with a 1:25000 dilution of a horse radish peroxidase conjugated swine-anti goat antibody. After 6× washing with TBST 100 µl of 1-step Turbo TMB solution (Pierce) was added and after ~15 min the reaction was quenched with 100 µl 1 M sulfuric acid. The absorbance was measured at 450 nM on a microplate reader (Thermolab systems). Binding of wild-type TRAIL or mutants to immobilized TRAIL-R2 Fc with 0 ng/well of the soluble receptors was taken as 100% and binding at other concentrations of soluble receptors was calculated relative to 0 ng/well of soluble receptor.

Increasing concentrations of soluble TRAIL-R1 Fc or TRAIL-R2 Fc were both capable of competing with immobilized TRAIL-R2 Fc for wild-type TRAIL binding. In contrast, soluble TRAIL-R1 Fc was unable to compete with immobilized TRAIL-R2 Fc for binding with the TRAIL-R2 selective variants (FIG. 17 a,b,c&d). However, soluble TRAIL-R2 Fc was able to compete for binding with the immobilized TRAIL-R2 Fc. Pre-incubation with increasing concentrations of TRAIL-R3 Fc did not affect the binding of the TRAIL-R2 selective variants to immobilized TRAIL-R2 Fc. Wild-type TRAIL showed, in contrast, a 10-15% decrease in binding to immobilized TRAIL-R2 when pre-incubated with the highest concentration of TRAIL-R3 Fc (FIG. 18b). The difference in level of competition of wild-type TRAIL binding between TRAIL-R3 Fc and TRAIL-R2 Fc is caused by >100 fold difference in affinity of wild-type TRAIL for the two receptors, respectively 200 nM and <2 nM (Truneh et al., J. Biol. Chem. 275, 23319-23325 (2000)).

Example 5

Additional In Vitro Studies of DR5-Selective Mutants

To assess the biological activity of the DR5 (TRAIL-R2) selective mutants an Annexin V based apoptosis assay was performed using a cell-line sensitive for DR5-receptor mediated induction of apoptosis (Colo205) and a cell-line sensitive for DR4 mediated induction of apoptosis (ML-1).

Cell line and treatment: Colo205 colon cancer cells and ML-1 myeloid leukaemia cells were maintained in RPMI1640 medium, 10% FCS, 1% penicillin, 1% streptomycin in humidified incubator, 37° C., in 5% CO2 environment. TRAIL receptor inhibitors (neutralising antibodies) were always added 1 h before TRAIL addition. Cells were seeded the day before the experiment at $2 \times 10^5$ cells/ml in 24 well plates (0.5 ml/well). Colo205 cells were treated with 1 µg/ml of anti-DR4 and/or anti-DR5 neutralising antibodies for 1 h. 20 ng/ml wild-type TRAIL, D269H, D269HE195R or 50 ng/ml D269HT214R was added to the cells and incubated for 2 h and 30 minutes. ML-1 cells were treated with 1 µg/ml of anti-DR4 and/or anti-DR5 neutralising antibodies for 1 h prior to TRAIL treatment. 100 ng/ml wild-type TRAIL, D269H, D269HE195R or D269HT214R was added to the cells and incubated for 12 h.

Annexin V Staining:

Control or treated Colo205 cells and ML-1 cells were harvested and collected by centrifugation, washed once in Annexin V incubation buffer and resuspended in 400 µl fresh incubation buffer. 3 µl Annexin V (IQ Corporation) was added to the samples, incubated at room temperature for 10 minutes and measured immediately on a FACSCalibur Flow cytometer (Beckton Dickinson), results being expressed as % of Annexin V positive cells.

MTT assay: Colo205 cells were seeded in 96 well plates at $2 \times 10^5$ cells/ml (100 µl/well). Each treatment was carried out in triplicates. After 24 h treatment 500 µg/ml MTT stain was added to the wells and was incubated at 37° C. for 3 h. The reaction was stopped and the formazan precipitate was dissolved by adding 100 µl 20% SDS in 50% dimethylformamide.

Results

The MTT assay showed that wild-type TRAIL and D269H, D269HE195R and D269HT214R (purified as described in examples 1 and 2) were biologically active and able to induce cell death in Colo205 cells (data not shown). For the analysis of the specific apoptosis inducing potential of wild-type TRAIL, D269H, D269HE195R and D269HT214R, TRAIL sensitive Colo205 colon carcinoma cells were treated with 20 ng/ml purified wild-type TRAIL or D269H, D269HE195R or D269HT214R for 2.5 hours. Annexin V labelling of the apoptotic cells was used to monitor the level of cell death induced.

Our results revealed that the ligands have comparable death inducing potential in Colo205 cells as wild-type TRAIL. Thus, the designed mutations in D269H, D269HE195R and D269HT214R did not decrease its cytotoxic potential significantly.

In order to examine which TRAIL receptor is more involved in wild-type, D269H, D269HE195R or D269HT214R induced cell-death, 1 hour prior to wild-type or mutant treatment of Colo205 cells, 1 µg/ml of neutralizing anti-DR4 or anti-DR5 antibodies were administered. The presence of the anti-DR4 antibody failed to prevent death induced by D269H, D269HE195R or D269HT214R. On the other hand 1 µg/ml of antiDR5 antibody could significantly reduce the amount cell death. In contrast, both anti-DR4 and anti-DR5 antibodies are able to significantly reduce the amount of cell death induced by wild-type TRAIL in Colo205 cells. These results suggest that D269H, D269HE195R and D269HT214R induce cell death primarily through ligation of TRAIL receptor 2 (DR5).

TRAIL receptor induced apoptosis in ML-1 myeloma cells was found to be mainly mediated by the DR4 (TRAIL-R1) receptor. Only anti-DR4 antibody could significantly reduce wild-type TRAIL mediated cell-death in these cells. Addition of anti-DR5 did not have a significant effect on wild-type TRAIL mediated cell-death. Mutants D269H, D269HE195R and D269HT214R were unable to induce a comparable level of apoptosis as wild-type TRAIL in this cell line. These results suggest that D269H, D269HE195R and D269HT214R are unable to induce cell death through ligation of DR4 (TRAIL-R1).

Taken together, the results obtained with the Colo205 and ML-1 cell lines show that the biological activity of the D269H, D269HE195R and D269HT214R mutants is mainly directed towards the DR5 (TRAIL-R2) receptor.

Example 6

Second Round of Design

Using in vitro and in vivo results obtained from the 1st generation of receptor selective TRAIL mutants DR4 receptor homology models were improved and additional amino acid residue positions in TRAIL were screened for receptor selectivity using methodology as described in Example 2 in order to obtain mutants with improved receptor selective properties. FIG. 20 A depicts the residues used in 1st and 2nd round in silico mutagenesis using PERLA/FOLD-X (highlighted with Van der Waals radius.)

Mutant D269H designed in the 1st round was found to be a critical for DR5 selectivity. Additional, a 2nd round of in silico mutagenesis of the Aspartate at position 269 was performed. From this second round D269K and D269R, in addition to D269H, are predicted to shift receptor selectivity towards DR5 (TRAIL-R2) (FIG. 20 B). (A negative $\Delta\Delta G$ value is indicative of improved binding and a positive $\Delta\Delta G$ of decreased receptor binding.)

From the crystal structure of TRAIL in complex with DR5 (TRAIL-R2), residue 269 seems not to have any direct interaction with the DR5 receptor, however, the substitution of this residue with Lysine, Histidine or Arginine worsens dramatically the binding with all the receptors but DR5. This can be explained due to the presence of a conserved Lysine in position 120 on the receptors DR4, DcR1, DcR2. This lysine, according to our models, is not making any interaction with TRAIL, but is close enough to the receptor interface to have a Van Der Waals clash, or at least, repulsive electrostatic interaction, with the amino acid substitutions in position 269 of TRAIL here described.

This design data correlates with experimental receptor binding studies and competition ELISAs (see also Examples 3 and 4).

Residue 218 was predicted to be important for shifting selectivity to towards DR4 (TRAIL-R1). Mutant D218Y designed in the 1st round confirmed this shift towards DR4 selectivity. Additionally, a 2nd round of in silico mutagenesis of the Aspartate at position 218 was performed. From this second round D218K, D218R and especially D218H, in addition to D218Y, are predicted to shift receptor selectivity towards DR4 (TRAIL-R2) (FIG. 20 C). (A negative $\Delta\Delta G$ value is indicative of improved binding and a positive $\Delta\Delta G$ of decreased receptor binding.)

Residue position 214 and DR5 selectivity. The substitution of TRAIL threonine in position 214 by an arginine, was predicted to shift selectivity towards DR5 (FIG. 20 d). This mutation in combination with the already tested mutation D269H was tested in order to reach a cleaner selectivity. This was experimentally confirmed. D269HT214R showed improved binding towards DR5 (TRAIL-R2) and complete abolishment of DR4 (TRAIL-R1) binding (Examples 3 and 4).

Combination of mutants at positions 214 and 269 for selectivity towards DR5. We have already shown experimental characterization of the mutants D269H, D269K, D269R and T214R-D269H. The additive effect of mutations towards selectivity can be expected, at least presumably, in the cases where the positions of the mutations are far away enough from each other so they cannot make any non-predictable interaction between each other. This is the case of positions 214 and 269, which are around 20 Å away from each other. Therefore, with the data from the mutants D269H and T214R-D269H, we can expect that both mutations contribute to selectivity in an independent way, so we consider the mutant T214R as selective towards DR5.

The presumable structural basis of position 269 selectivity has been already explained before. The fact that the three different substitutions in position 269 give a more or less similar shift in selectivity could possibly mean that this selectivity is reached due to a clash and/or electrostatic repulsion that depends on the amino acid size and/or charge. Therefore, after observing the results of the mutant T214R-D269H, we can presume that the combinations of T214R with either D269R or D269K will have a similar effect on selectivity. PERLA/FOLDX calculations indicate that these mutations have indeed a similar effect.

Example 7

Combination of Stability and Selectivity Mutants

Figure 21:
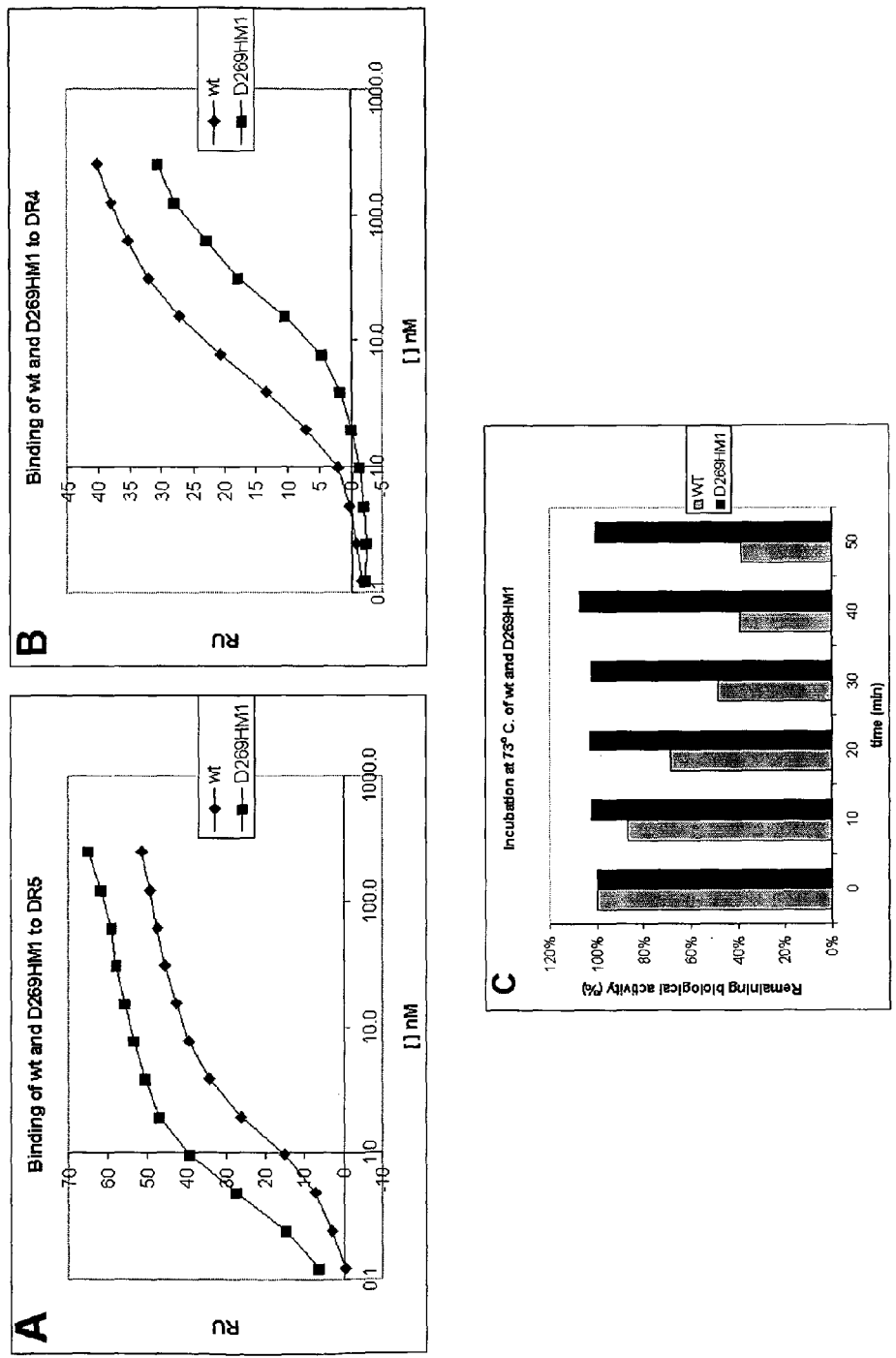

Combinations between the stability variants and selectivity variants described above can be made, giving variants with enhanced stability and altered selectivity/specificity. Combinations between the TRAIL M1 and C1 mutants (stability mutants), combined with one or more of the D269H, D269HE195R, D269HT214R, D269K, D269R and R191ED267R mutants (selectivity mutants) were constructed and purified as described in Examples 1 and 2. Mutants were tested for receptor binding and biological activity as described in Examples 1, 2 and 3. A comparison between wild-type TRAIL and D269HM1 is given as an example. Binding of the purified wild-type TRAIL and D269HM1 to immobilized TRAIL-R1 and TRAIL-R2 Fc receptor was assessed in real time using surface plasmon resonance. Binding curves were recorded for concentrations ranging from 0.1 to 250 nM. Variant D269HM1 showed >8 fold improvement in binding to TRAIL-R2 Fc and >8 fold reduction in binding to TRAIL-R1 Fc relative to wild-type TRAIL (FIG. 21 a&b).

To monitor a increase in biological activity at elevated temperatures of the mutants, protein solutions with a concentration of 100 µg/ml were incubated at 73° C. and samples were taken at regular intervals for 1 h. Samples were subsequently diluted in tissue culture medium and added to Colo205 cells, resulting in a final concentration of 100 ng/ml. After overnight incubation the viability of the cells was measured using a MTT assay. Wild-type TRAIL showed a noticeable decrease in bioactivity after only 10 min of incubation, while D269HM1 retained full bioactivity after incubation at 73° C. for 50 min (FIG. 21 c).

TABLE 1

Residues initially considered for design

| Monomer Set | Dimer Set | Trimer Set | Misc. Set |
|---|---|---|---|
| E194[†] | H125 | R227[†] | A123 |
| I196[†] | F163 | C230 | A272 |
| | Y185 | Y240 | S225[†] |
| | Q187 | | V280 |
| | S232 | | F163 |
| | D234 | | A123 |
| | Y237[†] (D203, Q205) | | V208 |
| | L239 | | |
| | S241 | | |
| | E271[†] | | |
| | F274 | | |

[†]Used in subsequent rounds of design
Mutants in parenthesis were added in subsequent rounds as interaction partners

TABLE 2

Computational design results

| | $\Delta\Delta G_{stability}$* | $\Delta\Delta G_{binding}$*[‡] | Set | Mutations |
|---|---|---|---|---|
| M1 | −9.7 | 0.4 | Monomer | E194I, I196S |
| M2 | −4.0 | 7.3 | Dimer | D203I, Q205M, Y237F |
| M3 | −7.0 | −0.5 | Misc. | S225A |

TABLE 2-continued

Computational design results

| | $\Delta\Delta G_{stability}$* | $\Delta\Delta G_{binding}$*[‡] | Set | Mutations |
|---|---|---|---|---|
| M4 | −9.1 | −1.2 | Trimer | R227M |
| C1 | −11.4 | −0.9 | Combination | M1 + M3 |

*Energy in kcal mol$^{-1}$, calculated per monomer
[‡]$\Delta G_{binding} = \Delta G_{complex} - (\Sigma \Delta G_{chain})$; $\Delta\Delta G_{binding} = \Delta G_{binding}$ mutant − $\Delta G_{binding}$ wild-type

TABLE 3

Apparent $K_d$ values for DR4 (TRAIL-R1) and DR5 (TRAIL-R2) receptors

| | DR4(TRAIL-R1) (nM) | DR5(TRAIL-R2) (nM) |
|---|---|---|
| Wt TRAIL | 0.6 | 0.4 |
| G160M | 0.4 | 0.5 |
| D269H | 0.6 | <0.4 |
| D218Y | ? | ? |
| others | N.D. | N.D. |

TABLE 4

Critical residues identified for receptor binding without distinction between DR4 and DR5.

| Mutant | Effect on DR4 binding | Effect on DR5 binding |
|---|---|---|
| I220H | Highly decreases | Highly decreases |
| I220M | Highly decreases | Highly decreases |
| R149D | Decreases | Decreases |
| R149H | No observable effect | No observable effect |
| E155M | Highly decreases | Highly decreases |
| G160K | Highly decreases | Highly decreases |
| G160M | Highly decreases | Highly decreases |
| D218F | Decreases | Decreases |
| D218Y | Decreases | Decreases |
| D218R | No observable effect | No observable effect |

TABLE 5

Critical residues identified for selectivity.

| Mutant | Effect on DR4 binding | Effect on DR5 binding |
|---|---|---|
| R130E | Decreases | Slightly decreases |
| G131R | Decreases | Slightly decreases |
| D269H | Highly decreases | No observable effect |

TABLE 6

The TNF ligand-receptor family and association with autoimmune disease

| Ligands | Receptors | Function | Disease showing association |
|---|---|---|---|
| APRIL | TACI, BCMA and unknown | Probably co-stimulator of B and T cells | RA, SLE |
| 4-1BBL (TNFSF9) | 4-1BB (TNFSFR9) | T-cell costimulator/regulator | EAE, RA |
| BAFF (TNFSF13B/20)* | TACI, BCMA, BAFF-R | B cell survival/maturation, T cell costimulation | SLE, SS, RA |
| CD30L (TNFSF8) | CD30 (TNFSFR8) | Modulator of T cell function | SLE, RA, SS, autoimmune thyroid disease, primary biliary cirrhosis |
| CD40L (TNFSF5)* | CD40(TNFSFR5) | B cell survival, stimulation and differentiation | SLE, SS, IBD, EAE |
| FasL (TNFSF6) | Fas(TNFSFR6), DcR3 | Apoptosis | SLE, EAE, diabetes. autoimmune thyroid disease and autoimmune hepatitis |
| GITRL (TNFSF18) | GITR(TNFSFR18) | T-cell costimulator/regulator | unclear |
| LIGHT (TNFSF14) | LTβ-R, HVEM, DcR3 (TNFSFR6B) | T-cell activation and thymocyte survival | Diabetes, possibly RA |
| LTα (TNFSF1) human | TNF-R1, TNF-R2, HVEM (TNFSFR3) | Inflammation | RA, SLE, IBD, MS, diabetes |
| LTα/β | LTβ-R, HVEM, DcR3 (TNFSFR6B) | Th1 responses, lymph node development, splenic architecture and organization | RA, SLE, IBD, MS, diabetes |
| OX40L (TNFSF4) | OX40 (TNFSFR4) | T-cell costimulator | EAE, RA, IBD |
| RANKL (TNFSF11)* | RANK (TNFSFR11A), OPG | Dendritic cell survival, osteoclast formation | RA |
| TNF (TNFSF2)* | TNF-R1(TNFSFR1A), TNF-R2 (TNFSFR1B) | Inflammation, splenic organization | RA, SLE, IBD, MS, diabetes |
| TRAIL (TNFSF10)* | TRAIL-R1 (DR4, TNFSFR10A), TRAIL-R2 (DR5, TNFSFR10B), TRAIL-R3 (DcR1, TNFSFR10C), TRAIL-R4 (DcR3, TNFSFR10D), OPG (TNFSFR11B) | Induces tumour cell death Blocks T cell proliferation | Favorable in RA model Possible autoimmune thyroid disease; Possibly MS. |
| TWEAK | TWEAK-R | may contribute to macrophage homeostasis by mediating CD4 (+)T-cell killing of antigen-presenting macrophages; Induces proliferation in endothelial cells. | Brain inflammation; angiogenesis. |
| TWEPRIL | Possibly TACI, BCMA and unknown | Requires further elucidation | Requires further elucidation |

MS, multiple sclerosis;
RA, rheumatoid arthritis;
SLE, systemic lupus erythematosus;
SS, Sjörgen's syndrome;
EAE, experimental autoimmune encephalomyelitis;
IBD, inflammatory bowel disease.

Trail Specific Sequences

```
SEQ ID NO: 1 (TRAIL AMINO ACID SEQUENCE)
MAMMEVQGGPSLGQTCVLIVIFTVLLQSLCVAVTYVYFTNELKQMQDKYS

KSGIACFLKEDDSYWDPNDEESMNSPCWQVKWQLRQLVRKMILRTSEETI

STVQEKQQNISPLVRERGPQRVAAHITGTRGRSNTLSSPNSKNEKALGRK

INSWESSRSGHSFLSNLHLRNGELVIHEKGFYYIYSQTYFRFQEEIKENT

KNDKQMVQYIYKYTSYPDPILLMKSARNSCWSKDAEYGLYSIYQGGIFEL

KENDRIFVSVTNEHLIDMDHEASFFGAFLVG

SEQ ID NO: 2 (TRAIL NUCLEOTIDE SEQUENCE)
CCTCACTGACTATAAAAGAATAGAGAAGGAAGGGCTTCAGTGACCGGCTG

CCTGGCTGACTTACAGCAGTCAGACTCTGACAGGATCATGGCTATGATGG

AGGTCCAGGGGGGACCCAGCCTGGGACAGACCTGCGTGCTGATCGTGATC
```

```
-continued
TTCACAGTGCTCCTGCAGTCTCTCTGTGTGGCTGTAACTTACGTGTACTT

TACCAACGAGCTGAAGCAGATGCAGGACAAGTACTCCAAAAGTGGCATTG

CTTGTTTCTTAAAAGAAGATGACAGTTATTGGGACCCCAATGACGAAGAG

AGTATGAACAGCCCCTGCTGGCAAGTCAAGTGGCAACTCCGTCAGCTCGT

TAGAAAGATGATTTTGAGAACCTCTGAGGAAACCATTTCTACAGTTCAAG

AAAAGCAACAAAATATTTCTCCCCTAGTGAGAGAAAGAGGTCCTCAGAGA

GTAGCAGCTCACATAACTGGGACCAGAGGAAGAAGCAACACATTGTCTTC

TCCAAACTCCAAGAATGAAAAGGCTCTGGGCCGCAAAATAAACTCCTGGG

AATCATCAAGGAGTGGGCATTCATTCCTGAGCAACTTGCACTTGAGGAAT

GGTGAACTGGTCATCCATGAAAAAGGGTTTTACTACATCTATTCCCAAAC

ATACTTTCGATTTCAGGAGGAAATAAAAGAAAACACAAAGAACGACAAAC
```

```
AAATGGTCCAATATATTTACAAATACACAAGTTATCCTGACCCTATATTG

TTGATGAAAAGTGCTAGAAATAGTTGTTGGTCTAAAGATGCAGAATATGG

ACTCTATTCCATCTATCAAGGGGAATATTTGAGCTTAAGGAAAATGACA

GAATTTTTGTTTCTGTAACAAATGAGCACTTGATAGACATGGACCATGAA

GCCAGTTTTTTCGGGGCCTTTTTAGTTGGCTAACTGACCTGGAAAGAAAA

AGCAATAACCTCAAAGTGACTATTCAGTTTTCAGGATGATACACTATGAA

GATGTTTCAAAAAATCTGACCAAAACAAACAAACAGAAAACAGAAAACAA

AAAAACCTCTATGCAATCTGAGTAGAGCAGCCACAACCAAAAAATTCTAC

AACACACACTGTTCTGAAAGTGACTCACTTATCCCAAGAAAATGAAATTG

CTGAAAGATCTTTCAGGACTCTACCTCATATCAGTTTGCTAGCAGAAATC

TAGAAGACTGTCAGCTTCCAAACATTAATGCAATGGTTAACATCTTCTGT

CTTTATAATCTACTCCTTGTAAAGACTGTAGAAGAAAGCGCAACAATCCA

TCTCTCAAGTAGTGTATCACAGTAGTAGCCTCCAGGTTTCCTTAAGGGAC

AACATCCTTAAGTCAAAAGAGAGAAGAGGCACCACTAAAAGATCGCAGTT

TGCCTGGTGCAGTGGCTCACACCTGTAATCCCAACATTTTGGGAACCCAA

GGTGGGTAGATCACGAGATCAAGAGATCAAGACCATAGTGACCAACATAG

TGAAACCCCATCTCTACTGAAAGTGCAAAAATTAGCTGGGTGTGTTGGCA

CATGCCTGTAGTCCCAGCTACTTGAGAGGCTGAGGCAGGAGAATCGTTTG

AACCCGGGAGGCAGAGGTTGCAGTGTGGTGAGATCATGCCACTACACTCC

AGCCTGGCGACAGAGCGAGACTTGGTTTCAAAAAAAAAAAAAAAAAAAAA

CTTCAGTAAGTACGTGTTATTTTTTTCAATAAAATTCTATTACAGTATGT

CAAAAAAAAAAAAAAAAA
```

---

The invention claimed is:
1. A TRAIL cytokine, wherein said cytokine has the amino acid sequence of SEQ ID NO: 1, except that it contains the mutations D269H and E195R.

SEQUENCE LISTING

<160> NUMBER OF SEQ ID NOS: 2

<210> SEQ ID NO 1
<211> LENGTH: 281
<212> TYPE: PRT
<213> ORGANISM: Homo sapiens

<400> SEQUENCE: 1

```
Met Ala Met Met Glu Val Gln Gly Gly Pro Ser Leu Gly Gln Thr Cys
 1               5                  10                  15

Val Leu Ile Val Ile Phe Thr Val Leu Leu Gln Ser Leu Cys Val Ala
                20                  25                  30

Val Thr Tyr Val Tyr Phe Thr Asn Glu Leu Lys Gln Met Gln Asp Lys
            35                  40                  45

Tyr Ser Lys Ser Gly Ile Ala Cys Phe Leu Lys Glu Asp Asp Ser Tyr
        50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220
```

| | | | | | | | | | | | | |
|---|---|---|---|---|---|---|---|---|---|---|---|---|
| Ser | Ala | Arg | Asn | Ser | Cys | Trp | Ser | Lys | Asp | Ala | Glu | Tyr | Gly | Leu | Tyr |
| 225 | | | | 230 | | | | | 235 | | | | | 240 | |

Ser Ile Tyr Gln Gly Gly Ile Phe Glu Leu Lys Glu Asn Asp Arg Ile
            245                 250                 255

Phe Val Ser Val Thr Asn Glu His Leu Ile Asp Met Asp His Glu Ala
        260                 265                 270

Ser Phe Phe Gly Ala Phe Leu Val Gly
        275                 280

<210> SEQ ID NO 2
<211> LENGTH: 1772
<212> TYPE: DNA
<213> ORGANISM: Homo sapiens

<400> SEQUENCE: 2

```
cctcactgac tataaaagaa tagagaagga agggcttcag tgaccggctg cctggctgac        60
ttacagcagt cagactctga caggatcatg gctatgatgg aggtccaggg gggacccagc       120
ctgggacaga cctgcgtgct gatcgtgatc ttcacagtgc tcctgcagtc tctctgtgtg       180
gctgtaactt acgtgtactt taccaacgag ctgaagcaga tgcaggacaa gtactccaaa       240
agtggcattg cttgtttctt aaaagaagat gacagttatt gggaccccaa tgacgaagag       300
agtatgaaca gccctgctg gcaagtcaag tggcaactcc gtcagctcgt tagaaagatg       360
attttgagaa cctctgagga aaccatttct acagttcaag aaaagcaaca aaatatttct       420
ccctagtga gagaaagagg tcctcagaga gtagcagctc acataactgg gaccagagga       480
agaagcaaca cattgtcttc tccaaactcc aagaatgaaa aggctctggg ccgcaaaata       540
aactcctggg aatcatcaag gagtgggcat tcattcctga caacttgca cttgaggaat       600
ggtgaactgg tcatccatga aaagggttt tactacatct attcccaaac atactttcga       660
tttcaggagg aaataaaaga aaacacaaag aacgacaaac aaatggtcca atatatttac       720
aaatacacaa gttatcctga ccctatattg ttgatgaaaa gtgctagaaa tagttgttgg       780
tctaaagatg cagaatatgg actctattcc atctatcaag ggggaatatt tgagcttaag       840
gaaaatgaca gaattttgt ttctgtaaca atgagcact tgatagacat ggaccatgaa       900
gccagttttt tcggggcctt tttagttggc taactgacct ggaaagaaaa agcaataacc       960
tcaaagtgac tattcagttt tcaggatgat acactatgaa gatgtttcaa aaatctgac      1020
caaaacaaac aaacagaaaa cagaaaacaa aaaaacctct atgcaatctg agtagagcag      1080
ccacaaccaa aaaattctac aacacacact gttctgaaag tgactcactt atcccaagaa      1140
aatgaaattg ctgaaagatc tttcaggact ctacctcata tcagtttgct agcagaaatc      1200
tagaagactg tcagcttcca acattaatg caatggttaa catcttctgt ctttataatc      1260
tactccttgt aaagactgta aagaaagcg caacaatcca tctctcaagt agtgtatcac      1320
agtagtagcc tccaggtttc cttaagggac aacatcctta agtcaaaaga gagaagaggc      1380
accactaaaa gatcgcagtt tgcctggtgc agtggctcac acctgtaatc ccaacatttt      1440
gggaacccaa ggtgggtaga tcacgagatc aagagatcaa gaccatagtg accaacatag      1500
tgaaacccca tctctactga aagtgcaaaa attagctggg tgtgttggca catgcctgta      1560
gtcccagcta cttgagaggc tgaggcagga gaatcgtttg aacccgggag gcagaggttg      1620
cagtgtggtg agatcatgcc actacactcc agcctggcga cagagcgaga cttggtttca      1680
aaaaaaaaaa aaaaaaaaaa cttcagtaag tacgtgttat tattttttc aataaaattc      1740
tattacagta tgtcaaaaaa aaaaaaaaaa aa                                    1772
```